United States Patent
Morris et al.

(10) Patent No.: US 11,242,531 B2
(45) Date of Patent: Feb. 8, 2022

(54) COMPOSITIONS AND METHODS FOR THE TREATMENT OF HYPERCHOLESTEROLEMIA

(71) Applicant: CITY OF HOPE, Duarte, CA (US)

(72) Inventors: Kevin V. Morris, Sierra Madre, CA (US); Roslyn Ray, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/483,392

(22) PCT Filed: Feb. 2, 2018

(86) PCT No.: PCT/US2018/016727
§ 371 (c)(1),
(2) Date: Aug. 2, 2019

(87) PCT Pub. No.: WO2018/144935
PCT Pub. Date: Aug. 9, 2018

(65) Prior Publication Data
US 2020/0040343 A1 Feb. 6, 2020

Related U.S. Application Data

(60) Provisional application No. 62/454,629, filed on Feb. 3, 2017.

(51) Int. Cl.
*C07H 21/04* (2006.01)
*C12N 15/113* (2010.01)
*A61P 3/06* (2006.01)
*A61K 31/713* (2006.01)

(52) U.S. Cl.
CPC ........ *C12N 15/1138* (2013.01); *A61K 31/713* (2013.01); *A61P 3/06* (2018.01); *C12N 2310/113* (2013.01); *C12N 2310/14* (2013.01); *C12N 2310/315* (2013.01); *C12N 2310/321* (2013.01); *C12N 2310/3341* (2013.01); *C12N 2310/351* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | |
|---|---|---|
| 2009/0186028 A1 | 7/2009 | Iadonato et al. |
| 2010/0267809 A1 | 10/2010 | Rossi et al. |
| 2014/0113957 A1 | 4/2014 | Bettencourt et al. |

FOREIGN PATENT DOCUMENTS

| | | |
|---|---|---|
| WO | WO-2011/053994 A1 | 5/2011 |
| WO | WO-201 5/162422 A1 | 10/2015 |

OTHER PUBLICATIONS

International Search Report dated Apr. 25, 2018, for PCT Application No. PCT/US2018/016727, filed Feb. 2, 2018, 3 pages.
Jeon, H. et al. (2005). "Structure and physiologic function of the low-density lipoprotein receptor," *Annu Rev Biochem* 74:535-562.
Matsui, M. et al. (Dec. 22, 2010). "Activation of LDL Receptor (LDLR) Expression by Small RNAs Complementary to a Noncoding Transcript that Overlaps the LDLR Promoter," *Chem Biol* 17(12):1344-1355.
Written Opinion dated Apr. 25, 2018, for PCT Application No. PCT/US2018/016727, filed Feb. 2, 2018, 11 pages.

*Primary Examiner* — Kimberly Chong
(74) *Attorney, Agent, or Firm* — Mintz, Levin, Cohn, Ferris, Glovsky and Popeo, P.C.

(57) ABSTRACT

Provided herein are, inter alia, compositions and methods for the treatment of hypercholesterolemia. The compositions include double-stranded and single-stranded RNAs capable of repressing lncRNA and concomitantly increasing LDLR activation. The compositions are useful for activating LDLR in liver cells.

3 Claims, 32 Drawing Sheets
Specification includes a Sequence Listing.

LDLR Promoter

COMPOSITIONS AND METHODS FOR THE TREATMENT OF HYPERCHOLESTEROLEMIA

CROSS-REFERENCES TO RELATED APPLICATIONS

This application is the national stage filing under USC 371 of international application PCT/US18/16727, filed Feb. 2, 2018, which claims priority to U.S. Provisional Application No. 62/454,629, filed Feb. 3, 2017, the disclosure of which are incorporated herein in their entirety and for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 048440-646N01US Sequence Listing ST25.TXT, created on Jul. 31, 2019, 13,509 bytes, machine format IBM-PC, MS-Windows operating system, is hereby incorporated by reference in its entirety for all purposes.

BACKGROUND OF THE INVENTION

Hypercholesterolemia is a condition characterized by very high levels of cholesterol in the blood, and is a major correlating factor involved in heart disease. To date, hypercholesterolemia affects approximately 1 in 500 individuals in most countries. A method to specifically reduce cholesterol in the blood in a long term and stable manner would have significant therapeutic impact.

Cholesterol is removed from the blood by the Low-density lipoprotein receptor (LDLR) expressed in the liver. There is a need in the art for compounds that de-repress LDLR expression in the liver and thereby reduce cholesterol levels in the blood. The compositions and methods provided herein cure this and other needs in the art.

BRIEF SUMMARY OF THE INVENTION

In one aspect, there is provided a ribonucleic acid compound including an RNA sequence, the RNA sequence having at least 80% sequence identity to the complement of at least 15 consecutive nucleotides of nucleotides 1-147 of SEQ ID NO:1.

In another aspect, there is provided a ribonucleic acid compound including an RNA sequence, the RNA sequence capable of hybridizing to at least 15 consecutive nucleotides of nucleotides 1-147 of SEQ ID NO:1.

In another aspect, there is provided a ribonucleic acid compound including an RNA sequence, the RNA sequence capable of hybridizing to at least 15 consecutive nucleotides of nucleotides 1-147 of SEQ ID NO:1; and having at least 80% sequence identity to the complement of the consecutive nucleotides.

In another aspect, there is provided a ribonucleic acid compound including an RNA sequence, the RNA sequence having at least 80% sequence identity to the complement of at least 15 consecutive nucleotides of nucleotides 541-631 of SEQ ID NO:2.

In another aspect, there is provided a ribonucleic acid compound including an RNA sequence, the RNA sequence capable of hybridizing to at least 15 consecutive nucleotides of nucleotides 541-631 of SEQ ID NO:2.

In another aspect, there is provided a ribonucleic acid compound including an RNA sequence, the RNA sequence capable of hybridizing to at least 15 consecutive nucleotides of nucleotides 541-631 of SEQ ID NO:2; and having at least 80% sequence identity to the complement of the consecutive nucleotides.

In another aspect, there is provided a ribonucleic acid compound including an RNA sequence, the RNA sequence having at least 80% sequence identity to the complement of at least 15 consecutive nucleotides of nucleotides 1-120 of SEQ ID NO:2.

In another aspect, there is provided a ribonucleic acid compound including an RNA sequence, the RNA sequence capable of hybridizing to at least 15 consecutive nucleotides of nucleotides 1-120 of SEQ ID NO:2.

In another aspect, there is provided a ribonucleic acid compound including an RNA sequence, the RNA sequence capable of hybridizing to at least 15 consecutive nucleotides of nucleotides 1-120 of SEQ ID NO:2; and having at least 80% sequence identity to the complement of the consecutive nucleotides.

BRIEF DESCRIPTION OF THE DRAWINGS

(FIG. 1A) A schematic is shown depicting the LDLR gene and promoter as well as the lncRNA EST BM450697 and small RNAs found to repress EST BM450697 expression. Repression of lncRNA BM450697 ultimately results in the activation of LDLR. (FIG. 1B) The efficacy of LDLR activation in Hep 2G liver cells. (FIG. 1C) The efficacy of LDLR activation in Hep 3B cells. For FIG. 1B and FIG. 1C the average of triplicate experiments are shown with the standard deviations and p values from a paired T-test.

(FIG. 5A) A schematic representation of the PCR strategies employed. (FIG. 5B) HepG2 and Hep3B cells were harvested for RNA, and cDNA was synthesized using an RT specific primer (RT 1-GACCTGCTGTGTCCTAGCTG (SEQ ID NO:38)) and an MM-LV reverse transcriptase (Invitrogen). PCR was performed using primer sets 1 (F-CACTCCAGTCCTTCGAAAGTGTCG (SEQ ID NO:39), R-TTCCTTTGGAGGCAGAGAGGACA (SEQ ID NO:40)) and 2 (F-GGGGCTCCCTCTCACCTATTCT (SEQ ID NO:41), R-GAGGCTGCGAGCATGGG (SEQ ID NO:42)) with 2×NEB MM Taq (New England Biolabs) and the PCR products were visualized on a 1% Agarose TAE gel, electrophoresed for 40 min at 100 V.

(FIG. 9A) Schematic of siRNAs used. Relative (FIG. 9B and FIG. 9C) LDLR and (FIG. 9D) BM450697 mRNA expression levels in Hep3B and HepG2 cells respectively.

(FIG. 10A) Relative LDLR protein expression levels in Hep3B and (FIG. 10B) a representative blot from one IP.

(FIG. 11A) Relative LDLR mRNA expression levels in Hep3B cells following treatment with siRNAs as shown, incubated with or without TSA. (FIG. 11B) Relative LDLR mRNA expression levels in HepG2 cells following treatment with siRNAs as shown, incubated with or without TSA. (FIG. 11C) Relative LDLR mRNA expression levels in Hep3B cells following treatment with siRNAs as shown, incubated with or without azacytidine.

(FIG. 13A) Images were captured using the Zen Imaging Software (version 2.3, Carl Zeiss Microscopy GmbH), and arithmetic mean fluorescence intensity of the LDL-BIODIPY-FL were measured. (FIG. 13B) Representative images of the LDL-uptake assay.

(FIG. 15A) Relative LDLR mRNA expression levels and (FIG. 15B) relative BM450697 mRNA expression levels. Each siRNA conjugate was normalized to their respective scrambled control at each concentration set to 1. A two-way ANOVA with a post-hoc Tukey test was used in (A) with * and ** denoting p<0.001 and p<0.0001 respectively. An unpaired students t-test was performed in (FIG. 15B) with * and ** denoting p<0.05 and p<0.01 respectively.

(FIG. 16A) Primer sets were designed towards different overlapping regions in the LDLR promoter and subsequent qPCR was performed to determine the fold enrichment of BM450697 at the different promoter sites. Samples were calibrated to a fraction of input (1%) and normalized to the scrambled control set to 1. (FIG. 16B) Resultant qPCR using the LDLR primer sets 1-4 as well as off target genes (a downstream 8 kb LDLR gene primer set and GAPDH respectively). BO=Beads only; SCR=scrambled.

DETAILED DESCRIPTION OF THE INVENTION

Definitions

Figure 1A:
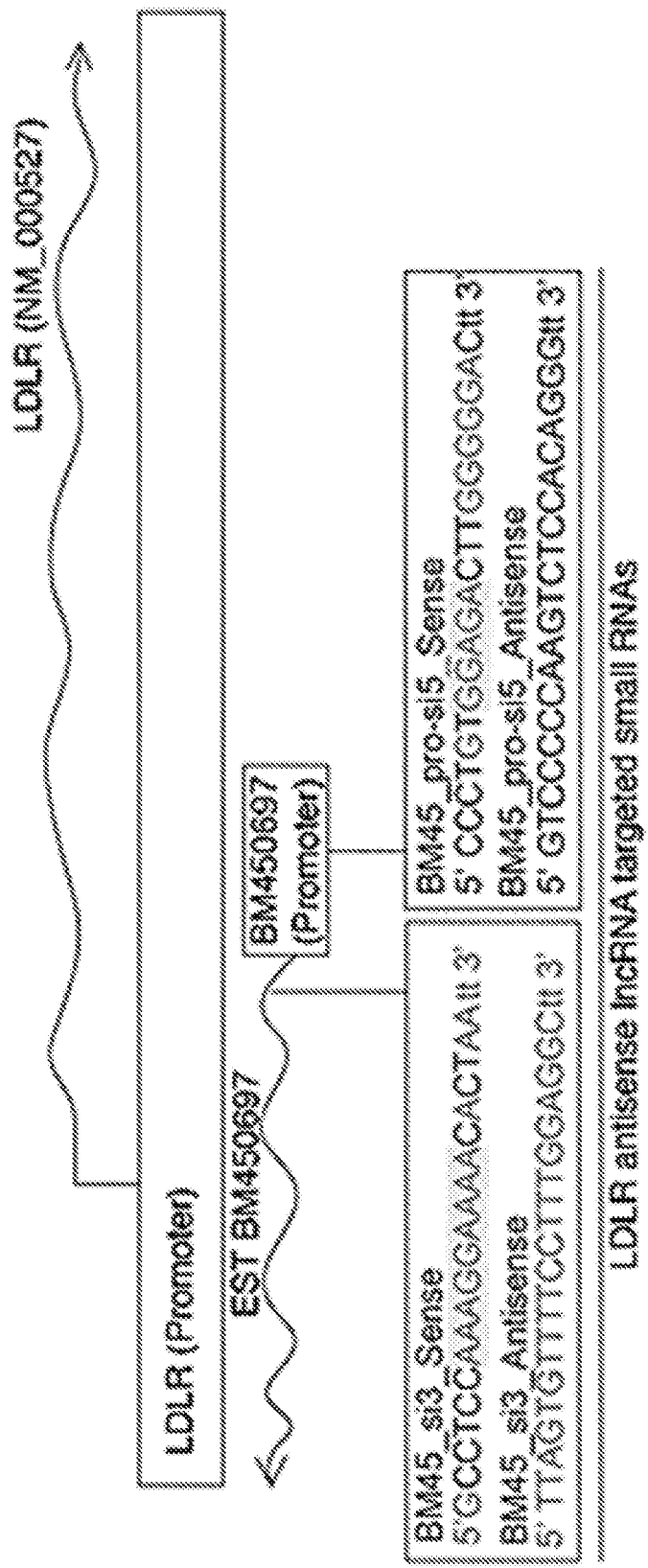
FIGS. 1A-1C. Small RNA targeting of LDLR regulatory lncRNA BM450697 (SEQ ID NO:2).

While various embodiments and aspects of the present invention are shown and described herein, it will be obvious to those skilled in the art that such embodiments and aspects are provided by way of example only. Numerous variations, changes, and substitutions will now occur to those skilled in the the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "long non-coding RNA", "lncRNA" or "lncRNA transcript" refers to a non-protein coding RNA molecule, which regulates the activity (e.g., expression and/or transcription) of a target RNA (e.g., LDLR RNA) by binding (hybridizing) to said target RNA (e.g., LDLR RNA). The lncRNA provided herein including embodiments thereof is capable of hybridizing (binding) to an LDLR RNA transcript, thereby modulating (inhibiting) its expression. The lncRNA provided herein including embodiments thereof may include 200 or more nucleotides (e.g., 210, 220, 230, 250, 275, 300, 500, 600, 650, 700, 800, 900, 1000, 1100, 1200, or 1300 nucleotides in length). In embodiments, the lncRNA is about 660 nucleotides in length. In embodiments, the lncRNA is about 301 nucleotides in length. In embodiments, the lncRNA is about 961 nucleotides in length. In embodiments, the lncRNA is about 1227 nucleotides in length. In embodiments, the lncRNA is 660 nucleotides in length. In embodiments, the lncRNA is 301 nucleotides in length. In embodiments, the lncRNA is 961 nucleotides in length. In embodiments, the lncRNA is 1227 nucleotides in length.

In embodiments, the lncRNA is the sequence identified by the NCBI EST reference number EST BM450697, a homolog or functional fragment thereof. In embodiments, the lncRNA includes the sequence of SEQ ID NO:23. In embodiments, the lncRNA is the sequence of SEQ ID NO:23. In embodiments, the lncRNA includes the sequence of SEQ ID NO:2. In embodiments, the lncRNA is the sequence of SEQ ID NO:2. In embodiments, the lncRNA includes a lncRNA promoter sequence. In embodiments, the lncRNA promoter sequence includes the sequence of SEQ ID NO:1. In embodiments, the lncRNA promoter sequence is the sequence of SEQ ID NO:1. A "lncRNA promoter sequence" is a sequence regulating transcription of a lncRNA. The lncRNA promoter sequence is located at the 5' end of a lncRNA and is also referred to herein as "5' untranslated region" or "5'UTR". In embodiments, the lncRNA promoter sequence forms part of the sequence identified by the NCBI EST reference number EST BM450697, a homolog or functional fragment thereof.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of nucleic acid molecules (e.g., mRNA or lncRNA) may be detected by standard PCR or Northern blot methods well known in the art. See, Sambrook et al., 1989 *Molecular Cloning: A Laboratory Manual*, 18.1-18.88.

An "antisense nucleic acid" as referred to herein is a nucleic acid (e.g., DNA or RNA molecule) that is complementary and capable of binding (hybridizing) to at least a portion of a specific target nucleic acid (e.g., lncRNA or lncRNA promoter sequence). The antisense nucleic acid as provided herein is capable of reducing transcription of the target nucleic acid, reducing the translation of the target nucleic acid, altering the target nucleic acid splicing, or interfering with the endogenous activity of the target nucleic acid. See, e.g., Weintraub, *Scientific American*, 262:40 (1990). Typically, antisense nucleic acids (e.g. oligonucleotides) are generally between 15 and 25 bases in length and are capable of hybridizing to (e.g. selectively hybridizing to) a target nucleic acid (e.g., lncRNA). In embodiments, the antisense nucleic acid hybridizes to the target nucleic acid sequence (e.g. lncRNA or lncRNA promoter sequence) under stringent hybridization conditions. In embodiments, the antisense nucleic acid hybridizes to the target nucleic acid (e.g. lncRNA or lncRNA promoter sequence) under moderately stringent hybridization conditions. In embodiments, the antisense nucleic acid hybridizes to the target nucleic acid (e.g. lncRNA or lncRNA promoter sequence) in vitro. In embodiments, the antisense nucleic acid hybridizes to the target nucleic acid (e.g. lncRNA or lncRNA promoter sequence) in a cell. In embodiments, the antisense nucleic acid hybridizes to the target nucleic acid (e.g. lncRNA or lncRNA promoter sequence) in an organism. In embodiments, the antisense nucleic acid hybridizes to the target nucleic acid (e.g. lncRNA or lncRNA promoter sequence) under physiological conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding RNA (e.g., lncRNA or lncRNA promoter sequence) forming a double-stranded molecule. Through binding (hybridizing) to the RNA the antisense nucleic acids interfere with the endogenous activity and/or function of the RNA (e.g., lncRNA or lncRNA promoter sequence). For example, the double-stranded molecule may be degraded via the RNAi pathway. The use of antisense methods to inhibit the in vitro translation of genes is well known in the art (Marcus-Sakura, *Anal. Biochem.*, 172:289, (1988)). Antisense nucleic acids may be single or double stranded nucleic acids. Non-limiting examples of antisense nucleic acids include siRNAs including their derivatives or pre-cursors, such as nucleotide analogs, short hairpin RNAs (shRNA), micro RNAs (miRNA) or certain of their derivatives or pre-cursors.

A "small RNA," "siRNA," "small interfering RNA," or "RNAi" as provided herein refers to a double-stranded or single-stranded ribonucleic acid that has the ability to reduce or inhibit expression of a gene or the activity of a target nucleic acid (e.g., a single-stranded or double-stranded RNA or a single-stranded or double-stranded DNA) when expressed in the same cell as the gene or target gene. Where the small RNA is a double-stranded RNA, the complementary portions of the ribonucleic acid that hybridize to form the double stranded molecule typically have substantial or complete identity. In one embodiment, a small RNA is a nucleic acid that has substantial or complete identity to a target RNA (e.g., a lncRNA or a lncRNA promoter sequence) and forms a double stranded small RNA. In embodiments, the small RNA inhibits gene expression by interacting with a complementary cellular RNA (e.g., a lncRNA or a lncRNA promoter sequence) thereby interfering with the endogenous activity and/or function of the complementary cellular RNA (e.g., a lncRNA or a lncRNA promoter sequence). Typically, the nucleic acid is at least about 15-50 nucleotides in length (e.g., each complementary sequence of the double stranded small RNA is 15-50 nucleotides in length, and the double stranded small RNA is about 15-50 base pairs in length). The small RNAs provided herein regulate expression of a target gene or activity of a target nucleic acid (e.g., lncRNA) by hybridizing to the mRNA of said gene or by hybridizing to the promoter of said target nucleic acid (e.g., lncRNA) or the target nucleic acid itself (e.g., lncRNA). Where the small RNA hybridizes to a promoter of a gene thereby modulating the expression of said gene, the small RNA may be referred to as "antigen RNA" or "agRNA." In embodiments, the small RNA hybridizes (binds) to a lncRNA. In embodiments, the RNA sequence provided herein is a small RNA. In embodiments, the small RNA hybridizes (binds) to a lncRNA promoter sequence. In embodiments, the RNA sequence is a small RNA. In embodiments, the small RNA has the sequence of the RNA sequence. In embodiments, the small RNA includes the sequence of the RNA sequence. Thus, in embodiments the nucleic acid compound includes a small RNA.

In embodiments, the small RNA includes the sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22. In embodiments, the small RNA is the sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22. Thus, in embodiments, the RNA sequence includes the sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22. In embodiments, the RNA sequence is the sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22. In embodiments, the RNA sequence includes the sequence of SEQ ID NO:12. In embodiments, the RNA sequence includes the sequence of SEQ ID NO:18. In embodiments, the RNA sequence includes the sequence of SEQ ID NO:22. In embodiments, the RNA sequence is the sequence of SEQ ID NO:12. In embodiments, the RNA sequence is the sequence of SEQ ID NO:18. In embodiments, the RNA sequence is the sequence of SEQ ID NO:22.

In embodiments, the RNA sequence includes the sequence of SEQ ID NO:3. In embodiments, the RNA sequence includes the sequence of SEQ ID NO:4. In embodiments, the RNA sequence includes the sequence of SEQ ID NO:5. In embodiments, the RNA sequence includes the sequence of SEQ ID NO:6. In embodiments, the RNA sequence includes the sequence of SEQ ID NO:7. In embodiments, the RNA sequence includes the sequence of SEQ ID NO:8. In embodiments, the RNA sequence includes the sequence of SEQ ID NO:9. In embodiments, the RNA sequence includes the sequence of SEQ ID NO:10. In embodiments, the RNA sequence includes the sequence of SEQ ID NO:11. In embodiments, the RNA sequence includes the sequence of SEQ ID NO:12. In embodiments, the RNA sequence includes the sequence of SEQ ID NO:13. In embodiments, the RNA sequence includes the sequence of SEQ ID NO:14. In embodiments, the RNA sequence includes the sequence of SEQ ID NO:15. In embodiments, the RNA sequence includes the sequence of SEQ ID NO:16. In embodiments, the RNA sequence includes the sequence of SEQ ID NO:17. In embodiments, the RNA sequence includes the sequence of SEQ ID NO:18. In embodiments, the RNA sequence includes the sequence of SEQ ID NO:19. In embodiments, the RNA sequence includes the sequence of SEQ ID NO:20. In embodiments, the RNA sequence includes the sequence of SEQ ID NO:21. In embodiments, the RNA sequence includes the sequence of SEQ ID NO:22.

In embodiments, the RNA sequence is the sequence of SEQ ID NO:3. In embodiments, the RNA sequence is the sequence of SEQ ID NO:4. In embodiments, the RNA sequence is the sequence of SEQ ID NO:5. In embodiments, the RNA sequence is the sequence of SEQ ID NO:6. In embodiments, the RNA sequence is the sequence of SEQ ID NO:7. In embodiments, the RNA sequence is the sequence of SEQ ID NO:8. In embodiments, the RNA sequence is the sequence of SEQ ID NO:9. In embodiments, the RNA sequence is the sequence of SEQ ID NO:10. In embodiments, the RNA sequence is the sequence of SEQ ID NO:11. In embodiments, the RNA sequence is the sequence of SEQ ID NO:12. In embodiments, the RNA sequence is the sequence of SEQ ID NO:13. In embodiments, the RNA sequence is the sequence of SEQ ID NO:14. In embodiments, the RNA sequence is the sequence of SEQ ID NO:15. In embodiments, the RNA sequence is the sequence of SEQ ID NO:16. In embodiments, the RNA sequence is the sequence of SEQ ID NO:17. In embodiments, the RNA sequence is the sequence of SEQ ID NO:18. In embodiments, the RNA sequence is the sequence of SEQ ID NO:19. In embodiments, the RNA sequence is the sequence of SEQ ID NO:20. In embodiments, the RNA sequence is the sequence of SEQ ID NO:21. In embodiments, the RNA sequence is the sequence of SEQ ID NO:22.

The term "post-transcriptional gene silencing" or "PTGS" refers to the inhibition of expression of a gene by modulating the activity and/or function of the RNA transcript of said gene. For example, a small RNA hybridizes (binds) to said RNA transcript (e.g., lncRNA) thereby inducing the degradation of said target RNA transcript. Thus, a "PTGS RNA" as provided herein refers to a small RNA (siRNA) capable of reducing or inhibiting expression of a target RNA through binding (hybridizing) to the target RNA (e.g., lncRNA) and thereby initiating the degradation of said target RNA.

The term "transcriptional gene silencing" or "TGS" refers to the transcriptional inhibition of a target RNA through binding (hybridizing) of a small RNA to the promoter of said target RNA (e.g., lncRNA promoter sequence). Thus, a "TGS RNA" as provided herein refers to a small RNA (siRNA) capable of reducing or inhibiting expression of a target RNA through binding (hybridizing) to the RNA promoter sequence (e.g., lncRNA promoter sequence) that controls expression of said target RNA, thereby inhibiting transcription of the RNA (e.g., lncRNA).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

As used herein, the term "conjugate" refers to the association between atoms or molecules. The association can be direct or indirect. For example, a conjugate between a nucleic acid (e.g., ribonucleic acid) and a compound moiety as provided herein can be direct, e.g., by covalent bond, or indirect, e.g., by non-covalent bond. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. Thus, the nucleic acids can be attached to a compound moiety through its backbone. Optionally, the ribonucleic acid includes one or more reactive moieties, e.g., an amino acid reactive moiety, that facilitates the interaction of the ribonucleic acid with the compound moiety. In embodiments, the RNA sequence (e.g., small RNA) is conjugated to a compound moiety. The compound moiety may be covalently attached to the RNA sequence (e.g., small RNA, siRNA) provided herein including embodiments, thereof. In embodiments, the compound moiety is attached to the RNA sequence through a chemical linker.

A chemical linker as provided herein is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties is chemically different.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "Tat," "Tat protein," as provided herein includes any of the naturally-occurring forms of the trans-activator of transcription (Tat) protein or variants or homologs thereof that maintain the activity of the Tat polypeptide (e.g. within at least 50%, 80%, 90%, 95%, 96%, 97%, 98%, 99% or 100% activity compared to Tat). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Tat polypeptide. In embodiments, the Tat polypeptide is the protein as identified by the UniProt reference P04608, or homologs, variants, or functional fragments thereof. In embodiments, Tat includes the sequence of SEQ ID NO:37. In embodiments, Tat is the sequence of SEQ ID NO:37.

The term "LDLR" or "LDLR protein" as provided herein includes any of the naturally-occurring forms of the Low-density lipoprotein receptor (LDLR) or variants or homologs thereof that maintain the activity of LDLR polypeptide (e.g. within at least 50%, 80%, 90%, 95%, 96%, 97%, 98%, 99% or 100% activity compared to LDLR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring LDLR polypeptide. In embodiments, the LDLR polypeptide is the protein as identified by the UniProt reference P01130, homolog or functional fragment thereof. In embodiments, the LDLR polypeptide is encoded by a nucleic acid sequence identified by the NCBI sequence reference GI:225131046, homolog or functional fragment thereof.

The terms "LDLR transcript" and "LDLR RNA" as provided herein include any of the naturally-occurring forms of the Low-density lipoprotein receptor (LDLR) RNA or variants or homologs thereof that code for an LDLR polypeptide capable of maintaining the activity of the LDLR polypeptide (e.g. within at least 50%, 80%, 90%, 95%, 96%, 97%, 98%, 99% or 100% activity compared to LDLR). In some aspects, the variants or homologs have at least 90%, 95%, 96%, 97%, 98%, 99% or 100% nucleotide sequence identity across the whole sequence or a portion of the sequence (e.g. a 50, 100, 150 or 200 continuous nucleotide sequence portion) compared to a naturally occurring LDLR RNA. In embodiments, the LDLR RNA is the nucleic acid sequence as identified by the Ensembl ID: ENST00000558518.5, homolog or functional fragment thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA*

85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a first nucleic acid compound (e.g., ribonucleic acid compound) as described herein and a second nucleic acid as described herein (e.g., lncRNA).

The term "activating," as used herein, refers to a nucleic acid sequence (e.g., small RNA) capable of detectably increasing the expression or activity of a given gene or protein (e.g., LDLR). The activating nucleic acid can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid.

As defined herein, the term "inhibition", "inhibit", "inhibiting" and the like in reference to a small RNA (e.g., RNA sequence provided herein) or siRNA means negatively affecting (e.g., decreasing) the activity or function of a target RNA (e.g. decreasing gene transcription or translation) relative to the activity or function of the target RNA (e.g., lncRNA) in the absence of the inhibitor. In embodiments, inhibition refers to reduction of lncRNA expression. In embodiments, inhibition refers to reduction of lncRNA transcription. Thus, inhibition includes, at least in part, partially or totally blocking stimulation, decreasing, preventing, or delaying activation, or inactivating, desensitizing, or down-regulating transcription of the target RNA (e.g., lncRNA). In embodiments, inhibition refers to inhibition of a lncRNA. In embodiments, inhibition refers to inhibition of a lncRNA promoter sequence.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" may be a small RNA, (e.g., siRNA, shRNA, miRNA) that inhibits lncRNA activity (e.g., expression, transcription) e.g., by binding, partially or totally blocking stimulation, decrease, prevent, or delay activation, or inactivate, desensitize, or down-regulate lncRNA expression.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refer to a state of being or health status of a patient or subject capable of being treated with a compound, pharmaceutical composition, or method provided herein. In embodiments, the disease is hypercholesterolemia.

"Hypercholesterolemia," also known as high cholesterol, as provided herein refers to a disease wherein a subject (e.g., human) displays high levels of blood cholesterol (e.g., low-density lipoprotein (LDL)) that fall outside of the art accepted normal range. Hypercholesterolemia may be hereditary (e.g., familial hypercholesterolemia) or induced by a number of environmental factors, including obesity, diet, and stress. Hypercholesterolemia may lead to atherosclerosis and/or heart disease.

The term "associated" or "associated with" in the context of a substance or substance activity or function associated with a disease (e.g., hypercholesterolemia) means that the disease (e.g., hypercholesterolemia) is caused by (in whole or in part), or a symptom of the disease is caused by (in whole or in part) the substance or substance activity or function.

"Patient" or "subject in need thereof" refers to a living organism suffering from or prone to a disease (e.g., hypercholesterolemia) or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder (e.g., hypercholesterolemia) being treated. Also, a therapeutic benefit is achieved with the eradication or amelioration of one or more of the physiological symptoms associated with the underlying disorder (e.g., hypercholesterolemia) such that an improvement is observed in the patient, notwithstanding that the patient may still be afflicted with the underlying disorder. For prophylactic benefit, the compositions may be administered to a patient at risk of developing a particular disease (e.g., hypercholesterolemia), or to a patient reporting one or more of the physiological symptoms of a disease (e.g., hypercholesterolemia), even though a diagnosis of this disease (e.g., hypercholesterolemia) may not have been made. Treatment includes preventing the disease (e.g., hypercholesterolemia), that is, causing the clinical symptoms of the disease (e.g., hypercholesterolemia) not to develop by administration of a protective composition prior to the induction of the disease; suppressing the disease, that is, causing the clinical symptoms of the disease (e.g., hypercholesterolemia) not to develop by administration of a protective composition after the inductive event but prior to the clinical appearance or reappearance of the disease (e.g., hypercholesterolemia); inhibiting the disease (e.g., hypercholesterolemia), that is, arresting the development of clinical symptoms by administration of a protective composition after their initial appearance; preventing re-occurring of the disease (e.g., hypercholesterolemia) and/or relieving the disease (e.g., hypercholesterolemia), that is, causing the regression of clinical symptoms by administration of a protective composition after their initial appearance.

An "effective amount" is an amount sufficient to accomplish a stated purpose (e.g. achieve the effect for which it is administered, treat a disease, reduce one or more symptoms of a disease or condition (e.g., hypercholesterolemia), activate LDLR expression). An example of an "effective amount" is an amount sufficient to contribute to the treatment, prevention, or reduction of a symptom or symptoms of a disease (e.g., hypercholesterolemia), which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of a disease, pathology or condition (e.g., hypercholesterolemia), or reducing the likelihood of the onset (or reoccurrence) of a disease, pathology, or condition (e.g., hypercholesterolemia), or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme, RNA or protein relative to the absence of the antagonist. A "function disrupting amount," as used herein, refers to the amount of antagonist required to disrupt the function of an enzyme, RNA or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, formulated as applicator sticks, solutions, suspensions, emulsions, gels, creams, ointments, pastes, jellies, paints, powders, and aerosols.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the ribonucleic acid compounds provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Ribonucleic Acid Compounds

Provided herein, inter alia, are compositions and methods for the treatment of hypercholesterolemia. The ribonucleic acid compounds provided herein are, inter alia, useful for the long-term activation of Low-density lipoprotein receptor (LDLR) protein in liver cells resulting in the stable reduction of cholesterol in the blood. The ribonucleic acid compounds provided herein are capable of binding (hybridizing) to a long non-coding RNA (lncRNA) and/or its promoter (lncRNA promoter sequence), which independently inhibit LDLR expression. Through binding (hybridizing) of the ribonucleic acid compounds provided herein to the lncRNA and/or its promoter (lncRNA promoter sequence), the lncRNA is prevented from exerting its inhibitory effect on LDLR expression resulting in activation of LDLR expression. Provided herein are small RNAs that bind to the lncRNA (e.g., the sequence of SEQ ID NO:2 or functional fragments or homologs thereof (e.g., SEQ ID NO:23)) or a lncRNA promoter sequence (e.g., the sequence of SEQ ID NO:1 or functional fragments or homologs thereof). Small RNAs capable of binding (hybridizing) to the lncRNA (e.g., the sequence of SEQ ID NO:2 or functional fragments or homologs thereof) may be PTGS RNAs, while small RNAs capable of binding to the lncRNA promoter sequence (e.g., the sequence of SEQ ID NO:1 or functional fragments or homologs thereof) may be TGS RNAs. By simple injection into the blood, the ribonucleic acid compounds provided herein can be easily targeted to the liver to exert their function of LDLR activation. The ibonucleic acid compounds provided herein may include a targeting moiety, which targets the compound to an organ (e.g., liver). Thus, in embodiments the targeting moiety is a liver targeting moiety.

Thus, the ribonucleic acid compound as provided herein, including embodiments thereof, is capable of detectably increasing the expression or activity of LDLR relative to the absence of the ribonucleic acid compound. The ribonucleic acid compound provided herein may increase expression or activity of LDLR may be 1.5-fold, 2-fold, 3-fold, 4-fold, 5-fold, 10-fold, or more relative to the absence of the ribonucleic acid compound.

The ribonucleic acid compound as provided herein including embodiments thereof, may include nucleotide mutations, deletions, insertions, or substitutions. A nucleotide substitution in a ribonucleic acid compound refers to replacement of one or more nucleotides with one or more different (not the same nucleotide as in the parent sequence) nucleotides at a particular position relative to a parent ribonucleic acid sequence. An insertion in a ribonucleic acid compound refers to the insertion of one or more nucleotides at one or more particular positions relative to a parent ribonucleic acid sequence. A deletion in a ribonucleic acid sequence refers to the removal of one or more nucleotides from one or more particular positions relative to a parent ribonucleic acid sequence. Thus, substitutions, insertions, or deletions can take place at one or more nucleotide positions in a nucleic acid sequence. Further, substitutions, insertions, and deletions may exist concurrently within a single ribonucleic acid sequence.

Small RNAs Binding lncRNA Promoter Sequences

In a first aspect, there is provided a ribonucleic acid compound including an RNA sequence, the RNA sequence having at least 80% sequence identity to the complement of at least 15 consecutive nucleotides of nucleotides 1-147 of SEQ ID NO:1.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region). Therefore, the RNA sequences provided herein (e.g., the sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22) may have a sequence identity from about 80% to about 100%.

In embodiments, the RNA sequence has at least 85% sequence identity to the complement of at least 15 consecutive nucleotides of nucleotides 1-147 of SEQ ID NO:1. In embodiments, the RNA sequence has at least 86% sequence identity to the complement of at least 15 consecutive nucleotides of nucleotides 1-147 of SEQ ID NO:1. In embodiments, the RNA sequence has at least 87% sequence identity to the complement of at least 15 consecutive nucleotides of nucleotides 1-147 of SEQ ID NO:1. In embodiments, the RNA sequence has at least 88% sequence identity to the complement of at least 15 consecutive nucleotides of nucleotides 1-147 of SEQ ID NO:1. In embodiments, the RNA sequence has at least 89% sequence identity to the complement of at least 15 consecutive nucleotides of nucleotides 1-147 of SEQ ID NO:1. In embodiments, the RNA sequence has at least 90% sequence identity to the complement of at least 15 consecutive nucleotides of nucleotides 1-147 of SEQ ID NO:1. In embodiments, the RNA sequence has at least 91% sequence identity to the complement of at least 15 consecutive nucleotides of nucleotides 1-147 of SEQ ID NO:1. In embodiments, the RNA sequence has at least 92% sequence identity to the complement of at least 15 consecutive nucleotides of nucleotides 1-147 of SEQ ID NO:1. In embodiments, the RNA sequence has at least 93% sequence identity to the complement of at least 15 consecutive nucleotides of nucleotides 1-147 of SEQ ID NO:1. In embodiments, the RNA sequence has at least 94% sequence identity to the complement of at least 15 consecutive nucleotides of nucleotides 1-147 of SEQ ID NO:1. In embodiments, the RNA sequence has at least 95% sequence identity to the complement of at least 15 consecutive nucleotides of nucleotides 1-147 of SEQ ID NO:1. In embodiments, the RNA sequence has at least 96% sequence identity to the complement of at least 15 consecutive nucleotides of nucleotides 1-147 of SEQ ID NO:1. In embodiments, the RNA sequence has at least 97% sequence identity to the complement of at least 15 consecutive nucleotides of nucleotides 1-147 of SEQ ID NO:1. In embodiments, the RNA sequence has at least 98% sequence identity to the complement of at least 15 consecutive nucleotides of nucleotides 1-147 of SEQ ID NO:1. In embodiments, the RNA sequence has at least 99% sequence identity to the complement of at least 15 consecutive nucleotides of nucleotides 1-147 of SEQ ID NO:1.

In embodiments, the RNA sequence has 85% sequence identity to the complement of at least 15 consecutive nucleotides of nucleotides 1-147 of SEQ ID NO:1. In embodiments, the RNA sequence has 86% sequence identity to the complement of at least 15 consecutive nucleotides of nucleotides 1-147 of SEQ ID NO:1. In embodiments, the RNA sequence has 87% sequence identity to the complement of at least 15 consecutive nucleotides of nucleotides 1-147 of SEQ ID NO:1. In embodiments, the RNA sequence has 88% sequence identity to the complement of at least 15 consecutive nucleotides of nucleotides 1-147 of SEQ ID NO:1. In embodiments, the RNA sequence has 89% sequence identity to the complement of at least 15 consecutive nucleotides of nucleotides 1-147 of SEQ ID NO:1. In embodiments, the RNA sequence has 90% sequence identity to the complement of at least 15 consecutive nucleotides of nucleotides 1-147 of SEQ ID NO:1. In embodiments, the RNA sequence has 91% sequence identity to the complement of at least 15 consecutive nucleotides of nucleotides 1-147 of SEQ ID NO:1. In embodiments, the RNA sequence has 92% sequence identity to the complement of at least 15 consecutive nucleotides of nucleotides 1-147 of SEQ ID NO:1. In embodiments, the RNA sequence has 93% sequence identity to the complement of at least 15 consecutive nucleotides of nucleotides 1-147 of SEQ ID NO:1. In embodiments, the RNA sequence has 94% sequence identity to the complement of at least 15 consecutive nucleotides of nucleotides 1-147 of SEQ ID NO:1. In embodiments, the RNA sequence has 95% sequence identity to the complement of at least 15 consecutive nucleotides of nucleotides 1-147 of SEQ ID NO:1. In embodiments, the RNA sequence has 96% sequence identity to the complement of at least 15 consecutive nucleotides of nucleotides 1-147 of SEQ ID NO:1. In embodiments, the RNA sequence has 97% sequence identity to the complement of at least 15 consecutive nucleotides of nucleotides 1-147 of SEQ ID NO:1. In embodiments, the RNA sequence has 98% sequence identity to the complement of at least 15 consecutive nucleotides of nucleotides 1-147 of SEQ ID NO:1. In embodiments, the RNA sequence has 99% sequence identity to the complement of at least 15 consecutive nucleotides of nucleotides 1-147 of SEQ ID NO:1.

In embodiments, the RNA sequence has 85% sequence identity to the complement of 15 consecutive nucleotides of nucleotides 1-147 of SEQ ID NO:1. In embodiments, the RNA sequence has 86% sequence identity to the complement of 15 consecutive nucleotides of nucleotides 1-147 of SEQ ID NO:1. In embodiments, the RNA sequence has 87% sequence identity to the complement of 15 consecutive nucleotides of nucleotides 1-147 of SEQ ID NO:1. In embodiments, the RNA sequence has 88% sequence identity to the complement of 15 consecutive nucleotides of nucleotides 1-147 of SEQ ID NO:1. In embodiments, the RNA sequence has 89% sequence identity to the complement of 15 consecutive nucleotides of nucleotides 1-147 of SEQ ID NO:1. In embodiments, the RNA sequence has 90% sequence identity to the complement of 15 consecutive nucleotides of nucleotides 1-147 of SEQ ID NO:1. In embodiments, the RNA sequence has 91% sequence identity to the complement of 15 consecutive nucleotides of nucleotides 1-147 of SEQ ID NO:1. In embodiments, the RNA sequence has 92% sequence identity to the complement of 15 consecutive nucleotides of nucleotides 1-147 of SEQ ID NO:1. In embodiments, the RNA sequence has 93% sequence identity to the complement of 15 consecutive nucleotides of nucleotides 1-147 of SEQ ID NO:1. In embodiments, the RNA sequence has 94% sequence identity to the complement of 15 consecutive nucleotides of nucleotides 1-147 of SEQ ID NO:1. In embodiments, the RNA sequence has 95% sequence identity to the complement of 15 consecutive nucleotides of nucleotides 1-147 of SEQ ID NO:1. In embodiments, the RNA sequence has 96% sequence identity to the complement of 15 consecutive nucleotides of nucleotides 1-147 of SEQ ID NO:1. In embodiments, the RNA sequence has 97% sequence identity to the complement of 15 consecutive nucleotides of nucleotides 1-147 of SEQ ID NO:1. In embodiments, the RNA sequence has 98% sequence identity to the complement of 15 consecutive nucleotides of nucleotides 1-147 of SEQ ID NO:1. In embodiments, the RNA sequence has 99% sequence identity to the complement of 15 consecutive nucleotides of nucleotides 1-147 of SEQ ID NO:1. In embodiments, the RNA sequence has 100% sequence identity to the complement of 15 consecutive nucleotides of nucleotides 1-147 of SEQ ID NO:1.

The ribonucleic acid compounds provided herein may hybridize (bind) to a lncRNA (e.g., the sequence of SEQ ID NO:2) or a lncRNA promoter sequence (e.g., the sequence of SEQ ID NO:1). The ribonucleic acid compounds provided herein may hybridize (bind) to a specific number of nucleotides within the lncRNA or lncRNA promoter sequence and the nucleotides may be consecutive nucleotides. For example, the RNA sequence included in the ribonucleic acid compounds provided herein may bind to at least 15 consecutive nucleotides of SEQ ID NO:1 or SEQ ID NO:2. In embodiments, the RNA sequence included in the ribonucleic acid compounds provided herein binds to 15 consecutive nucleotides of SEQ ID NO:1 or SEQ ID NO:2.

In embodiments, the RNA sequence has at least 80% sequence identity to the complement of at least 15 consecutive nucleotides of nucleotides 1-147 of SEQ ID NO:1. In embodiments, the RNA sequence has at least 80% sequence identity to the complement of at least 16 consecutive nucleotides of nucleotides 1-147 of SEQ ID NO:1. In embodiments, the RNA sequence has at least 80% sequence identity to the complement of at least 17 consecutive nucleotides of nucleotides 1-147 of SEQ ID NO:1. In embodiments, the RNA sequence has at least 80% sequence identity to the complement of at least 18 consecutive nucleotides of nucleotides 1-147 of SEQ ID NO:1. In embodiments, the RNA sequence has at least 80% sequence identity to the complement of at least 19 consecutive nucleotides of nucleotides 1-147 of SEQ ID NO:1. In embodiments, the RNA sequence has at least 80% sequence identity to the complement of at least 20 consecutive nucleotides of nucleotides 1-147 of SEQ ID NO:1. In embodiments, the RNA sequence has at least 80% sequence identity to the complement of at least 25 consecutive nucleotides of nucleotides 1-147 of SEQ ID NO:1. In embodiments, the RNA sequence has at least 80% sequence identity to the complement of at least 30 consecutive nucleotides of nucleotides 1-147 of SEQ ID NO:1. In embodiments, the RNA sequence has at least 80% sequence identity to the complement of at least 35 consecutive nucleotides of nucleotides 1-147 of SEQ ID NO:1. In embodiments, the RNA sequence has at least 80% sequence identity to the complement of at least 40 consecutive nucleotides of nucleotides 1-147 of SEQ ID NO:1. In embodiments, the RNA sequence has at least 80% sequence identity to the complement of at least 45 consecutive nucleotides of nucleotides 1-147 of SEQ ID NO:1. In embodiments, the RNA sequence has at least 80% sequence identity to the complement of at least 50 consecutive nucleotides of nucleotides 1-147 of SEQ ID NO:1. For the above embodiments, the RNA sequence may have about 85%, 90%, 92%, 93%, 94%, 95%, 96%, 97%, 98% or 99% sequence identity to the complement of at least 15 (e.g., 15, 16, 17, 18, 19, 20, 21, 22, 23, or 25) consecutive nucleotides of nucleotides 1-147 of SEQ ID NO:1.

In embodiments, the RNA sequence has 80% sequence identity to the complement of at least 15 consecutive nucleotides of nucleotides 1-147 of SEQ ID NO:1. In embodiments, the RNA sequence has 80% sequence identity to the complement of at least 16 consecutive nucleotides of nucleotides 1-147 of SEQ ID NO:1. In embodiments, the RNA sequence has 80% sequence identity to the complement of at least 17 consecutive nucleotides of nucleotides 1-147 of SEQ ID NO:1. In embodiments, the RNA sequence has 80% sequence identity to the complement of at least 18 consecutive nucleotides of nucleotides 1-147 of SEQ ID NO:1. In embodiments, the RNA sequence has 80% sequence identity to the complement of at least 19 consecutive nucleotides of nucleotides 1-147 of SEQ ID NO:1. In embodiments, the RNA sequence has 80% sequence identity to the complement of at least 20 consecutive nucleotides of nucleotides 1-147 of SEQ ID NO:1. In embodiments, the RNA sequence has 80% sequence identity to the complement of at least 25 consecutive nucleotides of nucleotides 1-147 of SEQ ID NO:1. In embodiments, the RNA sequence has 80% sequence identity to the complement of at least 30 consecutive nucleotides of nucleotides 1-147 of SEQ ID NO:1. In embodiments, the RNA sequence has 80% sequence identity to the complement of at least 35 consecutive nucleotides of nucleotides 1-147 of SEQ ID NO:1. In embodiments, the RNA sequence has 80% sequence identity to the complement of at least 40 consecutive nucleotides of nucleotides 1-147 of SEQ ID NO:1. In embodiments, the RNA sequence has 80% sequence identity to the complement of at least 45 consecutive nucleotides of nucleotides 1-147 of SEQ ID NO:1. In embodiments, the RNA sequence has 80% sequence identity to the complement of at least 50 consecutive nucleotides of nucleotides 1-147 of SEQ ID NO:1.

In embodiments, the RNA sequence has 80% sequence identity to the complement of 15 consecutive nucleotides of nucleotides 1-147 of SEQ ID NO:1. In embodiments, the RNA sequence has 80% sequence identity to the complement of 16 consecutive nucleotides of nucleotides 1-147 of SEQ ID NO:1. In embodiments, the RNA sequence has 80% sequence identity to the complement of 17 consecutive nucleotides of nucleotides 1-147 of SEQ ID NO:1. In embodiments, the RNA sequence has 80% sequence identity to the complement of 18 consecutive nucleotides of nucleotides 1-147 of SEQ ID NO:1. In embodiments, the RNA sequence has 80% sequence identity to the complement of 19 consecutive nucleotides of nucleotides 1-147 of SEQ ID NO:1. In embodiments, the RNA sequence has 80% sequence identity to the complement of 20 consecutive nucleotides of nucleotides 1-147 of SEQ ID NO:1. In embodiments, the RNA sequence has 80% sequence identity to the complement of 25 consecutive nucleotides of nucleotides 1-147 of SEQ ID NO:1. In embodiments, the RNA sequence has 80% sequence identity to the complement of 30 consecutive nucleotides of nucleotides 1-147 of SEQ ID NO:1. In embodiments, the RNA sequence has 80% sequence identity to the complement of 35 consecutive nucleotides of nucleotides 1-147 of SEQ ID NO:1. In embodiments, the RNA sequence has 80% sequence identity to the complement of 40 consecutive nucleotides of nucleotides 1-147 of SEQ ID NO:1. In embodiments, the RNA sequence has 80% sequence identity to the complement of 45 consecutive nucleotides of nucleotides 1-147 of SEQ ID NO:1. In embodiments, the RNA sequence has 80% sequence identity to the complement of 50 consecutive nucleotides of nucleotides 1-147 of SEQ ID NO:1.

The ribonucleic acid compounds provided herein may hybridize (bind) to a specific portion of the lncRNA promoter sequence (e.g., the sequence of SEQ ID NO:1). The portion may include nucleotides 1-147 of SEQ ID NO:1. Thus, in embodiments, the RNA sequence has at least 80% sequence identity to the complement of at least 15 consecutive nucleotides of nucleotides 1-147 of SEQ ID NO:1. In embodiments, the RNA sequence has at least 80% sequence identity to the complement of at least 15 consecutive nucleotides of nucleotides 2-147 of SEQ ID NO:1. In embodiments, the RNA sequence has at least 80% sequence identity to the complement of at least 15 consecutive nucleotides of nucleotides 3-147 of SEQ ID NO:1. In embodiments, the RNA sequence has at least 80% sequence identity to the complement of at least 15 consecutive nucleotides of nucleotides 4-147 of SEQ ID NO:1. In embodiments, the RNA sequence has at least 80% sequence identity to the complement of at least 15 consecutive nucleotides of nucleotides 5-147 of SEQ ID NO:1. In embodiments, the RNA sequence has at least 80% sequence identity to the complement of at least 15 consecutive nucleotides of nucleotides 6-147 of SEQ ID NO:1. In embodiments, the RNA sequence has at least 80% sequence identity to the complement of at least 15 consecutive nucleotides of nucleotides 7-147 of SEQ ID NO:1. In embodiments, the RNA sequence has at least 80% sequence identity to the complement of at least 15 consecutive nucleotides of nucleotides 8-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24, or 25) consecutive nucleotides of nucleotides 1-147, 2-147, 3-147, 4-147, 5-147, 6-147, 7-147, or 8-147 of SEQ ID NO:1.

In embodiments, the RNA sequence has at least 80% sequence identity to the complement of at least 15 consecutive nucleotides of nucleotides 9-147 of SEQ ID NO:1. In embodiments, the RNA sequence has at least 80% sequence identity to the complement of at least 15 consecutive nucleotides of nucleotides 10-147 of SEQ ID NO:1. In embodiments, the RNA sequence has at least 80% sequence identity to the complement of at least 15 consecutive nucleotides of nucleotides 11-147 of SEQ ID NO:1. In embodiments, the RNA sequence has at least 80% sequence identity to the complement of at least 15 consecutive nucleotides of nucleotides 12-147 of SEQ ID NO:1. In embodiments, the RNA sequence has at least 80% sequence identity to the complement of at least 15 consecutive nucleotides of nucleotides 13-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24, or 25) consecutive nucleotides of nucleotides 9-147, 10-147, 11-147, 12-147, or 13-147 of SEQ ID NO:1.

In embodiments, the RNA sequence has at least 80% sequence identity to the complement of at least 15 consecutive nucleotides of nucleotides 14-147 of SEQ ID NO:1. In embodiments, the RNA sequence has at least 80% sequence identity to the complement of at least 15 consecutive nucleotides of nucleotides 15-147 of SEQ ID NO:1. In embodiments, the RNA sequence has at least 80% sequence identity to the complement of at least 15 consecutive nucleotides of nucleotides 16-147 of SEQ ID NO:1. In embodiments, the RNA sequence has at least 80% sequence identity to the complement of at least 15 consecutive nucleotides of nucleotides 17-147 of SEQ ID NO:1. In embodiments, the RNA sequence has at least 80% sequence identity to the complement of at least 15 consecutive nucleotides of nucleotides 18-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24, or 25) consecutive nucleotides of nucleotides 14-147, 15-147, 16-147, 17-147, or 18-147 of SEQ ID NO:1.

In embodiments, the RNA sequence has at least 80% sequence identity to the complement of at least 15 consecutive nucleotides of nucleotides 19-147 of SEQ ID NO:1. In embodiments, the RNA sequence has at least 80% sequence identity to the complement of at least 15 consecutive nucleotides of nucleotides 20-147 of SEQ ID NO:1. In embodiments, the RNA sequence has at least 80% sequence identity to the complement of at least 15 consecutive nucleotides of nucleotides 21-147 of SEQ ID NO:1. In embodiments, the RNA sequence has at least 80% sequence identity to the complement of at least 15 consecutive nucleotides of nucleotides 22-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 19-147, 20-147, 21-147, or 22-147 of SEQ ID NO:1.

In embodiments, the RNA sequence has at least 80% sequence identity to the complement of at least 15 consecutive nucleotides of nucleotides 23-147 of SEQ ID NO:1. In embodiments, the RNA sequence has at least 80% sequence identity to the complement of at least 15 consecutive nucleotides of nucleotides 24-147 of SEQ ID NO:1. In embodiments, the RNA sequence has at least 80% sequence identity to the complement of at least 15 consecutive nucleotides of nucleotides 25-147 of SEQ ID NO:1. In embodiments, the RNA sequence has at least 80% sequence identity to the complement of at least 15 consecutive nucleotides of nucleotides 26-147 of SEQ ID NO:1. In embodiments, the RNA sequence has at least 80% sequence identity to the complement of at least 15 consecutive nucleotides of nucleotides 27-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 23-147, 24-147, 25-147, 26-147, or 27-147 of SEQ ID NO:1.

In embodiments, the RNA sequence has at least 80% sequence identity to the complement of at least 15 consecutive nucleotides of nucleotides 28-147 of SEQ ID NO:1. In embodiments, the RNA sequence has at least 80% sequence identity to the complement of at least 15 consecutive nucleotides of nucleotides 29-147 of SEQ ID NO:1. In embodiments, the RNA sequence has at least 80% sequence identity to the complement of at least 15 consecutive nucleotides of nucleotides 30-147 of SEQ ID NO:1. In embodiments, the RNA sequence has at least 80% sequence identity to the complement of at least 15 consecutive nucleotides of nucleotides 31-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 28-147, 29-147, 30-147, or 31-147 above of SEQ ID NO:1.

In embodiments, the RNA sequence has at least 80% sequence identity to the complement of at least 15 consecutive nucleotides of nucleotides 32-147 of SEQ ID NO:1. In embodiments, the RNA sequence has at least 80% sequence identity to the complement of at least 15 consecutive nucleotides of nucleotides 33-147 of SEQ ID NO:1. In embodiments, the RNA sequence has at least 80% sequence identity to the complement of at least 15 consecutive nucleotides of nucleotides 34-147 of SEQ ID NO:1. In embodiments, the RNA sequence has at least 80% sequence identity to the complement of at least 15 consecutive nucleotides of nucleotides 35-147 of SEQ ID NO:1. In embodiments, the RNA sequence has at least 80% sequence identity to the complement of at least 15 consecutive nucleotides of nucleotides 36-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 32-147, 33-147, 34-147, 35-147, or 36-147 of SEQ ID NO:1.

In embodiments, the RNA sequence has at least 80% sequence identity to the complement of at least 15 consecutive nucleotides of nucleotides 37-147 of SEQ ID NO:1. In embodiments, the RNA sequence has at least 80% sequence identity to the complement of at least 15 consecutive nucleotides of nucleotides 38-147 of SEQ ID NO:1. In embodiments, the RNA sequence has at least 80% sequence identity to the complement of at least 15 consecutive nucleotides of nucleotides 39-147 of SEQ ID NO:1. In embodiments, the RNA sequence has at least 80% sequence identity to the complement of at least 15 consecutive nucleotides of nucleotides 40-147 of SEQ ID NO:1. In embodiments, the RNA sequence has at least 80% sequence identity to the complement of at least 15 consecutive nucleotides of nucleotides 41-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 37-147, 38-147, 39-147, 40-147, or 41-147 of SEQ ID NO:1.

In embodiments, the RNA sequence has at least 80% sequence identity to the complement of at least 15 consecutive nucleotides of nucleotides 42-147 of SEQ ID NO:1. In embodiments, the RNA sequence has at least 80% sequence identity to the complement of at least 15 consecutive nucleotides of nucleotides 43-147 of SEQ ID NO:1. In embodiments, the RNA sequence has at least 80% sequence identity to the complement of at least 15 consecutive nucleotides of nucleotides 44-147 of SEQ ID NO:1. In embodiments, the RNA sequence has at least 80% sequence identity to the complement of at least 15 consecutive nucleotides of nucleotides 45-147 of SEQ ID NO:1. In embodiments, the RNA sequence has at least 80% sequence identity to the complement of at least 15 consecutive nucleotides of nucleotides 46-147 of SEQ ID NO:1. In embodiments, the RNA sequence has at least 80% sequence identity to the complement of at least 15 consecutive nucleotides of nucleotides 47-147 of SEQ ID NO:1. In embodiments, the RNA sequence has at least 80% sequence identity to the complement of at least 15 consecutive nucleotides of nucleotides 48-147 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 42-147, 43-147, 44-147, 45-147, 46-147, 47-147, 48-147 of SEQ ID NO:1.

In embodiments, the RNA sequence has at least 80% sequence identity to the complement of at least 15 consecutive nucleotides of nucleotides 1-147 of SEQ ID NO:1. In embodiments, the RNA sequence has at least 80% sequence identity to the complement of at least 15 consecutive nucleotides of nucleotides 1-146 of SEQ ID NO:1. In embodiments, the RNA sequence has at least 80% sequence identity to the complement of at least 15 consecutive nucleotides of nucleotides 1-145 of SEQ ID NO:1. In embodiments, the RNA sequence has at least 80% sequence identity to the complement of at least 15 consecutive nucleotides of nucleotides 1-144 of SEQ ID NO:1. In embodiments, the RNA sequence has at least 80% sequence identity to the complement of at least 15 consecutive nucleotides of nucleotides 1-143 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-147, 1-146, 1-145, 1-144, or 1-143 of SEQ ID NO:1.

In embodiments, the RNA sequence has at least 80% sequence identity to the complement of at least 15 consecutive nucleotides of nucleotides 1-142 of SEQ ID NO:1. In embodiments, the RNA sequence has at least 80% sequence identity to the complement of at least 15 consecutive nucleotides of nucleotides 1-141 of SEQ ID NO:1. In embodiments, the RNA sequence has at least 80% sequence identity to the complement of at least 15 consecutive nucleotides of nucleotides 1-140 of SEQ ID NO:1. In embodiments, the RNA sequence has at least 80% sequence identity to the complement of at least 15 consecutive nucleotides of nucleotides 1-139 of SEQ ID NO:1. For the above embodiments, the RNA sequence may have about 85%, 91%, 90%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-142, 1-141, 1-140, or 1-139 of SEQ ID NO:1.

In embodiments, the RNA sequence has at least 80% sequence identity to the complement of at least 15 consecutive nucleotides of nucleotides 1-138 of SEQ ID NO:1. In embodiments, the RNA sequence has at least 80% sequence identity to the complement of at least 15 consecutive nucleotides of nucleotides 1-137 of SEQ ID NO:1. In embodiments, the RNA sequence has at least 80% sequence identity to the complement of at least 15 consecutive nucleotides of nucleotides 1-136 of SEQ ID NO:1. In embodiments, the RNA sequence has at least 80% sequence identity to the complement of at least 15 consecutive nucleotides of nucleotides 1-135 of SEQ ID NO:1. In embodiments, the RNA sequence has at least 80% sequence identity to the complement of at least 15 consecutive nucleotides of nucleotides 1-134 of SEQ ID NO:1. In embodiments, the RNA sequence has at least 80% sequence identity to the complement of at least 15 consecutive nucleotides of nucleotides 1-133 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-138, 1-137, 1-136, 1-135, 1-134, or 1-133 of SEQ ID NO:1.

In embodiments, the RNA sequence has at least 80% sequence identity to the complement of at least 15 consecutive nucleotides of nucleotides 1-132 of SEQ ID NO:1. In embodiments, the RNA sequence has at least 80% sequence identity to the complement of at least 15 consecutive nucleotides of nucleotides 1-131 of SEQ ID NO:1. In embodiments, the RNA sequence has at least 80% sequence identity to the complement of at least 15 consecutive nucleotides of nucleotides 1-130 of SEQ ID NO:1. In embodiments, the RNA sequence has at least 80% sequence identity to the complement of at least 15 consecutive nucleotides of nucleotides 1-129 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-132, 1-131, 1-130, or 1-129 of SEQ ID NO:1.

In embodiments, the RNA sequence has at least 80% sequence identity to the complement of at least 15 consecutive nucleotides of nucleotides 1-128 of SEQ ID NO:1. In embodiments, the RNA sequence has at least 80% sequence identity to the complement of at least 15 consecutive nucleotides of nucleotides 1-127 of SEQ ID NO:1. In embodiments, the RNA sequence has at least 80% sequence identity to the complement of at least 15 consecutive nucleotides of nucleotides 1-126 of SEQ ID NO:1. In embodiments, the RNA sequence has at least 80% sequence identity to the complement of at least 15 consecutive nucleotides of nucleotides 1-125 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-128, 1-127, 1-126, or 1-125 of SEQ ID NO:1.

In embodiments, the RNA sequence has at least 80% sequence identity to the complement of at least 15 consecutive nucleotides of nucleotides 1-124 of SEQ ID NO:1. In embodiments, the RNA sequence has at least 80% sequence identity to the complement of at least 15 consecutive nucleotides of nucleotides 1-123 of SEQ ID NO:1. In embodiments, the RNA sequence has at least 80% sequence identity to the complement of at least 15 consecutive nucleotides of nucleotides 1-122 of SEQ ID NO:1. In embodiments, the RNA sequence has at least 80% sequence identity to the complement of at least 15 consecutive nucleotides of nucleotides 1-121 of SEQ ID NO:1. In embodiments, the RNA sequence has at least 80% sequence identity to the complement of at least 15 consecutive nucleotides of nucleotides 1-120 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-124, 1-123, 1-122, 1-121, or 1-120 of SEQ ID NO:1.

In embodiments, the RNA sequence has at least 80% sequence identity to the complement of at least 15 consecutive nucleotides of nucleotides 1-119 of SEQ ID NO:1. In embodiments, the RNA sequence has at least 80% sequence identity to the complement of at least 15 consecutive nucleotides of nucleotides 1-118 of SEQ ID NO:1. In embodiments, the RNA sequence has at least 80% sequence identity to the complement of at least 15 consecutive nucleotides of nucleotides 1-117 of SEQ ID NO:1. In embodiments, the RNA sequence has at least 80% sequence identity to the complement of at least 15 consecutive nucleotides of nucleotides 1-116 of SEQ ID NO:1. In embodiments, the RNA sequence has at least 80% sequence identity to the complement of at least 15 consecutive nucleotides of nucleotides 1-115 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-119, 1-118, 1-117, 1-116, or 1-115 of SEQ ID NO: 1.

In embodiments, the RNA sequence has at least 80% sequence identity to the complement of at least 15 consecutive nucleotides of nucleotides 1-114 of SEQ ID NO:1. In embodiments, the RNA sequence has at least 80% sequence identity to the complement of at least 15 consecutive nucleotides of nucleotides 1-113 of SEQ ID NO:1. In embodiments, the RNA sequence has at least 80% sequence identity to the complement of at least 15 consecutive nucleotides of nucleotides 1-112 of SEQ ID NO:1. In embodiments, the RNA sequence has at least 80% sequence identity to the complement of at least 15 consecutive nucleotides of nucleotides 1-111 of SEQ ID NO:1 For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-114, 1-113, 1-112, or 1-111 of SEQ ID NO:1.

In embodiments, the RNA sequence has at least 80% sequence identity to the complement of at least 15 consecutive nucleotides of nucleotides 1-110 of SEQ ID NO:1. In embodiments, the RNA sequence has at least 80% sequence identity to the complement of at least 15 consecutive nucleotides of nucleotides 1-109 of SEQ ID NO:1. In embodiments, the RNA sequence has at least 80% sequence identity to the complement of at least 15 consecutive nucleotides of nucleotides 1-108 of SEQ ID NO:1. In embodiments, the RNA sequence has at least 80% sequence identity to the complement of at least 15 consecutive nucleotides of nucleotides 1-107 of SEQ ID NO:1. In embodiments, the RNA sequence has at least 80% sequence identity to the complement of at least 15 consecutive nucleotides of nucleotides 1-106 of SEQ ID NO:1 For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-110, 1-109, 1-108, 1-107, or 1-106 of SEQ ID NO: 1.

In embodiments, the RNA sequence has at least 80% sequence identity to the complement of at least 15 consecutive nucleotides of nucleotides 1-105 of SEQ ID NO:1. In embodiments, the RNA sequence has at least 80% sequence identity to the complement of at least 15 consecutive nucleotides of nucleotides 1-104 of SEQ ID NO:1. In embodiments, the RNA sequence has at least 80% sequence identity to the complement of at least 15 consecutive nucleotides of nucleotides 1-103 of SEQ ID NO:1. In embodiments, the RNA sequence has at least 80% sequence identity to the complement of at least 15 consecutive nucleotides of nucleotides 1-102 of SEQ ID NO:1. In embodiments, the RNA sequence has at least 80% sequence identity to the complement of at least 15 consecutive nucleotides of nucleotides 1-101 of SEQ ID NO:1 For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-105, 1-104, 1-103, 1-102, or 1-101 of SEQ ID NO:1.

In embodiments, the RNA sequence has at least 80% sequence identity to the complement of at least 15 consecutive nucleotides of nucleotides 1-100 of SEQ ID NO:1. In embodiments, the RNA sequence has at least 80% sequence identity to the complement of at least 15 consecutive nucleotides of nucleotides 1-99 of SEQ ID NO:1. In embodiments, the RNA sequence has at least 80% sequence identity to the complement of at least 15 consecutive nucleotides of nucleotides 1-98 of SEQ ID NO:1. In embodiments, the RNA sequence has at least 80% sequence identity to the complement of at least 15 consecutive nucleotides of nucleotides 1-97 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-100, 1-99, 1-98, or 1-97 of SEQ ID NO:1.

In embodiments, the RNA sequence has at least 80% sequence identity to the complement of at least 15 consecutive nucleotides of nucleotides 1-96 of SEQ ID NO:1. In embodiments, the RNA sequence has at least 80% sequence identity to the complement of at least 15 consecutive nucleotides of nucleotides 1-95 of SEQ ID NO:1. In embodiments, the RNA sequence has at least 80% sequence identity to the complement of at least 15 consecutive nucleotides of nucleotides 1-94 of SEQ ID NO:1. In embodiments, the RNA sequence has at least 80% sequence identity to the complement of at least 15 consecutive nucleotides of nucleotides 1-93 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-96, 1-95, 1-94, or 1-93 of SEQ ID NO:1.

In embodiments, the RNA sequence has at least 80% sequence identity to the complement of at least 15 consecutive nucleotides of nucleotides 1-92 of SEQ ID NO:1. In embodiments, the RNA sequence has at least 80% sequence identity to the complement of at least 15 consecutive nucleotides of nucleotides 1-91 of SEQ ID NO:1. In embodiments, the RNA sequence has at least 80% sequence identity to the complement of at least 15 consecutive nucleotides of nucleotides 1-90 of SEQ ID NO:1. In embodiments, the RNA sequence has at least 80% sequence identity to the complement of at least 15 consecutive nucleotides of nucleotides 1-89 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-92, 1-91, 1-90, or 1-89 of SEQ ID NO:1.

In embodiments, the RNA sequence has at least 80% sequence identity to the complement of at least 15 consecutive nucleotides of nucleotides 1-88 of SEQ ID NO:1. In embodiments, the RNA sequence has at least 80% sequence identity to the complement of at least 15 consecutive nucleotides of nucleotides 1-87 of SEQ ID NO:1. In embodiments, the RNA sequence has at least 80% sequence identity to the complement of at least 15 consecutive nucleotides of nucleotides 1-86 of SEQ ID NO:1. In embodiments, the RNA sequence has at least 80% sequence identity to the complement of at least 15 consecutive nucleotides of nucleotides 1-85 of SEQ ID NO:1. In embodiments, the RNA sequence has at least 80% sequence identity to the complement of at least 15 consecutive nucleotides of nucleotides 1-84 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-88, 1-87, 1-86, 1-85, or 1-84 of SEQ ID NO:1.

In embodiments, the RNA sequence has at least 80% sequence identity to the complement of at least 15 consecutive nucleotides of nucleotides 1-83 of SEQ ID NO:1. In embodiments, the RNA sequence has at least 80% sequence identity to the complement of at least 15 consecutive nucleotides of nucleotides 1-82 of SEQ ID NO:1. In embodiments, the RNA sequence has at least 80% sequence identity to the complement of at least 15 consecutive nucleotides of nucleotides 1-81 of SEQ ID NO:1. In embodiments, the RNA sequence has at least 80% sequence identity to the complement of at least 15 consecutive nucleotides of nucleotides 1-80 of SEQ ID NO:1. In embodiments, the RNA sequence has at least 80% sequence identity to the complement of at least 15 consecutive nucleotides of nucleotides 1-79 of SEQ ID NO:1. In embodiments, the RNA sequence has at least 80% sequence identity to the complement of at least 15 consecutive nucleotides of nucleotides 1-78 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-83, 1-82, 1-81, 1-80, 1-79, or 1-78 of SEQ ID NO:1.

In embodiments, the RNA sequence has at least 80% sequence identity to the complement of at least 15 consecutive nucleotides of nucleotides 1-77 of SEQ ID NO:1. In embodiments, the RNA sequence has at least 80% sequence identity to the complement of at least 15 consecutive nucleotides of nucleotides 1-76 of SEQ ID NO:1. In embodiments, the RNA sequence has at least 80% sequence identity to the complement of at least 15 consecutive nucleotides of nucleotides 1-75 of SEQ ID NO:1. In embodiments, the RNA sequence has at least 80% sequence identity to the complement of at least 15 consecutive nucleotides of nucleotides 1-74 of SEQ ID NO:1. In embodiments, the RNA sequence has at least 80% sequence identity to the complement of at least 15 consecutive nucleotides of nucleotides 1-73 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-77, 1-76, 1-75, 1-74, or 1-73 of SEQ ID NO:1.

In embodiments, the RNA sequence has at least 80% sequence identity to the complement of at least 15 consecutive nucleotides of nucleotides 1-72 of SEQ ID NO:1. In embodiments, the RNA sequence has at least 80% sequence identity to the complement of at least 15 consecutive nucleotides of nucleotides 1-71 of SEQ ID NO:1. In embodiments, the RNA sequence has at least 80% sequence identity to the complement of at least 15 consecutive nucleotides of nucleotides 1-70 of SEQ ID NO:1. In embodiments, the RNA sequence has at least 80% sequence identity to the complement of at least 15 consecutive nucleotides of nucleotides 1-69 of SEQ ID NO:1. In embodiments, the RNA sequence has at least 80% sequence identity to the complement of at least 15 consecutive nucleotides of nucleotides 1-68 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-72, 1-71, 1-70, 1-69, or 1-68 of SEQ ID NO:1.

In embodiments, the RNA sequence has at least 80% sequence identity to the complement of at least 15 consecutive nucleotides of nucleotides 1-67 of SEQ ID NO:1. In embodiments, the RNA sequence has at least 80% sequence identity to the complement of at least 15 consecutive nucleotides of nucleotides 1-66 of SEQ ID NO:1. In embodiments, the RNA sequence has at least 80% sequence identity to the complement of at least 15 consecutive nucleotides of nucleotides 1-65 of SEQ ID NO:1. In embodiments, the RNA sequence has at least 80% sequence identity to the complement of at least 15 consecutive nucleotides of nucleotides 1-64 of SEQ ID NO:1. In embodiments, the RNA sequence has at least 80% sequence identity to the complement of at least 15 consecutive nucleotides of nucleotides 1-63 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-67, 1-66, 1-65, 1-64, or 1-63 of SEQ ID NO:1.

In embodiments, the RNA sequence has at least 80% sequence identity to the complement of at least 15 consecutive nucleotides of nucleotides 1-62 of SEQ ID NO:1. In embodiments, the RNA sequence has at least 80% sequence identity to the complement of at least 15 consecutive nucleotides of nucleotides 1-61 of SEQ ID NO:1. In embodiments, the RNA sequence has at least 80% sequence identity to the complement of at least 15 consecutive nucleotides of nucleotides 1-60 of SEQ ID NO:1. In embodiments, the RNA sequence has at least 80% sequence identity to the complement of at least 15 consecutive nucleotides of nucleotides 1-59 of SEQ ID NO:1. In embodiments, the RNA sequence has at least 80% sequence identity to the complement of at least 15 consecutive nucleotides of nucleotides 1-58 of SEQ ID NO:1. In embodiments, the RNA sequence has at least 80% sequence identity to the complement of at least 15 consecutive nucleotides of nucleotides 1-57 of SEQ ID NO:1. In embodiments, the RNA sequence has at least 80% sequence identity to the complement of at least 15 consecutive nucleotides of nucleotides 1-56 of SEQ ID NO:1. In embodiments, the RNA sequence has at least 80% sequence identity to the complement of at least 15 consecutive nucleotides of nucleotides 1-55 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-62, 1-61, 1-60, 1-59, 1-58, 1-57, 1-56, or 1-55 of SEQ ID NO:1.

In embodiments, the RNA sequence has at least 80% sequence identity to the complement of at least 15 consecutive nucleotides of nucleotides 1-54 of SEQ ID NO:1. In embodiments, the RNA sequence has at least 80% sequence identity to the complement of at least 15 consecutive nucleotides of nucleotides 1-53 of SEQ ID NO:1. In embodiments, the RNA sequence has at least 80% sequence identity to the complement of at least 15 consecutive nucleotides of nucleotides 1-52 of SEQ ID NO:1. In embodiments, the RNA sequence has at least 80% sequence identity to the complement of at least 15 consecutive nucleotides of nucleotides 1-51 of SEQ ID NO:1. In embodiments, the RNA sequence has at least 80% sequence identity to the complement of at least 15 consecutive nucleotides of nucleotides 1-50 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-54, 1-53, 1-52, 1-51, or 1-50 of SEQ ID NO:1.

In embodiments, the RNA sequence has at least 80% sequence identity to the complement of at least 15 consecutive nucleotides of nucleotides 1-49 of SEQ ID NO:1. In embodiments, the RNA sequence has at least 80% sequence identity to the complement of at least 15 consecutive nucleotides of nucleotides 1-48 of SEQ ID NO:1. In embodiments, the RNA sequence has at least 80% sequence identity to the complement of at least 15 consecutive nucleotides of nucleotides 1-47 of SEQ ID NO:1. In embodiments, the RNA sequence has at least 80% sequence identity to the complement of at least 15 consecutive nucleotides of nucleotides 1-46 of SEQ ID NO:1. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-49, 1-48, 1-47, or 1-46 of SEQ ID NO:1.

In embodiments, the RNA sequence hybridizes to nucleotides 27-47 of SEQ ID NO:1. In embodiments, the RNA sequence hybridizes to nucleotides 133-153 of SEQ ID NO:1. In embodiments, the RNA sequence hybridizes to nucleotides 169-189 of SEQ ID NO:1. In embodiments, the RNA sequence hybridizes to nucleotides 194-217 of SEQ ID NO:1. In embodiments, the RNA sequence hybridizes to nucleotides 281-301 of SEQ ID NO:1.

In embodiments, the RNA sequence has at least 90% sequence identity to the complement of at least 15 consecutive nucleotides of nucleotides 27-47 of SEQ ID NO:1. In embodiments, the RNA sequence has at least 90% sequence identity to the complement of at least 15 consecutive nucleotides of nucleotides 25-47 of SEQ ID NO:1. In embodiments, the RNA sequence has at least 90% sequence identity to the complement of at least 15 consecutive nucleotides of nucleotides 23-47 of SEQ ID NO:1. In embodiments, the RNA sequence has at least 90% sequence identity to the complement of at least 15 consecutive nucleotides of nucleotides 21-47 of SEQ ID NO:1. In embodiments, the RNA sequence has at least 90% sequence identity to the complement of at least 15 consecutive nucleotides of nucleotides 19-47 of SEQ ID NO:1. In embodiments, the RNA sequence has at least 90% sequence identity to the complement of at least 15 consecutive nucleotides of nucleotides 17-47 of SEQ ID NO:1. In embodiments, the RNA sequence has at least 90% sequence identity to the complement of at least 15 consecutive nucleotides of nucleotides 15-47 of SEQ ID NO:1. In embodiments, the RNA sequence has at least 90% sequence identity to the complement of at least 15 consecutive nucleotides of nucleotides 13-47 of SEQ ID NO:1. In embodiments, the RNA sequence has at least 90% sequence identity to the complement of at least 15 consecutive nucleotides of nucleotides 11-47 of SEQ ID NO:1.

In embodiments, the RNA sequence has at least 90% sequence identity to the complement of at least 15 consecutive nucleotides of nucleotides 27-49 of SEQ ID NO:1. In embodiments, the RNA sequence has at least 90% sequence identity to the complement of at least 15 consecutive nucleotides of nucleotides 27-51 of SEQ ID NO:1. In embodiments, the RNA sequence has at least 90% sequence identity to the complement of at least 15 consecutive nucleotides of nucleotides 27-53 of SEQ ID NO:1. In embodiments, the RNA sequence has at least 90% sequence identity to the complement of at least 15 consecutive nucleotides of nucleotides 27-55 of SEQ ID NO:1. In embodiments, the RNA sequence has at least 90% sequence identity to the complement of at least 15 consecutive nucleotides of nucleotides 27-57 of SEQ ID NO:1. In embodiments, the RNA sequence has at least 90% sequence identity to the complement of at least 15 consecutive nucleotides of nucleotides 27-59 of SEQ ID NO:1. In embodiments, the RNA sequence has at least 90% sequence identity to the complement of at least 15 consecutive nucleotides of nucleotides 27-61 of SEQ ID NO:1. In embodiments, the RNA sequence has at least 90% sequence identity to the complement of at least 15 consecutive nucleotides of nucleotides 27-63 of SEQ ID NO:1. In embodiments, the RNA sequence has at least 90% sequence identity to the complement of at least 15 consecutive nucleotides of nucleotides 27-65 of SEQ ID NO:1.

In embodiments, the RNA sequence has at least 97% sequence identity to the complement of at least 15 consecutive nucleotides of nucleotides 27-47 of SEQ ID NO:1. In embodiments, the RNA sequence has at least 97% sequence identity to the complement of at least 15 consecutive nucleotides of nucleotides 25-47 of SEQ ID NO:1. In embodiments, the RNA sequence has at least 97% sequence identity to the complement of at least 15 consecutive nucleotides of nucleotides 23-47 of SEQ ID NO:1. In embodiments, the RNA sequence has at least 97% sequence identity to the complement of at least 15 consecutive nucleotides of nucleotides 21-47 of SEQ ID NO:1. In embodiments, the RNA sequence has at least 97% sequence identity to the complement of at least 15 consecutive nucleotides of nucleotides 19-47 of SEQ ID NO:1. In embodiments, the RNA sequence has at least 97% sequence identity to the complement of at least 15 consecutive nucleotides of nucleotides 17-47 of SEQ ID NO:1. In embodiments, the RNA sequence has at least 97% sequence identity to the complement of at least 15 consecutive nucleotides of nucleotides 15-47 of SEQ ID NO:1. In embodiments, the RNA sequence has at least 97% sequence identity to the complement of at least 15 consecutive nucleotides of nucleotides 13-47 of SEQ ID NO:1. In embodiments, the RNA sequence has at least 97% sequence identity to the complement of at least 15 consecutive nucleotides of nucleotides 11-47 of SEQ ID NO:1.

In embodiments, the RNA sequence has at least 97% sequence identity to the complement of at least 15 consecutive nucleotides of nucleotides 27-49 of SEQ ID NO:1. In embodiments, the RNA sequence has at least 97% sequence identity to the complement of at least 15 consecutive nucleotides of nucleotides 27-51 of SEQ ID NO:1. In embodiments, the RNA sequence has at least 97% sequence identity to the complement of at least 15 consecutive nucleotides of nucleotides 27-53 of SEQ ID NO:1. In embodiments, the RNA sequence has at least 97% sequence identity to the complement of at least 15 consecutive nucleotides of nucleotides 27-55 of SEQ ID NO:1. In embodiments, the RNA sequence has at least 97% sequence identity to the complement of at least 15 consecutive nucleotides of nucleotides 27-57 of SEQ ID NO:1. In embodiments, the RNA sequence has at least 97% sequence identity to the complement of at least 15 consecutive nucleotides of nucleotides 27-59 of SEQ ID NO:1. In embodiments, the RNA sequence has at least 97% sequence identity to the complement of at least 15 consecutive nucleotides of nucleotides 27-61 of SEQ ID NO:1. In embodiments, the RNA sequence has at least 97% sequence identity to the complement of at least 15 consecutive nucleotides of nucleotides 27-63 of SEQ ID NO:1. In embodiments, the RNA sequence has at least 97% sequence identity to the complement of at least 15 consecutive nucleotides of nucleotides 27-65 of SEQ ID NO:1.

In embodiments, the RNA sequence has at least 90% sequence identity to the complement of at least 15 consecutive nucleotides of nucleotides 133-153 of SEQ ID NO:1. In embodiments, the RNA sequence has at least 90% sequence identity to the complement of at least 15 consecutive nucleotides of nucleotides 130-153 of SEQ ID NO:1. In embodiments, the RNA sequence has at least 90% sequence identity to the complement of at least 15 consecutive nucleotides of nucleotides 125-153 of SEQ ID NO:1. In embodiments, the RNA sequence has at least 90% sequence identity to the complement of at least 15 consecutive nucleotides of nucleotides 120-153 of SEQ ID NO:1.

In embodiments, the RNA sequence has at least 90% sequence identity to the complement of at least 15 consecutive nucleotides of nucleotides 133-155 of SEQ ID NO:1. In embodiments, the RNA sequence has at least 90% sequence identity to the complement of at least 15 consecutive nucleotides of nucleotides 133-160 of SEQ ID NO:1. In embodiments, the RNA sequence has at least 90% sequence identity to the complement of at least 15 consecutive nucleotides of nucleotides 133-165 of SEQ ID NO:1. In embodiments, the RNA sequence has at least 90% sequence identity to the complement of at least 15 consecutive nucleotides of nucleotides 133-170 of SEQ ID NO:1.

In embodiments, the RNA sequence has at least 97% sequence identity to the complement of at least 15 consecutive nucleotides of nucleotides 133-153 of SEQ ID NO:1. In embodiments, the RNA sequence has at least 97% sequence identity to the complement of at least 15 consecutive nucleotides of nucleotides 130-153 of SEQ ID NO:1. In embodiments, the RNA sequence has at least 97% sequence identity to the complement of at least 15 consecutive nucleotides of nucleotides 125-153 of SEQ ID NO:1. In embodiments, the RNA sequence has at least 97% sequence identity to the complement of at least 15 consecutive nucleotides of nucleotides 120-153 of SEQ ID NO:1.

In embodiments, the RNA sequence has at least 97% sequence identity to the complement of at least 15 consecutive nucleotides of nucleotides 133-155 of SEQ ID NO:1. In embodiments, the RNA sequence has at least 97% sequence identity to the complement of at least 15 consecutive nucleotides of nucleotides 133-160 of SEQ ID NO:1. In embodiments, the RNA sequence has at least 97% sequence identity to the complement of at least 15 consecutive nucleotides of nucleotides 133-165 of SEQ ID NO:1. In embodiments, the RNA sequence has at least 97% sequence identity to the complement of at least 15 consecutive nucleotides of nucleotides 133-170 of SEQ ID NO:1.

In embodiments, the RNA sequence has at least 90% sequence identity to the complement of at least 15 consecutive nucleotides of nucleotides 169-189 of SEQ ID NO:1. In embodiments, the RNA sequence has at least 90% sequence identity to the complement of at least 15 consecutive nucleotides of nucleotides 165-189 of SEQ ID NO:1. In embodiments, the RNA sequence has at least 90% sequence identity to the complement of at least 15 consecutive nucleotides of nucleotides 160-189 of SEQ ID NO:1. In embodiments, the RNA sequence has at least 90% sequence identity to the complement of at least 15 consecutive nucleotides of nucleotides 155-189 of SEQ ID NO:1. In embodiments, the RNA sequence has at least 90% sequence identity to the complement of at least 15 consecutive nucleotides of nucleotides 150-189 of SEQ ID NO:1.

In embodiments, the RNA sequence has at least 90% sequence identity to the complement of at least 15 consecutive nucleotides of nucleotides 169-190 of SEQ ID NO:1. In embodiments, the RNA sequence has at least 90% sequence identity to the complement of at least 15 consecutive nucleotides of nucleotides 169-195 of SEQ ID NO:1. In embodiments, the RNA sequence has at least 90% sequence identity to the complement of at least 15 consecutive nucleotides of nucleotides 169-200 of SEQ ID NO:1. In embodiments, the RNA sequence has at least 90% sequence identity to the complement of at least 15 consecutive nucleotides of nucleotides 169-205 of SEQ ID NO:1. In embodiments, the RNA sequence has at least 90% sequence identity to the complement of at least 15 consecutive nucleotides of nucleotides 169-210 of SEQ ID NO:1.

In embodiments, the RNA sequence has at least 97% sequence identity to the complement of at least 15 consecutive nucleotides of nucleotides 169-189 of SEQ ID NO:1. In embodiments, the RNA sequence has at least 97% sequence identity to the complement of at least 15 consecutive nucleotides of nucleotides 165-189 of SEQ ID NO:1. In embodiments, the RNA sequence has at least 97% sequence identity to the complement of at least 15 consecutive nucleotides of nucleotides 160-189 of SEQ ID NO:1. In embodiments, the RNA sequence has at least 97% sequence identity to the complement of at least 15 consecutive nucleotides of nucleotides 155-189 of SEQ ID NO:1. In embodiments, the RNA sequence has at least 97% sequence identity to the complement of at least 15 consecutive nucleotides of nucleotides 150-189 of SEQ ID NO:1.

In embodiments, the RNA sequence has at least 97% sequence identity to the complement of at least 15 consecutive nucleotides of nucleotides 169-190 of SEQ ID NO:1. In embodiments, the RNA sequence has at least 97% sequence identity to the complement of at least 15 consecutive nucleotides of nucleotides 169-195 of SEQ ID NO:1. In embodiments, the RNA sequence has at least 97% sequence identity to the complement of at least 15 consecutive nucleotides of nucleotides 169-200 of SEQ ID NO:1. In embodiments, the RNA sequence has at least 97% sequence identity to the complement of at least 15 consecutive nucleotides of nucleotides 169-205 of SEQ ID NO:1. In embodiments, the RNA sequence has at least 97% sequence identity to the complement of at least 15 consecutive nucleotides of nucleotides 169-210 of SEQ ID NO: 1.

In embodiments, the RNA sequence has at least 90% sequence identity to the complement of at least 15 consecutive nucleotides of nucleotides 194-217 of SEQ ID NO:1. In embodiments, the RNA sequence has at least 90% sequence identity to the complement of at least 15 consecutive nucleotides of nucleotides 190-217 of SEQ ID NO:1. In embodiments, the RNA sequence has at least 90% sequence identity to the complement of at least 15 consecutive nucleotides of nucleotides 185-217 of SEQ ID NO:1. In embodiments, the RNA sequence has at least 90% sequence identity to the complement of at least 15 consecutive nucleotides of nucleotides 180-217 of SEQ ID NO:1. In embodiments, the RNA sequence has at least 90% sequence identity to the complement of at least 15 consecutive nucleotides of nucleotides 175-217 of SEQ ID NO:1. In embodiments, the RNA sequence has at least 90% sequence identity to the complement of at least 15 consecutive nucleotides of nucleotides 170-217 of SEQ ID NO:1.

In embodiments, the RNA sequence has at least 90% sequence identity to the complement of at least 15 consecutive nucleotides of nucleotides 194-220 of SEQ ID NO:1. In embodiments, the RNA sequence has at least 90% sequence identity to the complement of at least 15 consecutive nucleotides of nucleotides 194-225 of SEQ ID NO:1. In embodiments, the RNA sequence has at least 90% sequence identity to the complement of at least 15 consecutive nucleotides of nucleotides 194-230 of SEQ ID NO:1. In embodiments, the RNA sequence has at least 90% sequence identity to the complement of at least 15 consecutive nucleotides of nucleotides 194-235 of SEQ ID NO:1. In embodiments, the RNA sequence has at least 90% sequence identity to the complement of at least 15 consecutive nucleotides of nucleotides 194-240 of SEQ ID NO:1. In embodiments, the RNA sequence has at least 90% sequence identity to the complement of at least 15 consecutive nucleotides of nucleotides 194-245 of SEQ ID NO:1.

In embodiments, the RNA sequence has at least 97% sequence identity to the complement of at least 15 consecutive nucleotides of nucleotides 194-217 of SEQ ID NO:1. In embodiments, the RNA sequence has at least 97% sequence identity to the complement of at least 15 consecutive nucleotides of nucleotides 190-217 of SEQ ID NO:1. In embodiments, the RNA sequence has at least 97% sequence identity to the complement of at least 15 consecutive nucleotides of nucleotides 185-217 of SEQ ID NO:1. In embodiments, the RNA sequence has at least 97% sequence identity to the complement of at least 15 consecutive nucleotides of nucleotides 180-217 of SEQ ID NO:1. In embodiments, the RNA sequence has at least 97% sequence identity to the complement of at least 15 consecutive nucleotides of nucleotides 175-217 of SEQ ID NO:1. In embodiments, the RNA sequence has at least 97% sequence identity to the complement of at least 15 consecutive nucleotides of nucleotides 170-217 of SEQ ID NO:1.

In embodiments, the RNA sequence has at least 97% sequence identity to the complement of at least 15 consecutive nucleotides of nucleotides 194-220 of SEQ ID NO:1. In embodiments, the RNA sequence has at least 97% sequence identity to the complement of at least 15 consecutive nucleotides of nucleotides 194-225 of SEQ ID NO:1. In embodiments, the RNA sequence has at least 97% sequence identity to the complement of at least 15 consecutive nucleotides of nucleotides 194-230 of SEQ ID NO:1. In embodiments, the RNA sequence has at least 97% sequence identity to the complement of at least 15 consecutive nucleotides of nucleotides 194-235 of SEQ ID NO:1. In embodiments, the RNA sequence has at least 97% sequence identity to the complement of at least 15 consecutive nucleotides of nucleotides 194-240 of SEQ ID NO:1. In embodiments, the RNA sequence has at least 97% sequence identity to the complement of at least 15 consecutive nucleotides of nucleotides 194-245 of SEQ ID NO:1.

In embodiments, the RNA sequence has at least 90% sequence identity to the complement of at least 15 consecutive nucleotides of nucleotides 281-301 of SEQ ID NO:1. In embodiments, the RNA sequence has at least 90% sequence identity to the complement of at least 15 consecutive nucleotides of nucleotides 281-305 of SEQ ID NO:1. In embodiments, the RNA sequence has at least 90% sequence identity to the complement of at least 15 consecutive nucleotides of nucleotides 281-310 of SEQ ID NO:1. In embodiments, the RNA sequence has at least 90% sequence identity to the complement of at least 15 consecutive nucleotides of nucleotides 281-315 of SEQ ID NO:1.

In embodiments, the RNA sequence has at least 90% sequence identity to the complement of at least 15 consecutive nucleotides of nucleotides 275-301 of SEQ ID NO:1. In embodiments, the RNA sequence has at least 90% sequence identity to the complement of at least 15 consecutive nucleotides of nucleotides 270-301 of SEQ ID NO:1. In embodiments, the RNA sequence has at least 90% sequence identity to the complement of at least 15 consecutive nucleotides of nucleotides 265-301 of SEQ ID NO:1. In embodiments, the RNA sequence has at least 90% sequence identity to the complement of at least 15 consecutive nucleotides of nucleotides 260-301 of SEQ ID NO:1.

In embodiments, the RNA sequence has at least 97% sequence identity to the complement of at least 15 consecutive nucleotides of nucleotides 281-301 of SEQ ID NO:1. In embodiments, the RNA sequence has at least 97% sequence identity to the complement of at least 15 consecutive nucleotides of nucleotides 281-305 of SEQ ID NO:1. In embodiments, the RNA sequence has at least 97% sequence identity to the complement of at least 15 consecutive nucleotides of nucleotides 281-310 of SEQ ID NO:1. In embodiments, the RNA sequence has at least 97% sequence identity to the complement of at least 15 consecutive nucleotides of nucleotides 281-315 of SEQ ID NO:1.

In embodiments, the RNA sequence has at least 97% sequence identity to the complement of at least 15 consecutive nucleotides of nucleotides 275-301 of SEQ ID NO:1. In embodiments, the RNA sequence has at least 97% sequence identity to the complement of at least 15 consecutive nucleotides of nucleotides 270-301 of SEQ ID NO:1. In embodiments, the RNA sequence has at least 97% sequence identity to the complement of at least 15 consecutive nucleotides of nucleotides 265-301 of SEQ ID NO:1. In embodiments, the RNA sequence has at least 97% sequence identity to the complement of at least 15 consecutive nucleotides of nucleotides 260-301 of SEQ ID NO:1.

The ribonucleic acid compounds as described herein including embodiments thereof, are composed of nucleotides capable of forming base pairs with a target RNA (e.g, lncRNA or lncRNA promoter sequence). Thus, the ribonucleic nucleic acid compounds described herein including embodiments thereof, are complementary to the target RNA (lncRNA or lncRNA promoter sequence) and can bind (hybridize) with portions of the target RNA sequence. In embodiments, the RNA sequence is capable of hybridizing to at least 15 (e.g., 16, 17, 18, 19, 20, 21, 22, 23, 24, 25, 30, 35, 40, 45, or 50) consecutive nucleotides of nucleotides 1-147 of SEQ ID NO:1. In embodiments, the RNA sequence is capable of hybridizing to 15 consecutive nucleotides of nucleotides 1-147 of SEQ ID NO:1. In embodiments, the RNA sequence is capable of hybridizing to 16 consecutive nucleotides of nucleotides 1-147 of SEQ ID NO:1. In embodiments, the RNA sequence is capable of hybridizing to 17 consecutive nucleotides of nucleotides 1-147 of SEQ ID NO:1. In embodiments, the RNA sequence is capable of hybridizing to 18 consecutive nucleotides of nucleotides 1-147 of SEQ ID NO:1. In embodiments, the RNA sequence is capable of hybridizing to 19 consecutive nucleotides of nucleotides 1-147 of SEQ ID NO:1. In embodiments, the RNA sequence is capable of hybridizing to 20 consecutive nucleotides of nucleotides 1-147 of SEQ ID NO:1. In embodiments, the RNA sequence is capable of hybridizing to 21 consecutive nucleotides of nucleotides 1-147 of SEQ ID NO:1. In embodiments, the RNA sequence is capable of hybridizing to 22 consecutive nucleotides of nucleotides 1-147 of SEQ ID NO:1. In embodiments, the RNA sequence is capable of hybridizing to 23 consecutive nucleotides of nucleotides 1-147 of SEQ ID NO:1. In embodiments, the RNA sequence is capable of hybridizing to 24 consecutive nucleotides of nucleotides 1-147 of SEQ ID NO:1. In embodiments, the RNA sequence is capable of hybridizing to 25 consecutive nucleotides of nucleotides 1-147 of SEQ ID NO:1. In embodiments, the RNA sequence is capable of hybridizing to 26 consecutive nucleotides of nucleotides 1-147 of SEQ ID NO:1. In embodiments, the RNA sequence is capable of hybridizing to 27 consecutive nucleotides of nucleotides 1-147 of SEQ ID NO:1. In embodiments, the RNA sequence is capable of hybridizing to 28 consecutive nucleotides of nucleotides 1-147 of SEQ ID NO:1. In embodiments, the RNA sequence is capable of hybridizing to 29 consecutive nucleotides of nucleotides 1-147 of SEQ ID NO:1. In embodiments, the RNA sequence is capable of hybridizing to 30 consecutive nucleotides of nucleotides 1-147 of SEQ ID NO:1. In embodiments, the RNA sequence is capable of hybridizing to 35 consecutive nucleotides of nucleotides 1-147 of SEQ ID NO:1. In embodiments, the RNA sequence is capable of hybridizing to 40 consecutive nucleotides of nucleotides 1-147 of SEQ ID NO:1. In embodiments, the RNA sequence is capable of hybridizing to 45 consecutive nucleotides of nucleotides 1-147 of SEQ ID NO:1. In embodiments, the RNA sequence is capable of hybridizing to 50 consecutive nucleotides of nucleotides 1-147 of SEQ ID NO:1.

In embodiments, the RNA sequence is capable of hybridizing to about 15, 16, 17, 18, 19, 20, 21, 22, 23, 24 or 25 consecutive nucleotides of nucleotides 1-147 of SEQ ID NO:1. In embodiments, the RNA sequence is capable of hybridizing to about 15 consecutive nucleotides of nucleotides 1-147 of SEQ ID NO:1. In embodiments, the RNA sequence is capable of hybridizing to about 16 consecutive nucleotides of nucleotides 1-147 of SEQ ID NO:1. In embodiments, the RNA sequence is capable of hybridizing to about 17 consecutive nucleotides of nucleotides 1-147 of SEQ ID NO:1. In embodiments, the RNA sequence is capable of hybridizing to about 18 consecutive nucleotides of nucleotides 1-147 of SEQ ID NO:1. In embodiments, the RNA sequence is capable of hybridizing to about 19 consecutive nucleotides of nucleotides 1-147 of SEQ ID NO:1. In embodiments, the RNA sequence is capable of hybridizing to about 20 consecutive nucleotides of nucleotides 1-147 of SEQ ID NO:1. In embodiments, the RNA sequence is capable of hybridizing to about 21 consecutive nucleotides of nucleotides 1-147 of SEQ ID NO:1. In embodiments, the RNA sequence is capable of hybridizing to about 22 consecutive nucleotides of nucleotides 1-147 of SEQ ID NO:1. In embodiments, the RNA sequence is capable of hybridizing to about 23 consecutive nucleotides of nucleotides 1-147 of SEQ ID NO:1. In embodiments, the RNA sequence is capable of hybridizing to about 24 consecutive nucleotides of nucleotides 1-147 of SEQ ID NO:1. In embodiments, the RNA sequence is capable of hybridizing to about 25 consecutive nucleotides of nucleotides 1-147 of SEQ ID NO:1. In embodiments, the RNA sequence is capable of hybridizing to about 26 consecutive nucleotides of nucleotides 1-147 of SEQ ID NO:1. In embodiments, the RNA sequence is capable of hybridizing to about 27 consecutive nucleotides of nucleotides 1-147 of SEQ ID NO:1. In embodiments, the RNA sequence is capable of hybridizing to about 28 consecutive nucleotides of nucleotides 1-147 of SEQ ID NO:1. In embodiments, the RNA sequence is capable of hybridizing to about 29 consecutive nucleotides of nucleotides 1-147 of SEQ ID NO:1. In embodiments, the RNA sequence is capable of hybridizing to about 30 consecutive nucleotides of nucleotides 1-147 of SEQ ID NO:1. In embodiments, the RNA sequence is capable of hybridizing to about 31 consecutive nucleotides of nucleotides 1-147 of SEQ ID NO:1.

In embodiments, the RNA sequence is capable of hybridizing to about 32 consecutive nucleotides of nucleotides 1-147 of SEQ ID NO:1. In embodiments, the RNA sequence is capable of hybridizing to about 33 consecutive nucleotides of nucleotides 1-147 of SEQ ID NO:1. In embodiments, the RNA sequence is capable of hybridizing to about 34 consecutive nucleotides of nucleotides 1-147 of SEQ ID NO:1. In embodiments, the RNA sequence is capable of hybridizing to about 35 consecutive nucleotides of nucleotides 1-147 of SEQ ID NO:1. In embodiments, the RNA sequence is capable of hybridizing to about 36 consecutive nucleotides of nucleotides 1-147 of SEQ ID NO:1. In embodiments, the RNA sequence is capable of hybridizing to about 37 consecutive nucleotides of nucleotides 1-147 of SEQ ID NO:1. In embodiments, the RNA sequence is capable of hybridizing to about 38 consecutive nucleotides of nucleotides 1-147 of SEQ ID NO:1. In embodiments, the RNA sequence is capable of hybridizing to about 39 consecutive nucleotides of nucleotides 1-147 of SEQ ID NO:1. In embodiments, the RNA sequence is capable of hybridizing to about 40 consecutive nucleotides of nucleotides 1-147 of SEQ ID NO:1. In embodiments, the RNA sequence is capable of hybridizing to about 41 consecutive nucleotides of nucleotides 1-147 of SEQ ID NO:1. In embodiments, the RNA sequence is capable of hybridizing to about 42 consecutive nucleotides of nucleotides 1-147 of SEQ ID NO:1. In embodiments, the RNA sequence is capable of hybridizing to about 43 consecutive nucleotides of nucleotides 1-147 of SEQ ID NO:1. In embodiments, the RNA sequence is capable of hybridizing to about 44 consecutive nucleotides of nucleotides 1-147 of SEQ ID NO:1. In embodiments, the RNA sequence is capable of hybridizing to about 45 consecutive nucleotides of nucleotides 1-147 of SEQ ID NO:1. In embodiments, the RNA sequence is capable of hybridizing to about 46 consecutive nucleotides of nucleotides 1-147 of SEQ ID NO:1. In embodiments, the RNA sequence is capable of hybridizing to about 47 consecutive nucleotides of nucleotides 1-147 of SEQ ID NO:1. In embodiments, the RNA sequence is capable of hybridizing to about 48 consecutive nucleotides of nucleotides 1-147 of SEQ ID NO:1. In embodiments, the RNA sequence is capable of hybridizing to about 49 consecutive nucleotides of nucleotides 1-147 of SEQ ID NO:1. In embodiments, the RNA sequence is capable of hybridizing to about 50 consecutive nucleotides of nucleotides 1-147 of SEQ ID NO:1.

In embodiments, the RNA sequence is capable of hybridizing to 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of nucleotides 1-147 of SEQ ID NO:1. In embodiments, the RNA sequence is capable of hybridizing to 21 consecutive nucleotides of nucleotides 1-147 of SEQ ID NO:1.

In embodiments, the RNA sequence has at least 85% sequence identity to the complement of the consecutive nucleotides. In embodiments, the RNA sequence has at least 86% sequence identity to the complement of the consecutive nucleotides. In embodiments, the RNA sequence has at least 87% sequence identity to the complement of the consecutive nucleotides. In embodiments, the RNA sequence has at least 88% sequence identity to the complement of the consecutive nucleotides. In embodiments, the RNA sequence has at least 89% sequence identity to the complement of the consecutive nucleotides. In embodiments, the RNA sequence has at least 90% sequence identity to the complement of the consecutive nucleotides. In embodiments, the RNA sequence has at least 91% sequence identity to the complement of the consecutive nucleotides. In embodiments, the RNA sequence has at least 92% sequence identity to the complement of the consecutive nucleotides. In embodiments, the RNA sequence has at least 93% sequence identity to the complement of the consecutive nucleotides. In embodiments, the RNA sequence has at least 94% sequence identity to the complement of the consecutive nucleotides. In embodiments, the RNA sequence has at least 95% sequence identity to the complement of the consecutive nucleotides. In embodiments, the RNA sequence has at least 96% sequence identity to the complement of the consecutive nucleotides. In embodiments, the RNA sequence has at least 97% sequence identity to the complement of the consecutive nucleotides. In embodiments, the RNA sequence has at least 98% sequence identity to the complement of the consecutive nucleotides. In embodiments, the RNA sequence has at least 99% sequence identity to the complement of the consecutive nucleotides. In embodiments, the RNA sequence has about 85% sequence identity to the complement of the consecutive nucleotides. In embodiments, the RNA sequence has about 86% sequence identity to the complement of the consecutive nucleotides. In embodiments, the RNA sequence has about 87% sequence identity to the complement of the consecutive nucleotides. In embodiments, the RNA sequence has about 88% sequence identity to the complement of the consecutive nucleotides. In embodiments, the RNA sequence has about 89% sequence identity to the complement of the consecutive nucleotides. In embodiments, the RNA sequence has about 90% sequence identity to the complement of the consecutive nucleotides. In embodiments, the RNA sequence has about 91% sequence identity to the complement of the consecutive nucleotides. In embodiments, the RNA sequence has about 92% sequence identity to the complement of the consecutive nucleotides. In embodiments, the RNA sequence has about 93% sequence identity to the complement of the consecutive nucleotides. In embodiments, the RNA sequence has about 94% sequence identity to the complement of the consecutive nucleotides. In embodiments, the RNA sequence has about 95% sequence identity to the complement of the consecutive nucleotides. In embodiments, the RNA sequence has about 96% sequence identity to the complement of the consecutive nucleotides. In embodiments, the RNA sequence has about 97% sequence identity to the complement of the consecutive nucleotides. In embodiments, the RNA sequence has about 98% sequence identity to the complement of the consecutive nucleotides. In embodiments, the RNA sequence has about 99% sequence identity to the complement of the consecutive nucleotides. In embodiments, the RNA sequence has 85% sequence identity to the complement of the consecutive nucleotides. In embodiments, the RNA sequence has 86% sequence identity to the complement of the consecutive nucleotides. In embodiments, the RNA sequence has 87% sequence identity to the complement of the consecutive nucleotides. In embodiments, the RNA sequence has 88% sequence identity to the complement of the consecutive nucleotides. In embodiments, the RNA sequence has 89% sequence identity to the complement of the consecutive nucleotides. In embodiments, the RNA sequence has 90% sequence identity to the complement of the consecutive nucleotides. In embodiments, the RNA sequence has 91% sequence identity to the complement of the consecutive nucleotides. In embodiments, the RNA sequence has 92% sequence identity to the complement of the consecutive nucleotides. In embodiments, the RNA sequence has 93% sequence identity to the complement of the consecutive nucleotides. In embodiments, the RNA sequence has 94% sequence identity to the complement of the consecutive nucleotides. In embodiments, the RNA sequence has 95% sequence identity to the complement of the consecutive nucleotides. In embodiments, the RNA sequence has 96% sequence identity to the complement of the consecutive nucleotides. In embodiments, the RNA sequence has 97% sequence identity to the complement of the consecutive nucleotides. In embodiments, the RNA sequence has 98% sequence identity to the complement of the consecutive nucleotides. In embodiments, the RNA sequence has 99% sequence identity to the complement of the consecutive nucleotides.

In embodiments, the RNA sequence is capable of hybridizing to nucleotides 27-47 of SEQ ID NO:1. In embodiments, the RNA sequence has at least 80% sequence identity to the complement of SEQ ID NO:1. In embodiments, the RNA sequence has at least 85% sequence identity to the complement of SEQ ID NO:1. In embodiments, the RNA sequence has at least 86% sequence identity to the complement of SEQ ID NO:1. In embodiments, the RNA sequence has at least 87% sequence identity to the complement of SEQ ID NO:1. In embodiments, the RNA sequence has at least 88% sequence identity to the complement of SEQ ID NO:1. In embodiments, the RNA sequence has at least 89% sequence identity to the complement of SEQ ID NO:1. In embodiments, the RNA sequence has at least 90% sequence identity to the complement of SEQ ID NO:1. In embodiments, the RNA sequence has at least 91% sequence identity to the complement of SEQ ID NO:1. In embodiments, the RNA sequence has at least 92% sequence identity to the complement of SEQ ID NO:1. In embodiments, the RNA sequence has at least 93% sequence identity to the complement of SEQ ID NO:1. In embodiments, the RNA sequence has at least 94% sequence identity to the complement of SEQ ID NO:1. In embodiments, the RNA sequence has at least 95% sequence identity to the complement of SEQ ID NO:1. In embodiments, the RNA sequence has at least 96% sequence identity to the complement of SEQ ID NO:1. In embodiments, the RNA sequence has at least 97% sequence identity to the complement of SEQ ID NO:1. In embodiments, the RNA sequence has at least 98% sequence identity to the complement of SEQ ID NO:1.

In embodiments, the RNA sequence is capable of hybridizing to nucleotides 27-47 of SEQ ID NO:1. In embodiments, the RNA sequence has about 80% sequence identity to the complement of SEQ ID NO:1. In embodiments, the RNA sequence has about 85% sequence identity to the complement of SEQ ID NO:1. In embodiments, the RNA sequence has about 86% sequence identity to the complement of SEQ ID NO:1. In embodiments, the RNA sequence has about 87% sequence identity to the complement of SEQ ID NO:1. In embodiments, the RNA sequence has about 88% sequence identity to the complement of SEQ ID NO:1. In embodiments, the RNA sequence has about 89% sequence identity to the complement of SEQ ID NO:1. In embodiments, the RNA sequence has about 90% sequence identity to the complement of SEQ ID NO:1. In embodiments, the RNA sequence has about 91% sequence identity to the complement of SEQ ID NO:1. In embodiments, the RNA sequence has about 92% sequence identity to the complement of SEQ ID NO:1. In embodiments, the RNA sequence has about 93% sequence identity to the complement of SEQ ID NO:1. In embodiments, the RNA sequence has about 94% sequence identity to the complement of SEQ ID NO:1. In embodiments, the RNA sequence has about 95% sequence identity to the complement of SEQ ID NO:1. In embodiments, the RNA sequence has about 96% sequence identity to the complement of SEQ ID NO:1. In embodiments, the RNA sequence has about 97% sequence identity to the complement of SEQ ID NO:1. In embodiments, the RNA sequence has about 98% sequence identity to the complement of SEQ ID NO:1.

In embodiments, the RNA sequence is capable of hybridizing to nucleotides 27-47 of SEQ ID NO:1. In embodiments, the RNA sequence has 80% sequence identity to the complement of SEQ ID NO:1. In embodiments, the RNA sequence has 85% sequence identity to the complement of SEQ ID NO:1. In embodiments, the RNA sequence has 86% sequence identity to the complement of SEQ ID NO:1. In embodiments, the RNA sequence has 87% sequence identity to the complement of SEQ ID NO:1. In embodiments, the RNA sequence has 88% sequence identity to the complement of SEQ ID NO:1. In embodiments, the RNA sequence has 89% sequence identity to the complement of SEQ ID NO:1. In embodiments, the RNA sequence has 90% sequence identity to the complement of SEQ ID NO:1. In embodiments, the RNA sequence has 91% sequence identity to the complement of SEQ ID NO:1. In embodiments, the RNA sequence has 92% sequence identity to the complement of SEQ ID NO:1. In embodiments, the RNA sequence has 93% sequence identity to the complement of SEQ ID NO:1. In embodiments, the RNA sequence has 94% sequence identity to the complement of SEQ ID NO:1. In embodiments, the RNA sequence has 95% sequence identity to the complement of SEQ ID NO:1. In embodiments, the RNA sequence has 96% sequence identity to the complement of SEQ ID NO:1. In embodiments, the RNA sequence has 97% sequence identity to the complement of SEQ ID NO:1. In embodiments, the RNA sequence has 98% sequence identity to the complement of SEQ ID NO:1. In embodiments, the RNA sequence has 99% sequence identity to the complement of SEQ ID NO:1. In embodiments, the RNA sequence has 100% sequence identity to the complement of SEQ ID NO:1.

In embodiments, the RNA sequence is capable of hybridizing to nucleotides 28-47, nucleotides 28-47, nucleotides 30-47, nucleotides 31-47, nucleotides 32-47, nucleotides 33-47, nucleotides 34-47, nucleotides 35-47, or nucleotides 36-47 of SEQ ID NO:1. In embodiments, the RNA sequence has 80% sequence identity to the complement of SEQ ID NO:1. In embodiments, the RNA sequence has 85% sequence identity to the complement of SEQ ID NO:1. In embodiments, the RNA sequence has 86% sequence identity to the complement of SEQ ID NO:1. In embodiments, the RNA sequence has 87% sequence identity to the complement of SEQ ID NO:1. In embodiments, the RNA sequence has 88% sequence identity to the complement of SEQ ID NO:1. In embodiments, the RNA sequence has 89% sequence identity to the complement of SEQ ID NO:1. In embodiments, the RNA sequence has 90% sequence identity to the complement of SEQ ID NO:1. In embodiments, the RNA sequence has 91% sequence identity to the complement of SEQ ID NO:1. In embodiments, the RNA sequence has 92% sequence identity to the complement of SEQ ID NO:1. In embodiments, the RNA sequence has 93% sequence identity to the complement of SEQ ID NO:1. In embodiments, the RNA sequence has 94% sequence identity to the complement of SEQ ID NO:1. In embodiments, the RNA sequence has 95% sequence identity to the complement of SEQ ID NO:1. In embodiments, the RNA sequence has 96% sequence identity to the complement of SEQ ID NO:1. In embodiments, the RNA sequence has 97% sequence identity to the complement of SEQ ID NO:1. In embodiments, the RNA sequence has 98% sequence identity to the complement of SEQ ID NO:1. In embodiments, the RNA sequence has 99% sequence identity to the complement of SEQ ID NO:1. In embodiments, the RNA sequence has 100% sequence identity to the complement of SEQ ID NO:1.

In embodiments, the RNA sequence is SEQ ID NO:12. In embodiments, the RNA sequence includes SEQ ID NO:12. In embodiments, the RNA sequence is SEQ ID NOs:11 and 12. In embodiments, the RNA sequence includes SEQ ID NOs:11 and 12.

In embodiments, the RNA sequence is a single-stranded RNA sequence. In embodiments, the RNA sequence is a double-stranded RNA sequence. In embodiments, the RNA sequence is an LDLR-activating sequence. In embodiments, the RNA sequence is a small RNA. In embodiments, the RNA sequence is a transcriptional gene silencing (TGS) RNA.

Small RNAs Binding lncRNA Sequences

In another aspect, there is provided a ribonucleic acid compound including an RNA sequence, the RNA sequence having at least 80% sequence identity to the complement of at least 15 consecutive nucleotides of nucleotides 541-631 of SEQ ID NO:2.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region. Therefore, the RNA sequences provided herein (e.g., the sequence of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22) may have a sequence identity from about 80% to about 100%. In embodiments, the RNA sequence has at least 85% sequence identity to the complement of at least 15 consecutive nucleotides of nucleotides 541-631 of SEQ ID NO:2. In embodiments, the RNA sequence has at least 86% sequence identity to the complement of at least 15 consecutive nucleotides of nucleotides 541-631 of SEQ ID NO:2. In embodiments, the RNA sequence has at least 87% sequence identity to the complement of at least 15 consecutive nucleotides of nucleotides 541-631 of SEQ ID NO:2. In embodiments, the RNA sequence has at least 88% sequence identity to the complement of at least 15 consecutive nucleotides of nucleotides 541-631 of SEQ ID NO:2. In embodiments, the RNA sequence has at least 89% sequence identity to the complement of at least 15 consecutive nucleotides of nucleotides 541-631 of SEQ ID NO:2. In embodiments, the RNA sequence has at least 90% sequence identity to the complement of at least 15 consecutive nucleotides of nucleotides 541-631 of SEQ ID NO:2. In embodiments, the RNA sequence has at least 91% sequence identity to the complement of at least 15 consecutive nucleotides of nucleotides 541-631 of SEQ ID NO:2. In embodiments, the RNA sequence has at least 92% sequence identity to the complement of at least 15 consecutive nucleotides of nucleotides 541-631 of SEQ ID NO:2. In embodiments, the RNA sequence has at least 93% sequence identity to the complement of at least 15 consecutive nucleotides of nucleotides 541-631 of SEQ ID NO:2. In embodiments, the RNA sequence has at least 94% sequence identity to the complement of at least 15 consecutive nucleotides of nucleotides 541-631 of SEQ ID NO:2. In embodiments, the RNA sequence has at least 95% sequence identity to the complement of at least 15 consecutive nucleotides of nucleotides 541-631 of SEQ ID NO:2. In embodiments, the RNA sequence has at least 96% sequence identity to the complement of at least 15 consecutive nucleotides of nucleotides 541-631 of SEQ ID NO:2. In embodiments, the RNA sequence has at least 97% sequence identity to the complement of at least 15 consecutive nucleotides of nucleotides 541-631 of SEQ ID NO:2. In embodiments, the RNA sequence has at least 98% sequence identity to the complement of at least 15 consecutive nucleotides of nucleotides 541-631 of SEQ ID NO:2. In embodiments, the RNA sequence has at least 99% sequence identity to the complement of at least 15 consecutive nucleotides of nucleotides 541-631 of SEQ ID NO:2.

In embodiments, the RNA sequence has 85% sequence identity to the complement of at least 15 consecutive nucleotides of nucleotides 541-631 of SEQ ID NO:2. In embodiments, the RNA sequence has 86% sequence identity to the complement of at least 15 consecutive nucleotides of nucleotides 541-631 of SEQ ID NO:2. In embodiments, the RNA sequence has 87% sequence identity to the complement of at least 15 consecutive nucleotides of nucleotides 541-631 of SEQ ID NO:2. In embodiments, the RNA sequence has 88% sequence identity to the complement of at least 15 consecutive nucleotides of nucleotides 541-631 of SEQ ID NO:2. In embodiments, the RNA sequence has 89% sequence identity to the complement of at least 15 consecutive nucleotides of nucleotides 541-631 of SEQ ID NO:2. In embodiments, the RNA sequence has 90% sequence identity to the complement of at least 15 consecutive nucleotides of nucleotides 541-631 of SEQ ID NO:2. In embodiments, the RNA sequence has 91% sequence identity to the complement of at least 15 consecutive nucleotides of nucleotides 541-631 of SEQ ID NO:2. In embodiments, the RNA sequence has 92% sequence identity to the complement of at least 15 consecutive nucleotides of nucleotides 541-631 of SEQ ID NO:2. In embodiments, the RNA sequence has 93% sequence identity to the complement of at least 15 consecutive nucleotides of nucleotides 541-631 of SEQ ID NO:2. In embodiments, the RNA sequence has 94% sequence identity to the complement of at least 15 consecutive nucleotides of nucleotides 541-631 of SEQ ID NO:2. In embodiments, the RNA sequence has 95% sequence identity to the complement of at least 15 consecutive nucleotides of nucleotides 541-631 of SEQ ID NO:2. In embodiments, the RNA sequence has 96% sequence identity to the complement of at least 15 consecutive nucleotides of nucleotides 541-631 of SEQ ID NO:2. In embodiments, the RNA sequence has 97% sequence identity to the complement of at least 15 consecutive nucleotides of nucleotides 541-631 of SEQ ID NO:2. In embodiments, the RNA sequence has 98% sequence identity to the complement of at least 15 consecutive nucleotides of nucleotides 541-631 of SEQ ID NO:2. In embodiments, the RNA sequence has 99% sequence identity to the complement of at least 15 consecutive nucleotides of nucleotides 541-631 of SEQ ID NO:2. In embodiments, the RNA sequence has 100% sequence identity to the complement of at least 15 consecutive nucleotides of nucleotides 541-631 of SEQ ID NO:2.

In embodiments, the RNA sequence has 85% sequence identity to the complement of 15 consecutive nucleotides of nucleotides 541-631 of SEQ ID NO:2. In embodiments, the RNA sequence has 86% sequence identity to the complement of 15 consecutive nucleotides of nucleotides 541-631 of SEQ ID NO:2. In embodiments, the RNA sequence has 87% sequence identity to the complement of 15 consecutive nucleotides of nucleotides 541-631 of SEQ ID NO:2. In embodiments, the RNA sequence has 88% sequence identity to the complement of 15 consecutive nucleotides of nucleotides 541-631 of SEQ ID NO:2. In embodiments, the RNA sequence has 89% sequence identity to the complement of 15 consecutive nucleotides of nucleotides 541-631 of SEQ ID NO:2. In embodiments, the RNA sequence has 90% sequence identity to the complement of 15 consecutive nucleotides of nucleotides 541-631 of SEQ ID NO:2. In embodiments, the RNA sequence has 91% sequence identity to the complement of 15 consecutive nucleotides of nucleotides 541-631 of SEQ ID NO:2. In embodiments, the RNA sequence has 92% sequence identity to the complement of 15 consecutive nucleotides of nucleotides 541-631 of SEQ ID NO:2. In embodiments, the RNA sequence has 93% sequence identity to the complement of 15 consecutive nucleotides of nucleotides 541-631 of SEQ ID NO:2. In embodiments, the RNA sequence has 94% sequence identity to the complement of 15 consecutive nucleotides of nucleotides 541-631 of SEQ ID NO:2. In embodiments, the RNA sequence has 95% sequence identity to the complement of 15 consecutive nucleotides of nucleotides 541-631 of SEQ ID NO:2. In embodiments, the RNA sequence has 96% sequence identity to the complement of 15 consecutive nucleotides of nucleotides 541-631 of SEQ ID NO:2. In embodiments, the RNA sequence has 97% sequence identity to the complement of 15 consecutive nucleotides of nucleotides 541-631 of SEQ ID NO:2. In embodiments, the RNA sequence has 98% sequence identity to the complement of 15 consecutive nucleotides of nucleotides 541-631 of SEQ ID NO:2. In embodiments, the RNA sequence has 99% sequence identity to the complement of 15 consecutive nucleotides of nucleotides 541-631 of SEQ ID NO:2. In embodiments, the RNA sequence has 100% sequence identity to the complement of 15 consecutive nucleotides of nucleotides 541-631 of SEQ ID NO:2.

The ribonucleic acid compounds provided herein may hybridize (bind) to a lncRNA (e.g., the sequence of SEQ ID NO:2) or a lncRNA promoter sequence (e.g., the sequence of SEQ ID NO:1). The ribonucleic acid compounds provided herein may hybridize (bind) to a specific number of nucleotides within the lncRNA or lncRNA promoter sequence and the nucleotides are consecutive nucleotides. For example, the RNA sequence included in the ribonucleic acid compounds provided herein may bind to at least 15 consecutive nucleotides of SEQ ID NO:1 or SEQ ID NO:2. In embodiments, the RNA sequence has at least 80% sequence identity to the complement of at least 15 consecutive nucleotides of nucleotides 541-631 of SEQ ID NO:2. In embodiments, the RNA sequence has at least 80% sequence identity to the complement of at least 16 consecutive nucleotides of nucleotides 541-631 of SEQ ID NO:2. In embodiments, the RNA sequence has at least 80% sequence identity to the complement of at least 17 consecutive nucleotides of nucleotides 541-631 of SEQ ID NO:2. In embodiments, the RNA sequence has at least 80% sequence identity to the complement of at least 18 consecutive nucleotides of nucleotides 541-631 of SEQ ID NO:2. In embodiments, the RNA sequence has at least 80% sequence identity to the complement of at least 19 consecutive nucleotides of nucleotides 541-631 of SEQ ID NO:2. In embodiments, the RNA sequence has at least 80% sequence identity to the complement of at least 20 consecutive nucleotides of nucleotides 541-631 of SEQ ID NO:2. In embodiments, the RNA sequence has at least 80% sequence identity to the complement of at least 25 consecutive nucleotides of nucleotides 541-631 of SEQ ID NO:2. In embodiments, the RNA sequence has at least 80% sequence identity to the complement of at least 30 consecutive nucleotides of nucleotides 541-631 of SEQ ID NO:2. In embodiments, the RNA sequence has at least 80% sequence identity to the complement of at least 35 consecutive nucleotides of nucleotides 541-631 of SEQ ID NO:2. In embodiments, the RNA sequence has at least 80% sequence identity to the complement of at least 40 consecutive nucleotides of nucleotides 541-631 of SEQ ID NO:2. In embodiments, the RNA sequence has at least 80% sequence identity to the complement of at least 45 consecutive nucleotides of nucleotides 541-631 of SEQ ID NO:2. In embodiments, the RNA sequence has at least 80% sequence identity to the complement of at least 50 consecutive nucleotides of nucleotides 541-631 of SEQ ID NO:2.

In embodiments, the RNA sequence has at least 80% sequence identity to the complement of 15 consecutive nucleotides of nucleotides 541-631 of SEQ ID NO:2. In embodiments, the RNA sequence has at least 80% sequence identity to the complement of 16 consecutive nucleotides of nucleotides 541-631 of SEQ ID NO:2. In embodiments, the RNA sequence has at least 80% sequence identity to the complement of 17 consecutive nucleotides of nucleotides 541-631 of SEQ ID NO:2. In embodiments, the RNA sequence has at least 80% sequence identity to the complement of 18 consecutive nucleotides of nucleotides 541-631 of SEQ ID NO:2. In embodiments, the RNA sequence has at least 80% sequence identity to the complement of 19 consecutive nucleotides of nucleotides 541-631 of SEQ ID NO:2. In embodiments, the RNA sequence has at least 80% sequence identity to the complement of 20 consecutive nucleotides of nucleotides 541-631 of SEQ ID NO:2. In embodiments, the RNA sequence has at least 80% sequence identity to the complement of 25 consecutive nucleotides of nucleotides 541-631 of SEQ ID NO:2. In embodiments, the RNA sequence has at least 80% sequence identity to the complement of 30 consecutive nucleotides of nucleotides 541-631 of SEQ ID NO:2. In embodiments, the RNA sequence has at least 80% sequence identity to the complement of 35 consecutive nucleotides of nucleotides 541-631 of SEQ ID NO:2. In embodiments, the RNA sequence has at least 80% sequence identity to the complement of 40 consecutive nucleotides of nucleotides 541-631 of SEQ ID NO:2. In embodiments, the RNA sequence has at least 80% sequence identity to the complement of 45 consecutive nucleotides of nucleotides 541-631 of SEQ ID NO:2. In embodiments, the RNA sequence has at least 80% sequence identity to the complement of 50 consecutive nucleotides of nucleotides 541-631 of SEQ ID NO:2.

In embodiments, the RNA sequence has 80% sequence identity to the complement of 15 consecutive nucleotides of nucleotides 541-631 of SEQ ID NO:2. In embodiments, the RNA sequence has 80% sequence identity to the complement of 16 consecutive nucleotides of nucleotides 541-631 of SEQ ID NO:2. In embodiments, the RNA sequence has 80% sequence identity to the complement of 17 consecutive nucleotides of nucleotides 541-631 of SEQ ID NO:2. In embodiments, the RNA sequence has 80% sequence identity to the complement of 18 consecutive nucleotides of nucleotides 541-631 of SEQ ID NO:2. In embodiments, the RNA sequence has 80% sequence identity to the complement of 19 consecutive nucleotides of nucleotides 541-631 of SEQ ID NO:2. In embodiments, the RNA sequence has 80% sequence identity to the complement of 20 consecutive nucleotides of nucleotides 541-631 of SEQ ID NO:2. In embodiments, the RNA sequence has 80% sequence identity to the complement of 25 consecutive nucleotides of nucleotides 541-631 of SEQ ID NO:2. In embodiments, the RNA sequence has 80% sequence identity to the complement of 30 consecutive nucleotides of nucleotides 541-631 of SEQ ID NO:2. In embodiments, the RNA sequence has 80% sequence identity to the complement of 35 consecutive nucleotides of nucleotides 541-631 of SEQ ID NO:2. In embodiments, the RNA sequence has 80% sequence identity to the complement of 40 consecutive nucleotides of nucleotides 541-631 of SEQ ID NO:2. In embodiments, the RNA sequence has 80% sequence identity to the complement of 45 consecutive nucleotides of nucleotides 541-631 of SEQ ID NO:2. In embodiments, the RNA sequence has 80% sequence identity to the complement of 50 consecutive nucleotides of nucleotides 541-631 of SEQ ID NO:2.

The ribonucleic acid compounds provided herein may hybridize (bind) to a specific portion of the lncRNA (e.g., the sequence of SEQ ID NO:2). The portion may include nucleotides 541-631 of SEQ ID NO:2. In embodiments, the RNA sequence has at least 80% sequence identity to the complement of at least 15 consecutive nucleotides of nucleotides 541-631 of SEQ ID NO:2. In embodiments, the RNA sequence has at least 80% sequence identity to the complement of at least 15 consecutive nucleotides of nucleotides 542-631 of SEQ ID NO:2. In embodiments, the RNA sequence has at least 80% sequence identity to the complement of at least 15 consecutive nucleotides of nucleotides 543-631 of SEQ ID NO:2. In embodiments, the RNA sequence has at least 80% sequence identity to the complement of at least 15 consecutive nucleotides of nucleotides 544-631 of SEQ ID NO:2. In embodiments, the RNA sequence has at least 80% sequence identity to the complement of at least 15 consecutive nucleotides of nucleotides 545-631 of SEQ ID NO:2. In embodiments, the RNA sequence has at least 80% sequence identity to the complement of at least 15 consecutive nucleotides of nucleotides 546-631 of SEQ ID NO:2. In embodiments, the RNA sequence has at least 80% sequence identity to the complement of at least 15 consecutive nucleotides of nucleotides 547-631 of SEQ ID NO:2. For the above embodiments, the RNA sequence may have about 85%, 90%, 92%, 93%, 94%, 95%, 96%, 97%, 98% or 99% sequence identity to the complement of at least 15 (e.g., 15, 16, 17, 18, 19, 20, 21, 22, 23, or 25) consecutive nucleotides of nucleotides 541-631, 542-631, 543-631, 543-631, 545-631, 546-631, or 547-631 of SEQ ID NO:2.

In embodiments, the RNA sequence has at least 80% sequence identity to the complement of at least 15 consecutive nucleotides of nucleotides 548-631 of SEQ ID NO:2. In embodiments, the RNA sequence has at least 80% sequence identity to the complement of at least 15 consecutive nucleotides of nucleotides 549-631 of SEQ ID NO:2. In embodiments, the RNA sequence has at least 80% sequence identity to the complement of at least 15 consecutive nucleotides of nucleotides 550-631 of SEQ ID NO:2. In embodiments, the RNA sequence has at least 80% sequence identity to the complement of at least 15 consecutive nucleotides of nucleotides 551-631 of SEQ ID NO:2. In embodiments, the RNA sequence has at least 80% sequence identity to the complement of at least 15 consecutive nucleotides of nucleotides 552-631 of SEQ ID NO:2. In embodiments, the RNA sequence has at least 80% sequence identity to the complement of at least 15 consecutive nucleotides of nucleotides 553-631 of SEQ ID NO:2. In embodiments, the RNA sequence has at least 80% sequence identity to the complement of at least 15 consecutive nucleotides of nucleotides 554-631 of SEQ ID NO:2. In embodiments, the RNA sequence has at least 80% sequence identity to the complement of at least 15 consecutive nucleotides of nucleotides 555-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 548-631, 549-631, 550-631, 551-631, 552-631, 553-631, 554-631, or 555-631 of SEQ ID NO:2.

In embodiments, the RNA sequence has at least 80% sequence identity to the complement of at least 15 consecutive nucleotides of nucleotides 556-631 of SEQ ID NO:2. In embodiments, the RNA sequence has at least 80% sequence identity to the complement of at least 15 consecutive nucleotides of nucleotides 557-631 of SEQ ID NO:2. In embodiments, the RNA sequence has at least 80% sequence identity to the complement of at least 15 consecutive nucleotides of nucleotides 558-631 of SEQ ID NO:2. In embodiments, the RNA sequence has at least 80% sequence identity to the complement of at least 15 consecutive nucleotides of nucleotides 559-631 of SEQ ID NO:2. In embodiments, the RNA sequence has at least 80% sequence identity to the complement of at least 15 consecutive nucleotides of nucleotides 560-631 of SEQ ID NO:2. In embodiments, the RNA sequence has at least 80% sequence identity to the complement of at least 15 consecutive nucleotides of nucleotides 561-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 556-631, 557-631, 557-631, 558-631, 559-631, 560-631, or 561-631 of SEQ ID NO:2.

In embodiments, the RNA sequence has at least 80% sequence identity to the complement of at least 15 consecutive nucleotides of nucleotides 562-631 of SEQ ID NO:2. In embodiments, the RNA sequence has at least 80% sequence identity to the complement of at least 15 consecutive nucleotides of nucleotides 563-631 of SEQ ID NO:2. In embodiments, the RNA sequence has at least 80% sequence identity to the complement of at least 15 consecutive nucleotides of nucleotides 564-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 562-631, 563-631, or 564-631 of SEQ ID NO:2.

In embodiments, the RNA sequence has at least 80% sequence identity to the complement of at least 15 consecutive nucleotides of nucleotides 565-631 of SEQ In embodiments, the RNA sequence has at least 80% sequence identity to the complement of at least 15 consecutive nucleotides of nucleotides 566-631 of SEQ ID NO:2. ID NO:2. In embodiments, the RNA sequence has at least 80% sequence identity to the complement of at least 15 consecutive nucleotides of nucleotides 567-631 of SEQ ID NO:2. In embodiments, the RNA sequence has at least 80% sequence identity to the complement of at least 15 consecutive nucleotides of nucleotides 568-631 of SEQ ID NO:2. In embodiments, the RNA sequence has at least 80% sequence identity to the complement of at least 15 consecutive nucleotides of nucleotides 569-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 565-631, 566-631, 567-631, 568-631, or 569-631 of SEQ ID NO:2.

In embodiments, the RNA sequence has at least 80% sequence identity to the complement of at least 15 consecutive nucleotides of nucleotides 570-631 of SEQ ID NO:2. In embodiments, the RNA sequence has at least 80% sequence identity to the complement of at least 15 consecutive nucleotides of nucleotides 571-631 of SEQ ID NO:2. In embodiments, the RNA sequence has at least 80% sequence identity to the complement of at least 15 consecutive nucleotides of nucleotides 572-631 of SEQ ID NO:2. In embodiments, the RNA sequence has at least 80% sequence identity to the complement of at least 15 consecutive nucleotides of nucleotides 573-631 of SEQ ID NO:2. In embodiments, the RNA sequence has at least 80% sequence identity to the complement of at least 15 consecutive nucleotides of nucleotides 574-631 of SEQ ID NO:2. In embodiments, the RNA sequence has at least 80% sequence identity to the complement of at least 15 consecutive nucleotides of nucleotides 575-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 570-631, 571-631, 572-631, 573-631, 574-631, or 575-631 of SEQ ID NO:2.

In embodiments, the RNA sequence has at least 80% sequence identity to the complement of at least 15 consecutive nucleotides of nucleotides 576-631 of SEQ ID NO:2. In embodiments, the RNA sequence has at least 80% sequence identity to the complement of at least 15 consecutive nucleotides of nucleotides 577-631 of SEQ ID NO:2. In embodiments, the RNA sequence has at least 80% sequence identity to the complement of at least 15 consecutive nucleotides of nucleotides 578-631 of SEQ ID NO:2. In embodiments, the RNA sequence has at least 80% sequence identity to the complement of at least 15 consecutive nucleotides of nucleotides 579-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 576-631, 577-631, 578-631, or 579-631 of SEQ ID NO:2.

In embodiments, the RNA sequence has at least 80% sequence identity to the complement of at least 15 consecutive nucleotides of nucleotides 580-631 of SEQ ID NO:2. In embodiments, the RNA sequence has at least 80% sequence identity to the complement of at least 15 consecutive nucleotides of nucleotides 581-631 of SEQ ID NO:2. In embodiments, the RNA sequence has at least 80% sequence identity to the complement of at least 15 consecutive nucleotides of nucleotides 582-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 580-631, 581-631, or 582-631, of SEQ ID NO:2.

In embodiments, the RNA sequence has at least 80% sequence identity to the complement of at least 15 consecutive nucleotides of nucleotides 583-631 of SEQ ID NO:2. In embodiments, the RNA sequence has at least 80% sequence identity to the complement of at least 15 consecutive nucleotides of nucleotides 584-631 of SEQ ID NO:2. In embodiments, the RNA sequence has at least 80% sequence identity to the complement of at least 15 consecutive nucleotides of nucleotides 585-631 of SEQ ID NO:2. In embodiments, the RNA sequence has at least 80% sequence identity to the complement of at least 15 consecutive nucleotides of nucleotides 586-631 of SEQ ID NO:2. In embodiments, the RNA sequence has at least 80% sequence identity to the complement of at least 15 consecutive nucleotides of nucleotides 587-631 of SEQ ID NO:2. In embodiments, the RNA sequence has at least 80% sequence identity to the complement of at least 15 consecutive nucleotides of nucleotides 588-631 of SEQ ID NO:2. In embodiments, the RNA sequence has at least 80% sequence identity to the complement of at least 15 consecutive nucleotides of nucleotides 589-631 of SEQ ID NO:2. In embodiments, the RNA sequence has at least 80% sequence identity to the complement of at least 15 consecutive nucleotides of nucleotides 590-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 583-631, 584-631, 585-631, 586-631, 587-631, 588-631, 589-631 or 590-631 of SEQ ID NO:2.

In embodiments, the RNA sequence has at least 80% sequence identity to the complement of at least 15 consecutive nucleotides of nucleotides 591-631 of SEQ ID NO:2. In embodiments, the RNA sequence has at least 80% sequence identity to the complement of at least 15 consecutive nucleotides of nucleotides 592-631 of SEQ ID NO:2. In embodiments, the RNA sequence has at least 80% sequence identity to the complement of at least 15 consecutive nucleotides of nucleotides 593-631 of SEQ ID NO:2. In embodiments, the RNA sequence has at least 80% sequence identity to the complement of at least 15 consecutive nucleotides of nucleotides 594-631 of SEQ ID NO:2. In embodiments, the RNA sequence has at least 80% sequence identity to the complement of at least 15 consecutive nucleotides of nucleotides 595-631 of SEQ ID NO:2. In embodiments, the RNA sequence has at least 80% sequence identity to the complement of at least 15 consecutive nucleotides of nucleotides 596-631 of SEQ ID NO:2. In embodiments, the RNA sequence has at least 80% sequence identity to the complement of at least 15 consecutive nucleotides of nucleotides 597-631 of SEQ ID NO:2. In embodiments, the RNA sequence has at least 80% sequence identity to the complement of at least 15 consecutive nucleotides of nucleotides 598-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 591-631, 592-631, 593-631, 594-631, 595-631, 596-631, 597-631 or 598-631 of SEQ ID NO:2.

In embodiments, the RNA sequence has at least 80% sequence identity to the complement of at least 15 consecutive nucleotides of nucleotides 599-631 of SEQ ID NO:2. In embodiments, the RNA sequence has at least 80% sequence identity to the complement of at least 15 consecutive nucleotides of nucleotides 600-631 of SEQ ID NO:2. In embodiments, the RNA sequence has at least 80% sequence identity to the complement of at least 15 consecutive nucleotides of nucleotides 601-631 of SEQ ID NO:2. In embodiments, the RNA sequence has at least 80% sequence identity to the complement of at least 15 consecutive nucleotides of nucleotides 602 of SEQ ID NO:2. In embodiments, the RNA sequence has at least 80% sequence identity to the complement of at least 15 consecutive nucleotides of nucleotides 603-631 of SEQ ID NO:2. In embodiments, the RNA sequence has at least 80% sequence identity to the complement of at least 15 consecutive nucleotides of nucleotides 604-631 of SEQ ID NO:2. In embodiments, the RNA sequence has at least 80% sequence identity to the complement of at least 15 consecutive nucleotides of nucleotides 605-631 of SEQ ID NO:2. In embodiments, the RNA sequence has at least 80% sequence identity to the complement of at least 15 consecutive nucleotides of nucleotides 606-631 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 599-631, 600-631, 601-631, 602-631, 603-631, 604-631, 605-631 or 606-631 of SEQ ID NO:2.

In embodiments, the RNA sequence has at least 80% sequence identity to the complement of at least 15 consecutive nucleotides of nucleotides 541-631 of SEQ ID NO:2. In embodiments, the RNA sequence has at least 80% sequence identity to the complement of at least 15 consecutive nucleotides of nucleotides 541-630 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 580-631, 581-631, 582-631, 541-631, or 541-630 of SEQ ID NO:2.

In embodiments, the RNA sequence has at least 80% sequence identity to the complement of at least 15 consecutive nucleotides of nucleotides 541-629 of SEQ ID NO:2. In embodiments, the RNA sequence has at least 80% sequence identity to the complement of at least 15 consecutive nucleotides of nucleotides 541-628 of SEQ ID NO:2. In embodiments, the RNA sequence has at least 80% sequence identity to the complement of at least 15 consecutive nucleotides of nucleotides 541-627 of SEQ ID NO:2. In embodiments, the RNA sequence has at least 80% sequence identity to the complement of at least 15 consecutive nucleotides of nucleotides 541-626 of SEQ ID NO:2. In embodiments, the RNA sequence has at least 80% sequence identity to the complement of at least 15 consecutive nucleotides of nucleotides 541-625 of SEQ ID NO:2. In embodiments, the RNA sequence has at least 80% sequence identity to the complement of at least 15 consecutive nucleotides of nucleotides 541-624 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 541-629, 541-628, 541-627, 541-626, 541-625, or 541-624 of SEQ ID NO:2.

In embodiments, the RNA sequence has at least 80% sequence identity to the complement of at least 15 consecutive nucleotides of nucleotides 541-623 of SEQ ID NO:2. In embodiments, the RNA sequence has at least 80% sequence identity to the complement of at least 15 consecutive nucleotides of nucleotides 541-622 of SEQ ID NO:2. In embodiments, the RNA sequence has at least 80% sequence identity to the complement of at least 15 consecutive nucleotides of nucleotides 541-621 of SEQ ID NO:2. In embodiments, the RNA sequence has at least 80% sequence identity to the complement of at least 15 consecutive nucleotides of nucleotides 541-620 of SEQ ID NO:2. For the above embodiments, the RNA sequence may have about 85%, 90%, 91%. 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 541-623, 541-622, 541-621, or 541-620 of SEQ ID NO:2.

In embodiments, the RNA sequence has at least 80% sequence identity to the complement of at least 15 consecutive nucleotides of nucleotides 541-619 of SEQ ID NO:2. In embodiments, the RNA sequence has at least 80% sequence identity to the complement of at least 15 consecutive nucleotides of nucleotides 541-618 of SEQ ID NO:2. In embodiments, the RNA sequence has at least 80% sequence identity to the complement of at least 15 consecutive nucleotides of nucleotides 541-617 of SEQ ID NO:2. In embodiments, the RNA sequence has at least 80% sequence identity to the complement of at least 15 consecutive nucleotides of nucleotides 541-616 of SEQ ID NO:2. In embodiments, the RNA sequence has at least 80% sequence identity to the complement of at least 15 consecutive nucleotides of nucleotides 541-615 of SEQ ID NO:2. In embodiments, the RNA sequence has at least 80% sequence identity to the complement of at least 15 consecutive nucleotides of nucleotides 541-614 of SEQ ID NO:2. In embodiments, the RNA sequence has at least 80% sequence identity to the complement of at least 15 consecutive nucleotides of nucleotides 541-613 of SEQ ID NO:2. For the above embodiments, the RNA sequence may have about 85%, 90%, 91%. 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 541-619, 541-618, 541-617, 541-616, 541-615, 541-614, or 541-613 of SEQ ID NO:2.

In embodiments, the RNA sequence has at least 80% sequence identity to the complement of at least 15 consecutive nucleotides of nucleotides 541-612 of SEQ ID NO:2. In embodiments, the RNA sequence has at least 80% sequence identity to the complement of at least 15 consecutive nucleotides of nucleotides 541-611 of SEQ ID NO:2. In embodiments, the RNA sequence has at least 80% sequence identity to the complement of at least 15 consecutive nucleotides of nucleotides 541-610 of SEQ ID NO:2. In embodiments, the RNA sequence has at least 80% sequence identity to the complement of at least 15 consecutive nucleotides of nucleotides 541-609 of SEQ ID NO:2. In embodiments, the RNA sequence has at least 80% sequence identity to the complement of at least 15 consecutive nucleotides of nucleotides 541-608 of SEQ ID NO:2. In embodiments, the RNA sequence has at least 80% sequence identity to the complement of at least 15 consecutive nucleotides of nucleotides 541-607 of SEQ ID NO:2. In embodiments, the RNA sequence has at least 80% sequence identity to the complement of at least 15 consecutive nucleotides of nucleotides 541-606 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 541-612, 541-611, 541-610, 541-609, 541-608, 541-607, or 541-606 of SEQ ID NO:2.

In embodiments, the RNA sequence has at least 80% sequence identity to the complement of at least 15 consecutive nucleotides of nucleotides 541-605 of SEQ ID NO:2. In embodiments, the RNA sequence has at least 80% sequence identity to the complement of at least 15 consecutive nucleotides of nucleotides 541-604 of SEQ ID NO:2. In embodiments, the RNA sequence has at least 80% sequence identity to the complement of at least 15 consecutive nucleotides of nucleotides 541-603 of SEQ ID NO:2. In embodiments, the RNA sequence has at least 80% sequence identity to the complement of at least 15 consecutive nucleotides of nucleotides 541-602 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 541-605, 541-604, 541-603, or 541-602 of SEQ ID NO:2.0135

In embodiments, the RNA sequence hybridizes to nucleotides 57-77 of SEQ ID NO:2. In embodiments, the RNA sequence hybridizes to nucleotides 236-256 of SEQ ID NO:2. In embodiments, the RNA sequence hybridizes to nucleotides 287-307 of SEQ ID NO:2. In embodiments, the RNA sequence hybridizes to nucleotides 515-535 of SEQ ID NO:2. In embodiments, the RNA sequence hybridizes to nucleotides 582-602 of SEQ ID NO:2.

In embodiments, the RNA sequence has at least 97% sequence identity to the complement of at least 15 consecutive nucleotides of nucleotides 57-77 of SEQ ID NO:2. In embodiments, the RNA sequence has at least 97% sequence identity to the complement of at least 15 consecutive nucleotides of nucleotides 55-77 of SEQ ID NO:2. In embodiments, the RNA sequence has at least 97% sequence identity to the complement of at least 15 consecutive nucleotides of nucleotides 50-77 of SEQ ID NO:2. In embodiments, the RNA sequence has at least 97% sequence identity to the complement of at least 15 consecutive nucleotides of nucleotides 45-77 of SEQ ID NO:2.

In embodiments, the RNA sequence has at least 97% sequence identity to the complement of at least 15 consecutive nucleotides of nucleotides 57-80 of SEQ ID NO:2. In embodiments, the RNA sequence has at least 97% sequence identity to the complement of at least 15 consecutive nucleotides of nucleotides 57-85 of SEQ ID NO:2. In embodiments, the RNA sequence has at least 97% sequence identity to the complement of at least 15 consecutive nucleotides of nucleotides 57-90 of SEQ ID NO:2. In embodiments, the RNA sequence has at least 97% sequence identity to the complement of at least 15 consecutive nucleotides of nucleotides 57-95 of SEQ ID NO:2.

In embodiments, the RNA sequence has at least 90% sequence identity to the complement of at least 15 consecutive nucleotides of nucleotides 236-256 of SEQ ID NO:2. In embodiments, the RNA sequence has at least 90% sequence identity to the complement of at least 15 consecutive nucleotides of nucleotides 230-256 of SEQ ID NO:2. In embodiments, the RNA sequence has at least 90% sequence identity to the complement of at least 15 consecutive nucleotides of nucleotides 225-256 of SEQ ID NO:2. In embodiments, the RNA sequence has at least 90% sequence identity to the complement of at least 15 consecutive nucleotides of nucleotides 220-256 of SEQ ID NO:2.

In embodiments, the RNA sequence has at least 90% sequence identity to the complement of at least 15 consecutive nucleotides of nucleotides 236-260 of SEQ ID NO:2. In embodiments, the RNA sequence has at least 90% sequence identity to the complement of at least 15 consecutive nucleotides of nucleotides 236-265 of SEQ ID NO:2. In embodiments, the RNA sequence has at least 90% sequence identity to the complement of at least 15 consecutive nucleotides of nucleotides 236-270 of SEQ ID NO:2. In embodiments, the RNA sequence has at least 90% sequence identity to the complement of at least 15 consecutive nucleotides of nucleotides 236-275 of SEQ ID NO:2.

In embodiments, the RNA sequence has at least 97% sequence identity to the complement of at least 15 consecutive nucleotides of nucleotides 236-256 of SEQ ID NO:2. In embodiments, the RNA sequence has at least 97% sequence identity to the complement of at least 15 consecutive nucleotides of nucleotides 230-256 of SEQ ID NO:2. In embodiments, the RNA sequence has at least 97% sequence identity to the complement of at least 15 consecutive nucleotides of nucleotides 225-256 of SEQ ID NO:2. In embodiments, the RNA sequence has at least 97% sequence identity to the complement of at least 15 consecutive nucleotides of nucleotides 220-256 of SEQ ID NO:2.

In embodiments, the RNA sequence has at least 97% sequence identity to the complement of at least 15 consecutive nucleotides of nucleotides 236-260 of SEQ ID NO:2. In embodiments, the RNA sequence has at least 97% sequence identity to the complement of at least 15 consecutive nucleotides of nucleotides 236-265 of SEQ ID NO:2. In embodiments, the RNA sequence has at least 97% sequence identity to the complement of at least 15 consecutive nucleotides of nucleotides 236-270 of SEQ ID NO:2. In embodiments, the RNA sequence has at least 97% sequence identity to the complement of at least 15 consecutive nucleotides of nucleotides 236-275 of SEQ ID NO:2.

In embodiments, the RNA sequence has at least 90% sequence identity to the complement of at least 15 consecutive nucleotides of nucleotides 287-307 of SEQ ID NO:2. In embodiments, the RNA sequence has at least 90% sequence identity to the complement of at least 15 consecutive nucleotides of nucleotides 285-307 of SEQ ID NO:2. In embodiments, the RNA sequence has at least 90% sequence identity to the complement of at least 15 consecutive nucleotides of nucleotides 280-307 of SEQ ID NO:2. In embodiments, the RNA sequence has at least 90% sequence identity to the complement of at least 15 consecutive nucleotides of nucleotides 275-307 of SEQ ID NO:2.

In embodiments, the RNA sequence has at least 90% sequence identity to the complement of at least 15 consecutive nucleotides of nucleotides 287-310 of SEQ ID NO:2. In embodiments, the RNA sequence has at least 90% sequence identity to the complement of at least 15 consecutive nucleotides of nucleotides 287-315 of SEQ ID NO:2. In embodiments, the RNA sequence has at least 90% sequence identity to the complement of at least 15 consecutive nucleotides of nucleotides 287-320 of SEQ ID NO:2. In embodiments, the RNA sequence has at least 90% sequence identity to the complement of at least 15 consecutive nucleotides of nucleotides 287-325 of SEQ ID NO:2.

In embodiments, the RNA sequence has at least 97% sequence identity to the complement of at least 15 consecutive nucleotides of nucleotides 287-307 of SEQ ID NO:2. In embodiments, the RNA sequence has at least 97% sequence identity to the complement of at least 15 consecutive nucleotides of nucleotides 285-307 of SEQ ID NO:2. In embodiments, the RNA sequence has at least 97% sequence identity to the complement of at least 15 consecutive nucleotides of nucleotides 280-307 of SEQ ID NO:2. In embodiments, the RNA sequence has at least 97% sequence identity to the complement of at least 15 consecutive nucleotides of nucleotides 275-307 of SEQ ID NO:2.

In embodiments, the RNA sequence has at least 97% sequence identity to the complement of at least 15 consecutive nucleotides of nucleotides 287-310 of SEQ ID NO:2. In embodiments, the RNA sequence has at least 97% sequence identity to the complement of at least 15 consecutive nucleotides of nucleotides 287-315 of SEQ ID NO:2. In embodiments, the RNA sequence has at least 97% sequence identity to the complement of at least 15 consecutive nucleotides of nucleotides 287-320 of SEQ ID NO:2. In embodiments, the RNA sequence has at least 97% sequence identity to the complement of at least 15 consecutive nucleotides of nucleotides 287-325 of SEQ ID NO:2.

In embodiments, the RNA sequence has at least 90% sequence identity to the complement of at least 15 consecutive nucleotides of nucleotides 515-535 of SEQ ID NO:2. In embodiments, the RNA sequence has at least 90% sequence identity to the complement of at least 15 consecutive nucleotides of nucleotides 510-535 of SEQ ID NO:2. In embodiments, the RNA sequence has at least 90% sequence identity to the complement of at least 15 consecutive nucleotides of nucleotides 505-535 of SEQ ID NO:2. In embodiments, the RNA sequence has at least 90% sequence identity to the complement of at least 15 consecutive nucleotides of nucleotides 500-535 of SEQ ID NO:2.

In embodiments, the RNA sequence has at least 90% sequence identity to the complement of at least 15 consecutive nucleotides of nucleotides 515-540 of SEQ ID NO:2. In embodiments, the RNA sequence has at least 90% sequence identity to the complement of at least 15 consecutive nucleotides of nucleotides 515-545 of SEQ ID NO:2. In embodiments, the RNA sequence has at least 90% sequence identity to the complement of at least 15 consecutive nucleotides of nucleotides 515-550 of SEQ ID NO:2. In embodiments, the RNA sequence has at least 90% sequence identity to the complement of at least 15 consecutive nucleotides of nucleotides 515-555 of SEQ ID NO:2.

In embodiments, the RNA sequence has at least 97% sequence identity to the complement of at least 15 consecutive nucleotides of nucleotides 515-535 of SEQ ID NO:2. In embodiments, the RNA sequence has at least 97% sequence identity to the complement of at least 15 consecutive nucleotides of nucleotides 510-535 of SEQ ID NO:2. In embodiments, the RNA sequence has at least 97% sequence identity to the complement of at least 15 consecutive nucleotides of nucleotides 505-535 of SEQ ID NO:2. In embodiments, the RNA sequence has at least 97% sequence identity to the complement of at least 15 consecutive nucleotides of nucleotides 500-535 of SEQ ID NO:2.

In embodiments, the RNA sequence has at least 97% sequence identity to the complement of at least 15 consecutive nucleotides of nucleotides 515-540 of SEQ ID NO:2. In embodiments, the RNA sequence has at least 97% sequence identity to the complement of at least 15 consecutive nucleotides of nucleotides 515-545 of SEQ ID NO:2. In embodiments, the RNA sequence has at least 97% sequence identity to the complement of at least 15 consecutive nucleotides of nucleotides 515-550 of SEQ ID NO:2. In embodiments, the RNA sequence has at least 97% sequence identity to the complement of at least 15 consecutive nucleotides of nucleotides 515-555 of SEQ ID NO:2.

In embodiments, the RNA sequence has at least 90% sequence identity to the complement of at least 15 consecutive nucleotides of nucleotides 582-602 of SEQ ID NO:2. In embodiments, the RNA sequence has at least 90% sequence identity to the complement of at least 15 consecutive nucleotides of nucleotides 580-602 of SEQ ID NO:2. In embodiments, the RNA sequence has at least 90% sequence identity to the complement of at least 15 consecutive nucleotides of nucleotides 575-602 of SEQ ID NO:2. In embodiments, the RNA sequence has at least 90% sequence identity to the complement of at least 15 consecutive nucleotides of nucleotides 570-602 of SEQ ID NO:2. In embodiments, the RNA sequence has at least 90% sequence identity to the complement of at least 15 consecutive nucleotides of nucleotides 565-602 of SEQ ID NO:2. In embodiments, the RNA sequence has at least 90% sequence identity to the complement of at least 15 consecutive nucleotides of nucleotides 560-602 of SEQ ID NO:2.

In embodiments, the RNA sequence has at least 90% sequence identity to the complement of at least 15 consecutive nucleotides of nucleotides 582-605 of SEQ ID NO:2. In embodiments, the RNA sequence has at least 90% sequence identity to the complement of at least 15 consecutive nucleotides of nucleotides 582-610 of SEQ ID NO:2. In embodiments, the RNA sequence has at least 90% sequence identity to the complement of at least 15 consecutive nucleotides of nucleotides 582-610 of SEQ ID NO:2. In embodiments, the RNA sequence has at least 90% sequence identity to the complement of at least 15 consecutive nucleotides of nucleotides 582-615 of SEQ ID NO:2. In embodiments, the RNA sequence has at least 90% sequence identity to the complement of at least 15 consecutive nucleotides of nucleotides 582-620 of SEQ ID NO:2. In embodiments, the RNA sequence has at least 90% sequence identity to the complement of at least 15 consecutive nucleotides of nucleotides 582-625 of SEQ ID NO:2.

In embodiments, the RNA sequence has at least 97% sequence identity to the complement of at least 15 consecutive nucleotides of nucleotides 582-602 of SEQ ID NO:2. In embodiments, the RNA sequence has at least 97% sequence identity to the complement of at least 15 consecutive nucleotides of nucleotides 580-602 of SEQ ID NO:2. In embodiments, the RNA sequence has at least 97% sequence identity to the complement of at least 15 consecutive nucleotides of nucleotides 575-602 of SEQ ID NO:2. In embodiments, the RNA sequence has at least 97% sequence identity to the complement of at least 15 consecutive nucleotides of nucleotides 570-602 of SEQ ID NO:2. In embodiments, the RNA sequence has at least 97% sequence identity to the complement of at least 15 consecutive nucleotides of nucleotides 565-602 of SEQ ID NO:2. In embodiments, the RNA sequence has at least 97% sequence identity to the complement of at least 15 consecutive nucleotides of nucleotides 560-602 of SEQ ID NO:2.

In embodiments, the RNA sequence has at least 97% sequence identity to the complement of at least 15 consecutive nucleotides of nucleotides 582-605 of SEQ ID NO:2. In embodiments, the RNA sequence has at least 97% sequence identity to the complement of at least 15 consecutive nucleotides of nucleotides 582-610 of SEQ ID NO:2. In embodiments, the RNA sequence has at least 97% sequence identity to the complement of at least 15 consecutive nucleotides of nucleotides 582-610 of SEQ ID NO:2. In embodiments, the RNA sequence has at least 97% sequence identity to the complement of at least 15 consecutive nucleotides of nucleotides 582-615 of SEQ ID NO:2. In embodiments, the RNA sequence has at least 97% sequence identity to the complement of at least 15 consecutive nucleotides of nucleotides 582-620 of SEQ ID NO:2. In embodiments, the RNA sequence has at least 97% sequence identity to the complement of at least 15 consecutive nucleotides of nucleotides 582-625 of SEQ ID NO:2.

The ribonucleic acid compounds as described herein including embodiments thereof, are composed of nucleotides capable of forming base pairs with a target RNA (e.g, lncRNA or lncRNA promoter sequence). Thus, the ribonucleic nucleic acid compounds described herein including embodiments thereof, are complementary to the target RNA (lncRNA or lncRNA promoter sequence) and can bind (hybridize) with portions of the target RNA sequence. In embodiments, the RNA sequence is capable of hybridizing to at least 15 (e.g., 16, 17, 18, 19, 20, or 21) consecutive nucleotides of nucleotides 541-631 of SEQ ID NO:2. In embodiments, the RNA sequence is capable of hybridizing to 15 consecutive nucleotides of nucleotides 541-631 of SEQ ID NO:2. In embodiments, the RNA sequence is capable of hybridizing to 16 consecutive nucleotides of nucleotides 541-631 of SEQ ID NO:2. In embodiments, the RNA sequence is capable of hybridizing to 17 consecutive nucleotides of nucleotides 541-631 of SEQ ID NO:2 In embodiments, the RNA sequence is capable of hybridizing to 18 consecutive nucleotides of nucleotides 541-631 of SEQ ID NO:2. In embodiments, the RNA sequence is capable of hybridizing to 19 consecutive nucleotides of nucleotides 541-631 of SEQ ID NO:2. In embodiments, the RNA sequence is capable of hybridizing to 20 consecutive nucleotides of nucleotides 541-631 of SEQ ID NO:2. In embodiments, the RNA sequence is capable of hybridizing to 21 consecutive nucleotides of nucleotides 541-631 of SEQ ID NO:2. In embodiments, the RNA sequence is capable of hybridizing to 22 consecutive nucleotides of nucleotides 541-631 of SEQ ID NO:2. In embodiments, the RNA sequence is capable of hybridizing to 23 consecutive nucleotides of nucleotides 541-631 of SEQ ID NO:2. In embodiments, the RNA sequence is capable of hybridizing to 24 consecutive nucleotides of nucleotides 541-631 of SEQ ID NO:2. In embodiments, the RNA sequence is capable of hybridizing to 25 consecutive nucleotides of nucleotides 541-631 of SEQ ID NO:2. In embodiments, the RNA sequence is capable of hybridizing to 26 consecutive nucleotides of nucleotides 541-631 of SEQ ID NO:2. In embodiments, the RNA sequence is capable of hybridizing to 27 consecutive nucleotides of nucleotides 541-631 of SEQ ID NO:2. In embodiments, the RNA sequence is capable of hybridizing to 28 consecutive nucleotides of nucleotides 541-631 of SEQ ID NO:2. In embodiments, the RNA sequence is capable of hybridizing to 29 consecutive nucleotides of nucleotides 541-631 of SEQ ID NO:2. In embodiments, the RNA sequence is capable of hybridizing to 30 consecutive nucleotides of nucleotides 541-631 of SEQ ID NO:2. In embodiments, the RNA sequence is capable of hybridizing to 35 consecutive nucleotides of nucleotides 541-631 of SEQ ID NO:2. In embodiments, the RNA sequence is capable of hybridizing to 40 consecutive nucleotides of nucleotides 541-631 of SEQ ID NO:2. In embodiments, the RNA sequence is capable of hybridizing to 45 consecutive nucleotides of nucleotides 541-631 of SEQ ID NO:2. In embodiments, the RNA sequence is capable of hybridizing to 50 consecutive nucleotides of nucleotides 541-631 of SEQ ID NO:2.

In embodiments, the RNA sequence is capable of hybridizing to about 15, 16, 17, 18, 19, 20, 21, 22, 23, 24 or 25 consecutive nucleotides of nucleotides 541-631 of SEQ ID NO:2. In embodiments, the RNA sequence is capable of hybridizing to about 15 consecutive nucleotides of nucleotides 541-631 of SEQ ID NO:2. In embodiments, the RNA sequence is capable of hybridizing to about 16 consecutive nucleotides of nucleotides 541-631 of SEQ ID NO:2. In embodiments, the RNA sequence is capable of hybridizing to about 17 consecutive nucleotides of nucleotides 541-631 of SEQ ID NO:2. In embodiments, the RNA sequence is capable of hybridizing to about 18 consecutive nucleotides of nucleotides 541-631 of SEQ ID NO:2. In embodiments, the RNA sequence is capable of hybridizing to about 19 consecutive nucleotides of nucleotides 541-631 of SEQ ID NO:2. In embodiments, the RNA sequence is capable of hybridizing to about 20 consecutive nucleotides of nucleotides 541-631 of SEQ ID NO:2. In embodiments, the RNA sequence is capable of hybridizing to about 21 consecutive nucleotides of nucleotides 541-631 of SEQ ID NO:2. In embodiments, the RNA sequence is capable of hybridizing to about 22 consecutive nucleotides of nucleotides 541-631 of SEQ ID NO:2. In embodiments, the RNA sequence is capable of hybridizing to about 23 consecutive nucleotides of nucleotides 541-631 of SEQ ID NO:2. In embodiments, the RNA sequence is capable of hybridizing to about 24 consecutive nucleotides of nucleotides 541-631 of SEQ ID NO:2. In embodiments, the RNA sequence is capable of hybridizing to about 25 consecutive nucleotides of nucleotides 541-631 of SEQ ID NO:2. In embodiments, the RNA sequence is capable of hybridizing to about 26 consecutive nucleotides of nucleotides 541-631 of SEQ ID NO:2. In embodiments, the RNA sequence is capable of hybridizing to about 27 consecutive nucleotides of nucleotides 541-631 of SEQ ID NO:2. In embodiments, the RNA sequence is capable of hybridizing to about 28 consecutive nucleotides of nucleotides 541-631 of SEQ ID NO:2. In embodiments, the RNA sequence is capable of hybridizing to about 29 consecutive nucleotides of nucleotides 541-631 of SEQ ID NO:2. In embodiments, the RNA sequence is capable of hybridizing to about 30 consecutive nucleotides of nucleotides 541-631 of SEQ ID NO:2. In embodiments, the RNA sequence is capable of hybridizing to about 31 consecutive nucleotides of nucleotides 541-631 of SEQ ID NO:2. In embodiments, the RNA sequence is capable of hybridizing to about 32 consecutive nucleotides of nucleotides 541-631 of SEQ ID NO:2. In embodiments, the RNA sequence is capable of hybridizing to about 33 consecutive nucleotides 2 of nucleotides 541-631 of SEQ ID NO:2. In embodiments, the RNA sequence is capable of hybridizing to about 34 consecutive nucleotides of nucleotides 541-631 of SEQ ID NO:2.

In embodiments, the RNA sequence is capable of hybridizing to about 35 consecutive nucleotides of nucleotides 541-631 of SEQ ID NO:2. In embodiments, the RNA sequence is capable of hybridizing to about 36 consecutive nucleotides of nucleotides 541-631 of SEQ ID NO:2. In embodiments, the RNA sequence is capable of hybridizing to about 37 consecutive nucleotides of nucleotides 541-631 of SEQ ID NO:2. In embodiments, the RNA sequence is capable of hybridizing to about 38 consecutive nucleotides of nucleotides 541-631 of SEQ ID NO:2. In embodiments, the RNA sequence is capable of hybridizing to about 39 consecutive nucleotides of nucleotides 541-631 of SEQ ID NO:2. In embodiments, the RNA sequence is capable of hybridizing to about 40 consecutive nucleotides of nucleotides 541-631 of SEQ ID NO:2. In embodiments, the RNA sequence is capable of hybridizing to about 41 consecutive nucleotides of nucleotides 541-631 of SEQ ID NO:2. In embodiments, the RNA sequence is capable of hybridizing to about 42 consecutive nucleotides of nucleotides 541-631 of SEQ ID NO:2. In embodiments, the RNA sequence is capable of hybridizing to about 43 consecutive nucleotides of nucleotides 541-631 of SEQ ID NO:2. In embodiments, the RNA sequence is capable of hybridizing to about 44 consecutive nucleotides of nucleotides 541-631 of SEQ ID NO:2. In embodiments, the RNA sequence is capable of hybridizing to about 45 consecutive nucleotides of nucleotides 541-631 of SEQ ID NO:2.

In embodiments, the RNA sequence is capable of hybridizing to about 46 consecutive nucleotides of nucleotides 541-631 of SEQ ID NO:2. In embodiments, the RNA sequence is capable of hybridizing to about 47 consecutive nucleotides of nucleotides 541-631 of SEQ ID NO:2. In embodiments, the RNA sequence is capable of hybridizing to about 48 consecutive nucleotides of nucleotides 541-631 of SEQ ID NO:2. In embodiments, the RNA sequence is capable of hybridizing to about 49 consecutive nucleotides of nucleotides 541-631 of SEQ ID NO:2. In embodiments, the RNA sequence is capable of hybridizing to about 50 consecutive nucleotides of nucleotides 541-631 of SEQ ID NO:2.

In embodiments, the RNA sequence is capable of hybridizing to 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of nucleotides 541-631 of SEQ ID NO:2.

In embodiments, the RNA sequence is capable of hybridizing to 21 consecutive nucleotides of nucleotides 541-631 of SEQ ID NO:2. In embodiments, the RNA sequence has at least 85% sequence identity to the complement of the consecutive nucleotides. In embodiments, the RNA sequence has at least 86% sequence identity to the complement of the consecutive nucleotides. In embodiments, the RNA sequence has at least 87% sequence identity to the complement of the consecutive nucleotides. In embodiments, the RNA sequence has at least 88% sequence identity to the complement of the consecutive nucleotides. In embodiments, the RNA sequence has at least 89% sequence identity to the complement of the consecutive nucleotides. In embodiments, the RNA sequence has at least 90% sequence identity to the complement of the consecutive nucleotides. In embodiments, the RNA sequence has at least 91% sequence identity to the complement of the consecutive nucleotides. In embodiments, the RNA sequence has at least 92% sequence identity to the complement of the consecutive nucleotides. In embodiments, the RNA sequence has at least 93% sequence identity to the complement of the consecutive nucleotides. In embodiments, the RNA sequence has at least 94% sequence identity to the complement of the consecutive nucleotides. In embodiments, the RNA sequence has at least 95% sequence identity to the complement of the consecutive nucleotides. In embodiments, the RNA sequence has at least 96% sequence identity to the complement of the consecutive nucleotides. In embodiments, the RNA sequence has at least 97% sequence identity to the complement of the consecutive nucleotides. In embodiments, the RNA sequence has at least 98% sequence identity to the complement of the consecutive nucleotides. In embodiments, the RNA sequence has at least 99% sequence identity to the complement of the consecutive nucleotides.

In embodiments, the RNA sequence is capable of hybridizing to 21 consecutive nucleotides of nucleotides 541-631 of SEQ ID NO:2. In embodiments, the RNA sequence has about 85% sequence identity to the complement of the consecutive nucleotides. In embodiments, the RNA sequence has about 86% sequence identity to the complement of the consecutive nucleotides. In embodiments, the RNA sequence has about 87% sequence identity to the complement of the consecutive nucleotides. In embodiments, the RNA sequence has about 88% sequence identity to the complement of the consecutive nucleotides. In embodiments, the RNA sequence has about 89% sequence identity to the complement of the consecutive nucleotides. In embodiments, the RNA sequence has about 90% sequence identity to the complement of the consecutive nucleotides. In embodiments, the RNA sequence has about 91% sequence identity to the complement of the consecutive nucleotides. In embodiments, the RNA sequence has about 92% sequence identity to the complement of the consecutive nucleotides. In embodiments, the RNA sequence has about 93% sequence identity to the complement of the consecutive nucleotides. In embodiments, the RNA sequence has about 94% sequence identity to the complement of the consecutive nucleotides. In embodiments, the RNA sequence has about 95% sequence identity to the complement of the consecutive nucleotides. In embodiments, the RNA sequence has about 96% sequence identity to the complement of the consecutive nucleotides. In embodiments, the RNA sequence has about 97% sequence identity to the complement of the consecutive nucleotides. In embodiments, the RNA sequence has about 98% sequence identity to the complement of the consecutive nucleotides. In embodiments, the RNA sequence has about 99% sequence identity to the complement of the consecutive nucleotides.

In embodiments, the RNA sequence is capable of hybridizing to 21 consecutive nucleotides of nucleotides 541-631 of SEQ ID NO:2. In embodiments, the RNA sequence has 85% sequence identity to the complement of the consecutive nucleotides. In embodiments, the RNA sequence has 86% sequence identity to the complement of the consecutive nucleotides. In embodiments, the RNA sequence has 87% sequence identity to the complement of the consecutive nucleotides. In embodiments, the RNA sequence has 88% sequence identity to the complement of the consecutive nucleotides. In embodiments, the RNA sequence has 89% sequence identity to the complement of the consecutive nucleotides. In embodiments, the RNA sequence has 90% sequence identity to the complement of the consecutive nucleotides. In embodiments, the RNA sequence has 91% sequence identity to the complement of the consecutive nucleotides. In embodiments, the RNA sequence has 92% sequence identity to the complement of the consecutive nucleotides. In embodiments, the RNA sequence has 93% sequence identity to the complement of the consecutive nucleotides. In embodiments, the RNA sequence has 94% sequence identity to the complement of the consecutive nucleotides. In embodiments, the RNA sequence has 95% sequence identity to the complement of the consecutive nucleotides. In embodiments, the RNA sequence has 96% sequence identity to the complement of the consecutive nucleotides. In embodiments, the RNA sequence has 97% sequence identity to the complement of the consecutive nucleotides. In embodiments, the RNA sequence has 98% sequence identity to the complement of the consecutive nucleotides. In embodiments, the RNA sequence has 99% sequence identity to the complement of the consecutive nucleotides. In embodiments, the RNA sequence has 100% sequence identity to the complement of the consecutive nucleotides.

In embodiments, the RNA sequence is capable of hybridizing to nucleotides 582-602 of SEQ ID NO:2. In embodiments, the RNA sequence has at least 80% sequence identity to the complement of SEQ ID NO:2. In embodiments, the RNA sequence has at least 85% sequence identity to the complement of SEQ ID NO:2. In embodiments, the RNA sequence has at least 86% sequence identity to the complement of SEQ ID NO:2. In embodiments, the RNA sequence has at least 87% sequence identity to the complement of SEQ ID NO:2. In embodiments, the RNA sequence has at least 88% sequence identity to the complement of SEQ ID NO:2. In embodiments, the RNA sequence has at least 89% sequence identity to the complement of SEQ ID NO:2. In embodiments, the RNA sequence has at least 90% sequence identity to the complement of SEQ ID NO:2. In embodiments, the RNA sequence has at least 91% sequence identity to the complement of SEQ ID NO:2. In embodiments, the RNA sequence has at least 92% sequence identity to the complement of SEQ ID NO:2. In embodiments, the RNA sequence has at least 93% sequence identity to the complement of SEQ ID NO:2. In embodiments, the RNA sequence has at least 94% sequence identity to the complement of SEQ ID NO:2. In embodiments, the RNA sequence has at least 95% sequence identity to the complement of SEQ ID NO:2. In embodiments, the RNA sequence has at least 97% sequence identity to the complement of SEQ ID NO:2. In embodiments, the RNA sequence has at least 98% sequence identity to the complement of SEQ ID NO:2. In embodiments, the RNA sequence has at least 99% sequence identity to the complement of SEQ ID NO:2. In embodiments, the RNA sequence is SEQ ID NO:18. In embodiments, the RNA sequence includes SEQ ID NO:18.

In embodiments, the RNA sequence is capable of hybridizing to nucleotides 582-602 of SEQ ID NO:2. In embodiments, the RNA sequence has about 80% sequence identity to the complement of SEQ ID NO:2. In embodiments, the RNA sequence has about 85% sequence identity to the complement of SEQ ID NO:2. In embodiments, the RNA sequence has about 86% sequence identity to the complement of SEQ ID NO:2. In embodiments, the RNA sequence has about 87% sequence identity to the complement of SEQ ID NO:2. In embodiments, the RNA sequence has about 88% sequence identity to the complement of SEQ ID NO:2. In embodiments, the RNA sequence has about 89% sequence identity to the complement of SEQ ID NO:2. In embodiments, the RNA sequence has about 90% sequence identity to the complement of SEQ ID NO:2. In embodiments, the RNA sequence has about 91% sequence identity to the complement of SEQ ID NO:2. In embodiments, the RNA sequence has about 92% sequence identity to the complement of SEQ ID NO:2. In embodiments, the RNA sequence has about 93% sequence identity to the complement of SEQ ID NO:2. In embodiments, the RNA sequence has about 94% sequence identity to the complement of SEQ ID NO:2. In embodiments, the RNA sequence has about 95% sequence identity to the complement of SEQ ID NO:2. In embodiments, the RNA sequence has about 97% sequence identity to the complement of SEQ ID NO:2. In embodiments, the RNA sequence has about 98% sequence identity to the complement of SEQ ID NO:2. In embodiments, the RNA sequence has about 99% sequence identity to the complement of SEQ ID NO:2. In embodiments, the RNA sequence is SEQ ID NO:18. In embodiments, the RNA sequence includes SEQ ID NO:18.

In embodiments, the RNA sequence is capable of hybridizing to nucleotides 582-602 of SEQ ID NO:2. In embodiments, the RNA sequence has 80% sequence identity to the complement of SEQ ID NO:2. In embodiments, the RNA sequence has 85% sequence identity to the complement of SEQ ID NO:2. In embodiments, the RNA sequence has 86% sequence identity to the complement of SEQ ID NO:2. In embodiments, the RNA sequence has 87% sequence identity to the complement of SEQ ID NO:2. In embodiments, the RNA sequence has 88% sequence identity to the complement of SEQ ID NO:2. In embodiments, the RNA sequence has 89% sequence identity to the complement of SEQ ID NO:2. In embodiments, the RNA sequence has 90% sequence identity to the complement of SEQ ID NO:2. In embodiments, the RNA sequence has 91% sequence identity to the complement of SEQ ID NO:2. In embodiments, the RNA sequence has 92% sequence identity to the complement of SEQ ID NO:2. In embodiments, the RNA sequence has 93% sequence identity to the complement of SEQ ID NO:2. In embodiments, the RNA sequence has 94% sequence identity to the complement of SEQ ID NO:2. In embodiments, the RNA sequence has 95% sequence identity to the complement of SEQ ID NO:2. In embodiments, the RNA sequence has 97% sequence identity to the complement of SEQ ID NO:2. In embodiments, the RNA sequence has 98% sequence identity to the complement of SEQ ID NO:2. In embodiments, the RNA sequence has 99% sequence identity to the complement of SEQ ID NO:2.

In embodiments, the RNA sequence is SEQ ID NO:18. In embodiments, the RNA sequence includes SEQ ID NO:18. In embodiments, the RNA sequence is SEQ ID NOs:17 and 18. In embodiments, the RNA sequence includes SEQ ID NOs:17 and 18. In embodiments, the RNA sequence is SEQ ID NO:22. In embodiments, the RNA sequence includes SEQ ID NO:22. In embodiments, the RNA sequence is SEQ ID NO:21. In embodiments, the RNA sequence includes SEQ ID NO:21. In embodiments, the RNA sequence is SEQ ID NOs:21 and 22. In embodiments, the RNA sequence includes SEQ ID NOs:21 and 22.

In embodiments, the RNA sequence is a single-stranded RNA sequence. In embodiments, the RNA sequence is a double-stranded RNA sequence. In embodiments, the RNA sequence is an LDLR-activating sequence. In embodiments, the RNA sequence is a siRNA. In embodiments, the RNA sequence is a post-transcriptional gene silencing (PTGS) RNA.

In another aspect, there is provided a ribonucleic acid compound including an RNA sequence, the RNA sequence having at least 80% sequence identity to the complement of at least 15 consecutive nucleotides of nucleotides 1-120 of SEQ ID NO:2. In embodiments, the RNA sequence has at least 85% sequence identity to the complement of at least 15 consecutive nucleotides of nucleotides 1-120 of SEQ ID NO:2. In embodiments, the RNA sequence has at least 86% sequence identity to the complement of at least 15 consecutive nucleotides of nucleotides 1-120 of SEQ ID NO:2. In embodiments, the RNA sequence has at least 87% sequence identity to the complement of at least 15 consecutive nucleotides of nucleotides 1-120 of SEQ ID NO:2. In embodiments, the RNA sequence has at least 88% sequence identity to the complement of at least 15 consecutive nucleotides of nucleotides 1-120 of SEQ ID NO:2. In embodiments, the RNA sequence has at least 89% sequence identity to the complement of at least 15 consecutive nucleotides of nucleotides 1-120 of SEQ ID NO:2. In embodiments, the RNA sequence has at least 90% sequence identity to the complement of at least 15 consecutive nucleotides of nucleotides 1-120 of SEQ ID NO:2. In embodiments, the RNA sequence has at least 91% sequence identity to the complement of at least 15 consecutive nucleotides of nucleotides 1-120 of SEQ ID NO:2. In embodiments, the RNA sequence has at least 92% sequence identity to the complement of at least 15 consecutive nucleotides of nucleotides 1-120 of SEQ ID NO:2. In embodiments, the RNA sequence has at least 93% sequence identity to the complement of at least 15 consecutive nucleotides of nucleotides 1-120 of SEQ ID NO:2. In embodiments, the RNA sequence has at least 94% sequence identity to the complement of at least 15 consecutive nucleotides of nucleotides 1-120 of SEQ ID NO:2. In embodiments, the RNA sequence has at least 95% sequence identity to the complement of at least 15 consecutive nucleotides of nucleotides 1-120 of SEQ ID NO:2. In embodiments, the RNA sequence has at least 96% sequence identity to the complement of at least 15 consecutive nucleotides of nucleotides 1-120 of SEQ ID NO:2. In embodiments, the RNA sequence has at least 97% sequence identity to the complement of at least 15 consecutive nucleotides of nucleotides 1-120 of SEQ ID NO:2. In embodiments, the RNA sequence has at least 98% sequence identity to the complement of at least 15 consecutive nucleotides of nucleotides 1-120 of SEQ ID NO:2. In embodiments, the RNA sequence has at least 99% sequence identity to the complement of at least 15 consecutive nucleotides of nucleotides 1-120 of SEQ ID NO:2.

In embodiments, the RNA sequence has 80% sequence identity to the complement of at least 15 consecutive nucleotides of nucleotides 1-120 of SEQ ID NO:2. In embodiments, the RNA sequence has 85% sequence identity to the complement of at least 15 consecutive nucleotides of nucleotides 1-120 of SEQ ID NO:2. In embodiments, the RNA sequence has 86% sequence identity to the complement of at least 15 consecutive nucleotides of nucleotides 1-120 of SEQ ID NO:2. In embodiments, the RNA sequence has 87% sequence identity to the complement of at least 15 consecutive nucleotides of nucleotides 1-120 of SEQ ID NO:2. In embodiments, the RNA sequence has 88% sequence identity to the complement of at least 15 consecutive nucleotides of nucleotides 1-120 of SEQ ID NO:2. In embodiments, the RNA sequence has 89% sequence identity to the complement of at least 15 consecutive nucleotides of nucleotides 1-120 of SEQ ID NO:2. In embodiments, the RNA sequence has 90% sequence identity to the complement of at least 15 consecutive nucleotides of nucleotides 1-120 of SEQ ID NO:2. In embodiments, the RNA sequence has 91% sequence identity to the complement of at least 15 consecutive nucleotides of nucleotides 1-120 of SEQ ID NO:2. In embodiments, the RNA sequence has 92% sequence identity to the complement of at least 15 consecutive nucleotides of nucleotides 1-120 of SEQ ID NO:2. In embodiments, the RNA sequence has 93% sequence identity to the complement of at least 15 consecutive nucleotides of nucleotides 1-120 of SEQ ID NO:2. In embodiments, the RNA sequence has 94% sequence identity to the complement of at least 15 consecutive nucleotides of nucleotides 1-120 of SEQ ID NO:2. In embodiments, the RNA sequence has 95% sequence identity to the complement of at least 15 consecutive nucleotides of nucleotides 1-120 of SEQ ID NO:2. In embodiments, the RNA sequence has 96% sequence identity to the complement of at least 15 consecutive nucleotides of nucleotides 1-120 of SEQ ID NO:2. In embodiments, the RNA sequence has 97% sequence identity to the complement of at least 15 consecutive nucleotides of nucleotides 1-120 of SEQ ID NO:2. In embodiments, the RNA sequence has 98% sequence identity to the complement of at least 15 consecutive nucleotides of nucleotides 1-120 of SEQ ID NO:2. In embodiments, the RNA sequence has 99% sequence identity to the complement of at least 15 consecutive nucleotides of nucleotides 1-120 of SEQ ID NO:2.

In embodiments, the RNA sequence has 80% sequence identity to the complement of 15 consecutive nucleotides of nucleotides 1-120 of SEQ ID NO:2. In embodiments, the RNA sequence has 85% sequence identity to the complement of 15 consecutive nucleotides of nucleotides 1-120 of SEQ ID NO:2. In embodiments, the RNA sequence has 86% sequence identity to the complement of 15 consecutive nucleotides of nucleotides 1-120 of SEQ ID NO:2. In embodiments, the RNA sequence has 87% sequence identity to the complement of 15 consecutive nucleotides of nucleotides 1-120 of SEQ ID NO:2. In embodiments, the RNA sequence has 88% sequence identity to the complement of 15 consecutive nucleotides of nucleotides 1-120 of SEQ ID NO:2. In embodiments, the RNA sequence has 89% sequence identity to the complement of 15 consecutive nucleotides of nucleotides 1-120 of SEQ ID NO:2. In embodiments, the RNA sequence has 90% sequence identity to the complement of 15 consecutive nucleotides of nucleotides 1-120 of SEQ ID NO:2. In embodiments, the RNA sequence has 91% sequence identity to the complement of 15 consecutive nucleotides of nucleotides 1-120 of SEQ ID NO:2. In embodiments, the RNA sequence has 92% sequence identity to the complement of 15 consecutive nucleotides of nucleotides 1-120 of SEQ ID NO:2. In embodiments, the RNA sequence has 93% sequence identity to the complement of 15 consecutive nucleotides of nucleotides 1-120 of SEQ ID NO:2. In embodiments, the RNA sequence has 94% sequence identity to the complement of 15 consecutive nucleotides of nucleotides 1-120 of SEQ ID NO:2. In embodiments, the RNA sequence has 95% sequence identity to the complement of 15 consecutive nucleotides of nucleotides 1-120 of SEQ ID NO:2. In embodiments, the RNA sequence has 96% sequence identity to the complement of 15 consecutive nucleotides of nucleotides 1-120 of SEQ ID NO:2. In embodiments, the RNA sequence has 97% sequence identity to the complement of 15 consecutive nucleotides of nucleotides 1-120 of SEQ ID NO:2. In embodiments, the RNA sequence has 98% sequence identity to the complement of 15 consecutive nucleotides of nucleotides 1-120 of SEQ ID NO:2. In embodiments, the RNA sequence has 99% sequence identity to the complement of 15 consecutive nucleotides of nucleotides 1-120 of SEQ ID NO:2. In embodiments, the RNA sequence has 100% sequence identity to the complement of 15 consecutive nucleotides of nucleotides 1-120 of SEQ ID NO:2.

In embodiments, the RNA sequence has at least 80% sequence identity to the complement of at least 15 consecutive nucleotides of nucleotides 1-120 of SEQ ID NO:2. In embodiments, the RNA sequence has at least 80% sequence identity to the complement of at least 16 consecutive nucleotides of nucleotides 1-120 of SEQ ID NO:2. In embodiments, the RNA sequence has at least 80% sequence identity to the complement of at least 17 consecutive nucleotides of nucleotides 1-120 of SEQ ID NO:2. In embodiments, the RNA sequence has at least 80% sequence identity to the complement of at least 18 consecutive nucleotides of nucleotides 1-120 of SEQ ID NO:2. In embodiments, the RNA sequence has at least 80% sequence identity to the complement of at least 19 consecutive nucleotides of nucleotides 1-120 of SEQ ID NO:2. In embodiments, the RNA sequence has at least 80% sequence identity to the complement of at least 20 consecutive nucleotides of nucleotides 1-120 of SEQ ID NO:2. In embodiments, the RNA sequence has at least 80% sequence identity to the complement of at least 25 consecutive nucleotides of nucleotides 1-120 of SEQ ID NO:2. In embodiments, the RNA sequence has at least 80% sequence identity to the complement of at least 30 consecutive nucleotides of nucleotides 1-120 of SEQ ID NO:2. In embodiments, the RNA sequence has at least 80% sequence identity to the complement of at least 35 consecutive nucleotides of nucleotides 1-120 of SEQ ID NO:2. In embodiments, the RNA sequence has at least 80% sequence identity to the complement of at least 40 consecutive nucleotides of nucleotides 1-120 of SEQ ID NO:2. In embodiments, the RNA sequence has at least 80% sequence identity to the complement of at least 45 consecutive nucleotides of nucleotides 1-120 of SEQ ID NO:2. In embodiments, the RNA sequence has at least 80% sequence identity to the complement of at least 50 consecutive nucleotides of nucleotides 1-120 of SEQ ID NO:2.

In embodiments, the RNA sequence has 80% sequence identity to the complement of at least 15 consecutive nucleotides of nucleotides 1-120 of SEQ ID NO:2. In embodiments, the RNA sequence has 80% sequence identity to the complement of at least 16 consecutive nucleotides of nucleotides 1-120 of SEQ ID NO:2. In embodiments, the RNA sequence has 80% sequence identity to the complement of at least 17 consecutive nucleotides of nucleotides 1-120 of SEQ ID NO:2. In embodiments, the RNA sequence has 80% sequence identity to the complement of at least 18 consecutive nucleotides of nucleotides 1-120 of SEQ ID NO:2. In embodiments, the RNA sequence has 80% sequence identity to the complement of at least 19 consecutive nucleotides of nucleotides 1-120 of SEQ ID NO:2. In embodiments, the RNA sequence has 80% sequence identity to the complement of at least 20 consecutive nucleotides of nucleotides 1-120 of SEQ ID NO:2. In embodiments, the RNA sequence has 80% sequence identity to the complement of at least 25 consecutive nucleotides of nucleotides 1-120 of SEQ ID NO:2. In embodiments, the RNA sequence has 80% sequence identity to the complement of at least 30 consecutive nucleotides of nucleotides 1-120 of SEQ ID NO:2. In embodiments, the RNA sequence has 80% sequence identity to the complement of at least 35 consecutive nucleotides of nucleotides 1-120 of SEQ ID NO:2. In embodiments, the RNA sequence has 80% sequence identity to the complement of at least 40 consecutive nucleotides of nucleotides 1-120 of SEQ ID NO:2. In embodiments, the RNA sequence has 80% sequence identity to the complement of at least 45 consecutive nucleotides of nucleotides 1-120 of SEQ ID NO:2. In embodiments, the RNA sequence has 80% sequence identity to the complement of at least 50 consecutive nucleotides of nucleotides 1-120 of SEQ ID NO:2.

In embodiments, the RNA sequence has 80% sequence identity to the complement of 15 consecutive nucleotides of nucleotides 1-120 of SEQ ID NO:2. In embodiments, the RNA sequence has 80% sequence identity to the complement of 16 consecutive nucleotides of nucleotides 1-120 of SEQ ID NO:2. In embodiments, the RNA sequence has 80% sequence identity to the complement of 17 consecutive nucleotides of nucleotides 1-120 of SEQ ID NO:2. In embodiments, the RNA sequence has 80% sequence identity to the complement of 18 consecutive nucleotides of nucleotides 1-120 of SEQ ID NO:2. In embodiments, the RNA sequence has 80% sequence identity to the complement of 19 consecutive nucleotides of nucleotides 1-120 of SEQ ID NO:2. In embodiments, the RNA sequence has 80% sequence identity to the complement of 20 consecutive nucleotides of nucleotides 1-120 of SEQ ID NO:2. In embodiments, the RNA sequence has 80% sequence identity to the complement of 25 consecutive nucleotides of nucleotides 1-120 of SEQ ID NO:2. In embodiments, the RNA sequence has 80% sequence identity to the complement of 30 consecutive nucleotides of nucleotides 1-120 of SEQ ID NO:2. In embodiments, the RNA sequence has 80% sequence identity to the complement of 35 consecutive nucleotides of nucleotides 1-120 of SEQ ID NO:2.

In embodiments, the RNA sequence has 80% sequence identity to the complement of 40 consecutive nucleotides of nucleotides 1-120 of SEQ ID NO:2. In embodiments, the RNA sequence has 80% sequence identity to the complement of 45 consecutive nucleotides of nucleotides 1-120 of SEQ ID NO:2. In embodiments, the RNA sequence has 80% sequence identity to the complement of 50 consecutive nucleotides of nucleotides 1-120 of SEQ ID NO:2.

In embodiments, the RNA sequence has at least 80% sequence identity to the complement of at least 15 consecutive nucleotides of nucleotides 1-120 of SEQ ID NO:2. In embodiments, the RNA sequence has at least 80% sequence identity to the complement of at least 15 consecutive nucleotides of nucleotides 2-120 of SEQ ID NO:2. In embodiments, the RNA sequence has at least 80% sequence identity to the complement of at least 15 consecutive nucleotides of nucleotides 3-120 of SEQ ID NO:2. In embodiments, the RNA sequence has at least 80% sequence identity to the complement of at least 15 consecutive nucleotides of nucleotides 4-120 of SEQ ID NO:2. In embodiments, the RNA sequence has at least 80% sequence identity to the complement of at least 15 consecutive nucleotides of nucleotides 5-120 of SEQ ID NO:2. In embodiments, the RNA sequence has at least 80% sequence identity to the complement of at least 15 consecutive nucleotides of nucleotides 6-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-120, 2-120, 3-120, 4-120, 5-120, or 6-120 of SEQ ID NO:2.

In embodiments, the RNA sequence has at least 80% sequence identity to the complement of at least 15 consecutive nucleotides of nucleotides 7-120 of SEQ ID NO:2. In embodiments, the RNA sequence has at least 80% sequence identity to the complement of at least 15 consecutive nucleotides of nucleotides 8-120 of SEQ ID NO:2. In embodiments, the RNA sequence has at least 80% sequence identity to the complement of at least 15 consecutive nucleotides of nucleotides 9-120 of SEQ ID NO:2. In embodiments, the RNA sequence has at least 80% sequence identity to the complement of at least 15 consecutive nucleotides of nucleotides 10-120 of SEQ ID NO:2. In embodiments, the RNA sequence has at least 80% sequence identity to the complement of at least 15 consecutive nucleotides of nucleotides 11-120 of SEQ ID NO:2. In embodiments, the RNA sequence has at least 80% sequence identity to the complement of at least 15 consecutive nucleotides of nucleotides 12-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 7-120, 8-120, 9-120, 10-120, 11-120, or 12-120 of SEQ ID NO:2.

In embodiments, the RNA sequence has at least 80% sequence identity to the complement of at least 15 consecutive nucleotides of nucleotides 13-120 of SEQ ID NO:2. In embodiments, the RNA sequence has at least 80% sequence identity to the complement of at least 15 consecutive nucleotides of nucleotides 14-120 of SEQ ID NO:2. In embodiments, the RNA sequence has at least 80% sequence identity to the complement of at least 15 consecutive nucleotides of nucleotides 15-120 of SEQ ID NO:2. In embodiments, the RNA sequence has at least 80% sequence identity to the complement of at least 15 consecutive nucleotides of nucleotides 16-120 of SEQ ID NO:2. In embodiments, the RNA sequence has at least 80% sequence identity to the complement of at least 15 consecutive nucleotides of nucleotides 17-120 of SEQ ID NO:2. In embodiments, the RNA sequence has at least 80% sequence identity to the complement of at least 15 consecutive nucleotides of nucleotides 18-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 13-120, 14-120, 15-120, 16-120, 17-120, or 18-120 of SEQ ID NO:2.

In embodiments, the RNA sequence has at least 80% sequence identity to the complement of at least 15 consecutive nucleotides of nucleotides 19-120 of SEQ ID NO:2. In embodiments, the RNA sequence has at least 80% sequence identity to the complement of at least 15 consecutive nucleotides of nucleotides 20-120 of SEQ ID NO:2. In embodiments, the RNA sequence has at least 80% sequence identity to the complement of at least 15 consecutive nucleotides of nucleotides 21-120 of SEQ ID NO:2. In embodiments, the RNA sequence has at least 80% sequence identity to the complement of at least 15 consecutive nucleotides of nucleotides 22-120 of SEQ ID NO:2. In embodiments, the RNA sequence has at least 80% sequence identity to the complement of at least 15 consecutive nucleotides of nucleotides 23-120 of SEQ ID NO:2. In embodiments, the RNA sequence has at least 80% sequence identity to the complement of at least 15 consecutive nucleotides of nucleotides 24-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 19-120, 20-120, 21-120, 22-120, 23-120, or 24-120 of SEQ ID NO:2.

In embodiments, the RNA sequence has at least 80% sequence identity to the complement of at least 15 consecutive nucleotides of nucleotides 25-120 of SEQ ID NO:2. In embodiments, the RNA sequence has at least 80% sequence identity to the complement of at least 15 consecutive nucleotides of nucleotides 26-120 of SEQ ID NO:2. In embodiments, the RNA sequence has at least 80% sequence identity to the complement of at least 15 consecutive nucleotides of nucleotides 27-120 of SEQ ID NO:2. In embodiments, the RNA sequence has at least 80% sequence identity to the complement of at least 15 consecutive nucleotides of nucleotides 28-120 of SEQ ID NO:2. In embodiments, the RNA sequence has at least 80% sequence identity to the complement of at least 15 consecutive nucleotides of nucleotides 29-120 of SEQ ID NO:2. In embodiments, the RNA sequence has at least 80% sequence identity to the complement of at least 15 consecutive nucleotides of nucleotides 30-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 25-120, 26-120, 27-120, 28-120, 29-120, or 30-120 of SEQ ID NO:2.

In embodiments, the RNA sequence has at least 80% sequence identity to the complement of at least 15 consecutive nucleotides of nucleotides 31-120 of SEQ ID NO:2. In embodiments, the RNA sequence has at least 80% sequence identity to the complement of at least 15 consecutive nucleotides of nucleotides 32-120 of SEQ ID NO:2. In embodiments, the RNA sequence has at least 80% sequence identity to the complement of at least 15 consecutive nucleotides of nucleotides 33-120 of SEQ ID NO:2. In embodiments, the RNA sequence has at least 80% sequence identity to the complement of at least 15 consecutive nucleotides of nucleotides 34-120 of SEQ ID NO:2. In embodiments, the RNA sequence has at least 80% sequence identity to the complement of at least 15 consecutive nucleotides of nucleotides 35-120 of SEQ ID NO:2. In embodiments, the RNA sequence has at least 80% sequence identity to the complement of at least 15 consecutive nucleotides of nucleotides 36-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 31-120, 32-120, 33-120, 34-120, 35-120, or 36-120 of SEQ ID NO:2.

In embodiments, the RNA sequence has at least 80% sequence identity to the complement of at least 15 consecutive nucleotides of nucleotides 37-120 of SEQ ID NO:2. In embodiments, the RNA sequence has at least 80% sequence identity to the complement of at least 15 consecutive nucleotides of nucleotides 38-120 of SEQ ID NO:2. In embodiments, the RNA sequence has at least 80% sequence identity to the complement of at least 15 consecutive nucleotides of nucleotides 39-120 of SEQ ID NO:2. In embodiments, the RNA sequence has at least 80% sequence identity to the complement of at least 15 consecutive nucleotides of nucleotides 40-120 of SEQ ID NO:2. In embodiments, the RNA sequence has at least 80% sequence identity to the complement of at least 15 consecutive nucleotides of nucleotides 41-120 of SEQ ID NO:2. In embodiments, the RNA sequence has at least 80% sequence identity to the complement of at least 15 consecutive nucleotides of nucleotides 42-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 37-120, 38-120, 39-120, 40-120, 41-120, or 42-120 of SEQ ID NO:2.

In embodiments, the RNA sequence has at least 80% sequence identity to the complement of at least 15 consecutive nucleotides of nucleotides 43-120 of SEQ ID NO:2. In embodiments, the RNA sequence has at least 80% sequence identity to the complement of at least 15 consecutive nucleotides of nucleotides 44-120 of SEQ ID NO:2. In embodiments, the RNA sequence has at least 80% sequence identity to the complement of at least 15 consecutive nucleotides of nucleotides 45-120 of SEQ ID NO:2. In embodiments, the RNA sequence has at least 80% sequence identity to the complement of at least 15 consecutive nucleotides of nucleotides 46-120 of SEQ ID NO:2. In embodiments, the RNA sequence has at least 80% sequence identity to the complement of at least 15 consecutive nucleotides of nucleotides 47-120 of SEQ ID NO:2. In embodiments, the RNA sequence has at least 80% sequence identity to the complement of at least 15 consecutive nucleotides of nucleotides 48-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 43-120, 44-120, 45-120, 46-120, 47-120, or 48-120 of SEQ ID NO:2.

In embodiments, the RNA sequence has at least 80% sequence identity to the complement of at least 15 consecutive nucleotides of nucleotides 49-120 of SEQ ID NO:2. In embodiments, the RNA sequence has at least 80% sequence identity to the complement of at least 15 consecutive nucleotides of nucleotides 50-120 of SEQ ID NO:2. In embodiments, the RNA sequence has at least 80% sequence identity to the complement of at least 15 consecutive nucleotides of nucleotides 51-120 of SEQ ID NO:2. In embodiments, the RNA sequence has at least 80% sequence identity to the complement of at least 15 consecutive nucleotides of nucleotides 52-120 of SEQ ID NO:2. In embodiments, the RNA sequence has at least 80% sequence identity to the complement of at least 15 consecutive nucleotides of nucleotides 53-120 of SEQ ID NO:2. In embodiments, the RNA sequence has at least 80% sequence identity to the complement of at least 15 consecutive nucleotides of nucleotides 54-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 49-120, 50-120, 51-120, 52-120, 53-120, or 54-120 of SEQ ID NO:2.

In embodiments, the RNA sequence has at least 80% sequence identity to the complement of at least 15 consecutive nucleotides of nucleotides 55-120 of SEQ ID NO:2. In embodiments, the RNA sequence has at least 80% sequence identity to the complement of at least 15 consecutive nucleotides of nucleotides 56-120 of SEQ ID NO:2. In embodiments, the RNA sequence has at least 80% sequence identity to the complement of at least 15 consecutive nucleotides of nucleotides 57-120 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 55-120, 56-120, or 57-120 of SEQ ID NO:2.

In embodiments, the RNA sequence has at least 80% sequence identity to the complement of at least 15 consecutive nucleotides of nucleotides 1-120 of SEQ ID NO:2. In embodiments, the RNA sequence has at least 80% sequence identity to the complement of at least 15 consecutive nucleotides of nucleotides 1-119 of SEQ ID NO:2. In embodiments, the RNA sequence has at least 80% sequence identity to the complement of at least 15 consecutive nucleotides of nucleotides 1-118 of SEQ ID NO:2. In embodiments, the RNA sequence has at least 80% sequence identity to the complement of at least 15 consecutive nucleotides of nucleotides 1-117 of SEQ ID NO:2. In embodiments, the RNA sequence has at least 80% sequence identity to the complement of at least 15 consecutive nucleotides of nucleotides 1-116 of SEQ ID NO:2. In embodiments, the RNA sequence has at least 80% sequence identity to the complement of at least 15 consecutive nucleotides of nucleotides 1-115 of SEQ ID NO:2. In embodiments, the RNA sequence has at least 80% sequence identity to the complement of at least 15 consecutive nucleotides of nucleotides 1-114 of SEQ ID NO:2. In embodiments, the RNA sequence has at least 80% sequence identity to the complement of at least 15 consecutive nucleotides of nucleotides 1-113 of SEQ ID NO:2. In embodiments, the RNA sequence has at least 80% sequence identity to the complement of at least 15 consecutive nucleotides of nucleotides 1-112 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-120, 1-119, 1-118, 1-117, 1-116, 1-115, 1-114, 1-113, or 1-112 of SEQ ID NO:2.

In embodiments, the RNA sequence has at least 80% sequence identity to the complement of at least 15 consecutive nucleotides of nucleotides 1-111 of SEQ ID NO:2. In embodiments, the RNA sequence has at least 80% sequence identity to the complement of at least 15 consecutive nucleotides of nucleotides 1-110 of SEQ ID NO:2. In embodiments, the RNA sequence has at least 80% sequence identity to the complement of at least 15 consecutive nucleotides of nucleotides 1-109 of SEQ ID NO:2. In embodiments, the RNA sequence has at least 80% sequence identity to the complement of at least 15 consecutive nucleotides of nucleotides 1-108 of SEQ ID NO:2. In embodiments, the RNA sequence has at least 80% sequence identity to the complement of at least 15 consecutive nucleotides of nucleotides 1-107 of SEQ ID NO:2. In embodiments, the RNA sequence has at least 80% sequence identity to the complement of at least 15 consecutive nucleotides of nucleotides 1-106 of SEQ ID NO:2. In embodiments, the RNA sequence has at least 80% sequence identity to the complement of at least 15 consecutive nucleotides of nucleotides 1-105 of SEQ ID NO:2. In embodiments, the RNA sequence has at least 80% sequence identity to the complement of at least 15 consecutive nucleotides of nucleotides 1-104 of SEQ ID NO:2. In embodiments, the RNA sequence has at least 80% sequence identity to the complement of at least 15 consecutive nucleotides of nucleotides 1-103 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-111, 1-110, 1-109, 1-108, 1-107, 1-106, 1-105, 1-104, or 1-103 of SEQ ID NO:2.

In embodiments, the RNA sequence has at least 80% sequence identity to the complement of at least 15 consecutive nucleotides of nucleotides 1-102 of SEQ ID NO:2. In embodiments, the RNA sequence has at least 80% sequence identity to the complement of at least 15 consecutive nucleotides of nucleotides 1-101 of SEQ ID NO:2. In embodiments, the RNA sequence has at least 80% sequence identity to the complement of at least 15 consecutive nucleotides of nucleotides 1-100 of SEQ ID NO:2. In embodiments, the RNA sequence has at least 80% sequence identity to the complement of at least 15 consecutive nucleotides of nucleotides 1-99 of SEQ ID NO:2. In embodiments, the RNA sequence has at least 80% sequence identity to the complement of at least 15 consecutive nucleotides of nucleotides 1-98 of SEQ ID NO:2. In embodiments, the RNA sequence has at least 80% sequence identity to the complement of at least 15 consecutive nucleotides of nucleotides 1-97 of SEQ ID NO:2. In embodiments, the RNA sequence has at least 80% sequence identity to the complement of at least 15 consecutive nucleotides of nucleotides 1-96 of SEQ ID NO:2. In embodiments, the RNA sequence has at least 80% sequence identity to the complement of at least 15 consecutive nucleotides of nucleotides 1-95 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-102, 1-101, 1-100, 1-99, 1-98, 1-97, 1-96, or 1-95 of SEQ ID NO:2.

In embodiments, the RNA sequence has at least 80% sequence identity to the complement of at least 15 consecutive nucleotides of nucleotides 1-94 of SEQ ID NO:2. In embodiments, the RNA sequence has at least 80% sequence identity to the complement of at least 15 consecutive nucleotides of nucleotides 1-93 of SEQ ID NO:2. In embodiments, the RNA sequence has at least 80% sequence identity to the complement of at least 15 consecutive nucleotides of nucleotides 1-92 of SEQ ID NO:2. In embodiments, the RNA sequence has at least 80% sequence identity to the complement of at least 15 consecutive nucleotides of nucleotides 1-91 of SEQ ID NO:2. In embodiments, the RNA sequence has at least 80% sequence identity to the complement of at least 15 consecutive nucleotides of nucleotides 1-90 of SEQ ID NO:2. In embodiments, the RNA sequence has at least 80% sequence identity to the complement of at least 15 consecutive nucleotides of nucleotides 1-89 of SEQ ID NO:2. In embodiments, the RNA sequence has at least 80% sequence identity to the complement of at least 15 consecutive nucleotides of nucleotides 1-88 of SEQ ID NO:2. In embodiments, the RNA sequence has at least 80% sequence identity to the complement of at least 15 consecutive nucleotides of nucleotides 1-87 of SEQ ID NO:2. In embodiments, the RNA sequence has at least 80% sequence identity to the complement of at least 15 consecutive nucleotides of nucleotides 1-86 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-94, 1-93, 1-92, 1-91, 1-90, 1-89, 1-88, 1-87, or 1-86 of SEQ ID NO:2.

In embodiments, the RNA sequence has at least 80% sequence identity to the complement of at least 15 consecutive nucleotides of nucleotides 1-85 of SEQ ID NO:2. In embodiments, the RNA sequence has at least 80% sequence identity to the complement of at least 15 consecutive nucleotides of nucleotides 1-84 of SEQ ID NO:2. In embodiments, the RNA sequence has at least 80% sequence identity to the complement of at least 15 consecutive nucleotides of nucleotides 1-83 of SEQ ID NO:2. In embodiments, the RNA sequence has at least 80% sequence identity to the complement of at least 15 consecutive nucleotides of nucleotides 1-82 of SEQ ID NO:2. In embodiments, the RNA sequence has at least 80% sequence identity to the complement of at least 15 consecutive nucleotides of nucleotides 1-81 of SEQ ID NO:2. In embodiments, the RNA sequence has at least 80% sequence identity to the complement of at least 15 consecutive nucleotides of nucleotides 1-80 of SEQ ID NO:2. In embodiments, the RNA sequence has at least 80% sequence identity to the complement of at least 15 consecutive nucleotides of nucleotides 1-79 of SEQ ID NO:2. In embodiments, the RNA sequence has at least 80% sequence identity to the complement of at least 15 consecutive nucleotides of nucleotides 1-78 of SEQ ID NO:2. In embodiments, the RNA sequence has at least 80% sequence identity to the complement of at least 15 consecutive nucleotides of nucleotides 1-77 of SEQ ID NO:2. For the above embodiments, the RNA sequence may have about 85%, 90%, 91%, 92%, 93%, 94%, 95%, 96%, 97%, 98% or 99% sequence identity to the complement of at least 15 (e.g., 15, 16, 17, 18, 19, 20, 21, 22, 23, 24 or 25) consecutive nucleotides of nucleotides 1-85, 1-84, 1-83, 1-82, 1-81, 1-80, 1-79, 1-78, or 1-77 of SEQ ID NO:2.

The ribonucleic acid compounds provided herein including embodiments thereof may include one or more compound moieties. The RNA sequence of the ribonucleic acid compounds provided herein including embodiments thereof may be bound to one or more compound moieties. The compound moiety may be a targeting moiety. A "targeting moiety" as provided herein is a chemical moiety capable of binding a molecule expressed by a cell thereby facilitating targeting and delivery of the ribonucleic acid compound to a specific cell type. In embodiments, the ribonucleic acid compound includes a compound moiety (e.g., targeting moiety) covalently bound to the RNA sequence. In embodiments, the ribonucleic acid compound includes a compound moiety (e.g., targeting moiety) non-covalently bound to the RNA sequence. Targeting moieties contemplated herein include without limitation peptides, lipids, carbohydrates, organic nanoparticles, dendrimers, and mixes of nanoparticle (e.g., an organic nanoparticle) and dendrimer capable of facilitating cell penetration of ribonucleic acid compounds as provided herein.

In embodiments, the targeting moiety is a peptide moiety. Non-limiting examples of peptide moieties include cell-penetrating peptide (CPP) moieties; nuclear localization signal (NLS) moieties, and Tat peptide moieties. Cell-penetrating peptide moieties are short (e.g., 10-30 amino acid), water-soluble amino acid sequences. CPP moieties may include basic amino acids such as arginine and lysine and may be cationic or amphipathic. CPP moieties are useful for facilitating intracellular delivery of non-cell penetrating compounds provided herein. Thus, in embodiments, the compound moiety is a CPP moiety. In embodiments, the CPP moiety is NF51. In embodiments, the CPP moiety has the sequence of SEQ ID NO:28. In embodiments, the CPP moiety is the sequence of SEQ ID NO:28. In embodiments, the CPP moiety includes the sequence of SEQ ID NO:28. In embodiments, the CPP moiety is NF57. In embodiments, the CPP moiety has the sequence of SEQ ID NO:29. In embodiments, the CPP moiety includes the sequence of SEQ ID NO:29. In embodiments, the CPP moiety is the sequence of SEQ ID NO:29. In embodiments, the CPP moiety is PF3. In embodiments, the CPP moiety has the sequence of SEQ ID NO:30. In embodiments, the CPP moiety is the sequence of SEQ ID NO:30. In embodiments, the CPP moiety includes the sequence of SEQ ID NO:30. In embodiments, the CPP moiety is TP10. In embodiments, the CPP moiety has the sequence of SEQ ID NO:31. In embodiments, the CPP moiety is the sequence of SEQ ID NO:31. In embodiments, the CPP moiety includes the sequence of SEQ ID NO:31. In embodiments, the CPP moiety is PF6. In embodiments, the CPP moiety has the sequence of SEQ ID NO:32. In embodiments, the CPP moiety is the sequence of SEQ ID NO:32. In embodiments, the CPP moiety includes the sequence of SEQ ID NO:32. In embodiments, K7 of SEQ ID NO:32 is modified by covalent attachment of the K (lysine) tree

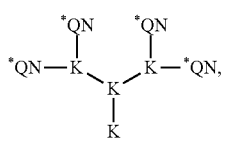

wherein *QN is

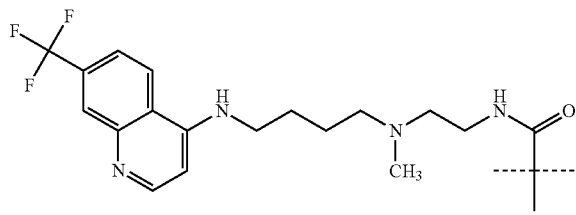

(N-(2-(methyl(4-((7-(trifluoromethyl)quinolin-4-yl)amino)butyl)amino)ethyl)acetamide). In embodiments, the CPP moiety is PF14. In embodiments, the CPP moiety has the sequence of SEQ ID NO:33. In embodiments, the CPP moiety is the sequence of SEQ ID NO:33. In embodiments, the CPP moiety includes the sequence of SEQ ID NO:33. In embodiments, the CPP moiety is LMWP. In embodiments, the CPP moiety has the sequence of SEQ ID NO:34. In embodiments, the CPP moiety is the sequence of SEQ ID NO:34. In embodiments, the CPP moiety includes the sequence of SEQ ID NO:34. In embodiments, the CPP moiety is GAG KW-22. In embodiments, the CPP moiety has the sequence of SEQ ID NO:35. In embodiments, the CPP moiety is the sequence of SEQ ID NO:35. In embodiments, the CPP moiety includes the sequence of SEQ ID NO:35. A general description of CPPs and their usage, and, specifically NF51, NF57, PF3, TP10, PF6, PF14, LMWP, and GAG KW-22, can be found in Mol Ther Nucleic Acids. 2017 Jun. 16; 7: 1-10, Theranostics. 2017; 7(9): 2495-2508, and Protein Pept Lett 2014; 21(2): 124-131, which are incorporated herein by reference in their entirety and for all purposes.

In embodiments, the compound moiety is a nuclear localization signal (NLS) moiety. A NLS is an amino acid sequence typically consisting of one or more short sequences of positively charged lysines or arginines. NLSs may also include glycine-rich sequences. In embodiments, the NLS moiety includes the sequence of SEQ ID NO:36. In embodiments, the NLS moiety is the sequence of SEQ ID NO:36. A description of NLS and its use can be found in Chem Sci. 2017 Apr. 1; 8(4):2816-2822, which is incorporated herein by reference in its entirety and for all purposes.

In embodiments, the compound moiety is a Tat peptide moiety. A Tat peptide moiety includes at least a portion of the Tat protein, also known as trans-activator of transcription, encoded by the tat at gene in HIV-1. In embodiments, the Tat peptide moiety includes the sequence of SEQ ID NO:37. In embodiments, the Tat peptide moiety is the sequence of SEQ ID NO:37. A description of Tat peptide can be found in Mol Ther. 2016 Mar. 24(3): 548-555, which is incorporated herein by reference in its entirety and for all purposes.

In embodiments, the RNA sequence (e.g., small RNA, siRNA) is attached (e.g., covalently or non-covalently) to a CPP moiety as described herein, including embodiments thereof. In embodiments, the RNA sequence (e.g., small RNA, siRNA) is attached (e.g., covalently or non-covalently) to a NLS moiety as described herein, including embodiments thereof. In embodiments, the RNA sequence (e.g., small RNA, siRNA) is attached (e.g., covalently or non-covalently) to a Tat peptide moiety as described herein, including embodiments thereof.

A non-limiting example of a lipid based compound moiety is palmitic acid. Thus, in embodiments, the compound moiety is palmitic acid moiety. In embodiments, the RNA sequence (e.g., small RNA, siRNA) is attached (e.g., covalently or non-covalently) to a palmitic acid moiety.

A non-limiting example of a carbohydrate contemplated as a compound moiety is trivalent (triantennary) N-acetylgalactosamine (GalNAc). In embodiments, GalNAc refers to CAS Reg. No. 1811-31-0. In embodiments, the compound moiety is GalNAc. A description of GalNAc and its use can be found in Mol. Ther. 2018 Jan. 3; 26(1):105-114 and Mol Ther Nucleic Acids. 2017 Mar. 17; 6: 116-132, which are incorporated herein by reference in their entirety and for all purposes.

In embodiments, the targeting moiety is a liver targeting moiety. A "liver targeting moiety" as provided herein is a compound moiety (e.g., cholesterol or trivalent (triantennary) N-acetylgalactosamine (GalNac)) that binds and internalizes into liver cells. When attached to a compound (e.g., the nucleic acid compound provided herein) the targeting moiety conveys these targeting and internalization properties to said compound (e.g., the nucleic acid compound provided herein) thereby facilitating the uptake or internalization of said compound (e.g., the nucleic acid compound provided herein) by said cell. In embodiments, the compound moiety is a liver targeting moiety. In embodiments, the liver targeting moiety is a trivalent (triantennary) N-acetylgalactosamine (GalNAc) moiety. In embodiments, the liver targeting moiety is a cholesterol moiety. In embodiments, the RNA sequence (e.g., small RNA) is attached (e.g., covalently or non-covalently) to a trivalent (triantennary) N-acetylgalactosamine (GalNAc) moiety. In embodiments, the RNA sequence (e.g., small RNA) is attached (e.g., covalently or non-covalently) to a cholesterol moiety.

As described supra, compound moieties may interact covalently or non-covalently with ribonucleic acid compounds to facilitate intracellular delivery. Lipids, carbohydrates, organic nanoparticles, dendrimers, and nanoparticle (e.g., organic nanoparticle)/dendrimer mixtures are contemplated herein as suitable compound moieties for indirect interactions with ribonucleic acid compounds as described herein, including embodiments thereof, to facilitate intracellular delivery.

Non-limiting examples of lipid-based compound moieties considered useful for the ribonucleic acid compounds as provided herein include liposomes and Lipofectamine®. A description of liposome intracellular delivery systems may be found in J Control Release. 2017 Dec. 23; 271:98-106, which is incorporated by reference herein in its entirety and for all purposes. Therefore, in embodiments, the compound moiety is a liposome. In embodiments, the RNA sequence is non-covalently bound to a liposome. In embodiments, the liposome further includes liposome cell targeting moieties (e.g., antibodies, ligands, peptides). A liposome cell targeting moiety allows the liposome to target specific cells (e.g., liver cells). In embodiments, the liposome includes a liposome liver targeting moiety. In embodiments, the liposome is Lipofectamine®. A description of Lipofectamine® and its use may be found in Clin Transl Oncol. 2018 Jan. 5, 12094-017-1821-0, which is incorporated herein by reference in its entirety and for all purposes.

Non-limiting examples of carbohydrate-based compound moieties considered useful for the ribonucleic acid compounds as provided herein include chitosan and hyaluronic acid (HA). A description of chitosan and its use in facilitating intracellular delivery may be found in Methods Mol Biol. 2016; 1364:143-50, which is incorporated herein by reference in its entirety and for all purposes. A description of HA and its use in facilitating intracellular delivery may be found in Top Curr Chem (Cham). 2017 April; 375(2):31, which is incorporated herein by reference in its entirety and for all purposes.

In embodiments, the compound moiety is chitosan. In embodiments, the RNA sequence is non-covalently bound to chitosan. In embodiments, the compound moiety is HA. In embodiments, the RNA sequence i is non-covalently bound to HA.

Dendrimers and dendrimer conjugates are also considered as suitable compound moieties for the ribonucleic acid compounds as provided herein. Dendrimers and dendrimer conjugates may form complexes with the ribonucleic acid compounds provided herein, thereby stabilizing the ribonucleic acid compound and facilitating its intracellular delivery. Non-limiting examples of dendrimers include PAMAM and totally branched PEI. PAMAM refers to poly(amidoamine) which is a dendrimer including an alkyldiamine core and tertiary amine groups. In embodiments, PAMAM includes an ethylenediamine core. In embodiments, PAMAM refers to CAS Reg. No. 163442-68-0. In embodiments, PAMAM refers to CAS Reg. No. 163442-67-9. Branched PEI refers to polyethylenimine, which is a polymer composed of an amino groups and two carbon aliphatic $CH_2CH_2$ spacers that form branch to form a dendrimer. In embodiments, PEI refers to CAS Reg No. 9002-98-6. Descriptions of dendrimers, and specifically PAMAM, PAMAM conjugates, and branched PEI and their use can be found in Int J Pharm. 2017 Jul. 15; 527(1-2):171-183, Acta Biomater. 2016 Oct. 1; 43:14-29, Oncotarget. 2016 Mar. 22; 7(12):13782-96, and Nanoscale. 2017 Oct. 19; 9(40):15461-15469, which are incorporated herein by reference in their entirety and for all purposes. Thus, in embodiments, the compound moiety is a dendimer. In embodiments, the dendrimer is PAMAM. In embodiments, the compound moiety is a dendrimer conjugate. In embodiments, the dendrimer is a PAMAM-PEG conjugate. In embodiments, the dendrimer is a PAMAM-H-R3 conjugate. In embodiments, the dendrimer is a PAMAM-TPP conjugate. TPP refers to triphenyl phosphonium. In embodiments, TPP refers to CAS Reg. No. 4009-98-7. In embodiments, the dendrimer is a branched PEI. In embodiments, the RNA sequence is non-covalently bound to a dendrimer or dendrimer conjugate. In embodiments, the RNA sequence is non-covalently bound to a PAMAM dendrimer. In embodiments, the RNA sequence is non-covalently bound to a PAMAM-PEG dendrimer conjugate. In embodiments, the RNA sequence is non-covalently bound to a PAMAM-H-R3 dendrimer conjugate. In embodiments, the RNA sequence is non-covalently bound to a branched PEI dendrimer.

It should be appreciated that the compound moieties described herein, including embodiments thereof may be used separately or in combination with one another (e.g., PEI and HA).

Pharmaceutical Formulations

The ribonucleic acid compounds provided herein, including embodiments thereof, are contemplated as being useful for the treatment of disease (e.g., hypercholesterolemia). Thus, in an aspect is provided a pharmaceutical formulation including the ribonucleic acid compound provided herein, including embodiments thereof, and a pharmaceutically acceptable excipient.

Methods of Treatment

It is further contemplated that the ribonucleic acid compounds provided herein, including embodiments thereof, may be used to treat diseases such as hypercholesterolemia. Thus, in an aspect there is provided a method of treating hypercholesterolemia. The method includes administering to a subject in need thereof an effective amount of the ribonucleic acid compound provided herein including embodiments thereof. In embodiments, the ribonucleic acid compound includes the sequences of SEQ ID NOs:11 and 12. In embodiments, the ribonucleic acid compound is the sequences of SEQ ID NOs:11 and 12. In embodiments, the ribonucleic acid compound includes the sequence of SEQ ID NO:12. In embodiments, the ribonucleic acid compound is the sequence of SEQ ID NO:12. In embodiments, the ribonucleic acid compound includes the sequences of SEQ ID NOs:21 and 22. In embodiments, the ribonucleic acid compound is the sequences of SEQ ID NOs:21 and 22. In embodiments, the ribonucleic acid compound includes the sequence of SEQ ID NO:22. In embodiments, the ribonucleic acid compound is the sequence of SEQ ID NO:22. In embodiments, the ribonucleic acid compounds include a compound moiety. In embodiments, the compound moiety is covalently attached to RNA sequence. In embodiments, the compound moiety is noon-covalently attached to the RNA sequence. In embodiments, the compound moiety is GalNAc. In embodiments, the GalNAc is covalently attached to the RNA sequence.

In embodiments, the method includes administering an additional ribonucleic acid compound. Thus, in embodiments, the method includes administering a first ribonucleic acid compound and a second ribonucleic acid compound, wherein the first ribonucleic acid compound and the second ribonucleic acid compound are different. In embodiments, the first ribonucleic acid compound includes the sequences of SEQ ID NOs:11 and 12. In embodiments, the first ribonucleic acid compound is the sequences of SEQ ID NOs:11 and 12. In embodiments, the first ribonucleic acid compound includes the sequence of SEQ ID NO:12. In embodiments, the first ribonucleic acid compound is the sequence of SEQ ID NO:12. In embodiments, the second ribonucleic acid compound includes the sequences of SEQ ID NOs:21 and 22. In embodiments, the second ribonucleic acid compound is the sequences of SEQ ID NOs:21 and 22. In embodiments, the second ribonucleic acid compound includes the sequence of SEQ ID NO:22. In embodiments, the second ribonucleic acid compound is the sequence of SEQ ID NO:22. In embodiments, the ribonucleic acid compounds described in this paragraph include a compound moiety. In embodiments, the compound moiety is GalNAc. In embodiments, the GalNAc is covalently attached to the RNA sequence described in this paragraph.

In embodiments, an effective amount of a ribonucleic acid compound is less than about 2000 nM, about 1500 nM, about 1000 nM, about 900 nM, about 800 nM, about 700 nM, about 600 nM, about 500 nM, about 100 nM, about 75 nM, about 65 nM, about 60 nM, about 55 nM, about 50 nM, about 45 nM, about 40 nM, about 35 nM, about 30 nM, about 25 nM, about 20 nM, about 15 nM, about 10 nM, about 5 nM, about 3 nM, or about 1 nM. In embodiments, an effective amount of a ribonucleic acid compound is less than 2000 nM, 1500 nM, 1000 nM, 900 nM, 800 nM, 700 nM, 600 nM, 500 nM, 100 nM, 75 nM, 65 nM, 60 nM, 55 nM, 50 nM, 45 nM, 40 nM, 35 nM, 30 nM, 25 nM, 20 nM, 15 nM, 10 nM, 5 nM, 3 nM, or 1 nM.

In embodiments, the ribonucleic acid compound is administered at an amount of less than about 2000 nM. In embodiments, the ribonucleic acid compound is administered at an amount of less than about 1500 nM. In embodiments, the ribonucleic acid compound is administered at an amount of less than about 1000 nM. In embodiments, the ribonucleic acid compound is administered at an amount of less than about 900 nM. In embodiments, the ribonucleic acid compound is administered at an amount of less than about 800 nM. In embodiments, the ribonucleic acid compound is administered at an amount of less than about 700 nM. In embodiments, the ribonucleic acid compound is administered at an amount of less than about 600 nM. In embodiments, the ribonucleic acid compound is administered at an amount of less than about 500 nM. In embodiments, the ribonucleic acid compound is administered at an amount of less than about 100 nM. In embodiments, the ribonucleic acid compound is administered at an amount of less than about 75 nM. In embodiments, the ribonucleic acid compound is administered at an amount of less than about 65 nM. In embodiments, the ribonucleic acid compound is administered at an amount of less than about 60 nM. In embodiments, the ribonucleic acid compound is administered at an amount of less than about 55 nM. In embodiments, the ribonucleic acid compound is administered at an amount of less than about 50 nM. In embodiments, the ribonucleic acid compound is administered at an amount of less than about 45 nM. In embodiments, the ribonucleic acid compound is administered at an amount of less than about 40 nM. In embodiments, the ribonucleic acid compound is administered at an amount of less than about 35 nM. In embodiments, the ribonucleic acid compound is administered at an amount of less than about 30 nM. In embodiments, the ribonucleic acid compound is administered at an amount of less than about 25 nM. In embodiments, the ribonucleic acid compound is administered at an amount of less than about 20 nM. In embodiments, the ribonucleic acid compound is administered at an amount of less than about 15 nM. In embodiments, the ribonucleic acid compound is administered at an amount of less than about 10 nM. In embodiments, the ribonucleic acid compound is administered at an amount of less than about 5 nM. In embodiments, the ribonucleic acid compound is administered at an amount of less than about 3 nM. In embodiments, the ribonucleic acid compound is administered at an amount of less than about 1 nM.

In embodiments, the ribonucleic acid compound is administered at an amount of less than 2000 nM. In embodiments, the ribonucleic acid compound is administered at an amount of less than 1500 nM. In embodiments, the ribonucleic acid compound is administered at an amount of less than 1000 nM. In embodiments, the ribonucleic acid compound is administered at an amount of less than 900 nM. In embodiments, the ribonucleic acid compound is administered at an amount of less than 800 nM. In embodiments, the ribonucleic acid compound is administered at an amount of less than 700 nM. In embodiments, the ribonucleic acid compound is administered at an amount of less than 600 nM. In embodiments, the ribonucleic acid compound is administered at an amount of less than 500 nM. In embodiments, the ribonucleic acid compound is administered at an amount of less than 100 nM. In embodiments, the ribonucleic acid compound is administered at an amount of less than 75 nM. In embodiments, the ribonucleic acid compound is administered at an amount of less than 65 nM. In embodiments, the ribonucleic acid compound is administered at an amount of less than 60 nM. In embodiments, the ribonucleic acid compound is administered at an amount of less than 55 nM. In embodiments, the ribonucleic acid compound is administered at an amount of less than 50 nM. In embodiments, the ribonucleic acid compound is administered at an amount of less than 45 nM. In embodiments, the ribonucleic acid compound is administered at an amount of less than 40 nM. In embodiments, the ribonucleic acid compound is administered at an amount of less than 35 nM. In embodiments, the ribonucleic acid compound is administered at an amount of less than 30 nM. In embodiments, the ribonucleic acid compound is administered at an amount of less than 25 nM. In embodiments, the ribonucleic acid compound is administered at an amount of less than 20 nM. In embodiments, the ribonucleic acid compound is administered at an amount of less than 15 nM. In embodiments, the ribonucleic acid compound is administered at an amount of less than 10 nM. In embodiments, the ribonucleic acid compound is administered at an amount of less than 5 nM. In embodiments, the ribonucleic acid compound is administered at an amount of less than 3 nM. In embodiments, the ribonucleic acid compound is administered at an amount of less than 1 nM.

In embodiments, the first and second ribonucleic acid compounds are administered simultaneously. In embodiments, the first and second ribonucleic acid compounds are administered sequentially. Sequential administration may occur with a time delay on the order of, for example, minutes, hours, days, or months.

In embodiments, there is provided a method of activating LDLR in a cell. The method includes contacting a cell with an effective amount of the ribonucleic acid compound, thereby activating LDLR in a cell. In embodiments, the method further includes allowing binding of the ribonucleic acid compound to an LDLR-lncRNA. In embodiments, the ribonucleic acid compound is capable of hybridizing to the promoter of the LDLR-lncRNA.

In embodiments, there is provided a method of inhibiting expression of an LDLR-lncRNA in a cell. The method includes contacting a cell with an effective amount of the ribonucleic acid compound, thereby inhibiting expression of an LDLR-lncRNA in a cell.

EXAMPLES

Example 1

Figure 1B:
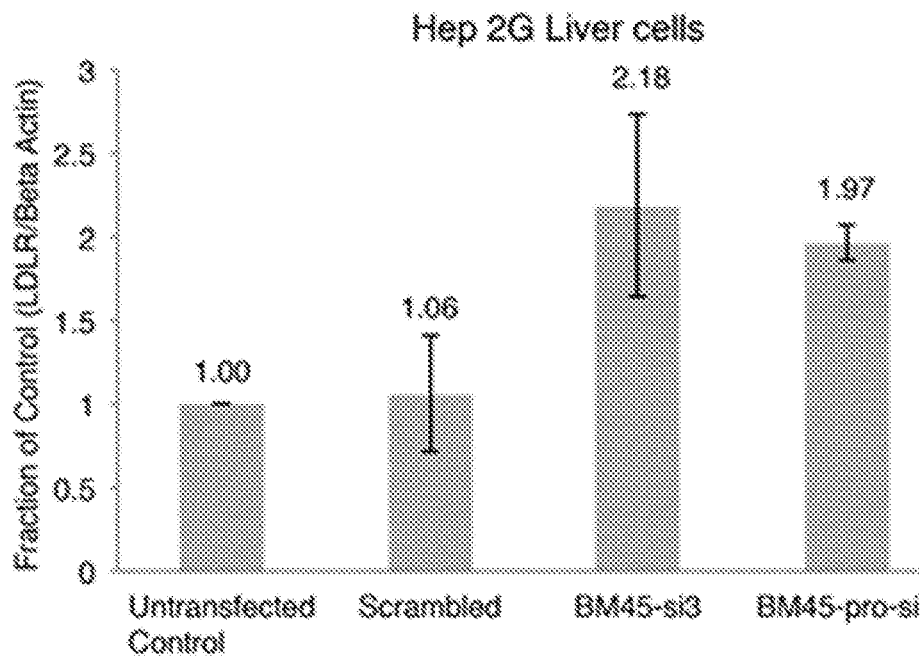
Figure 1C:
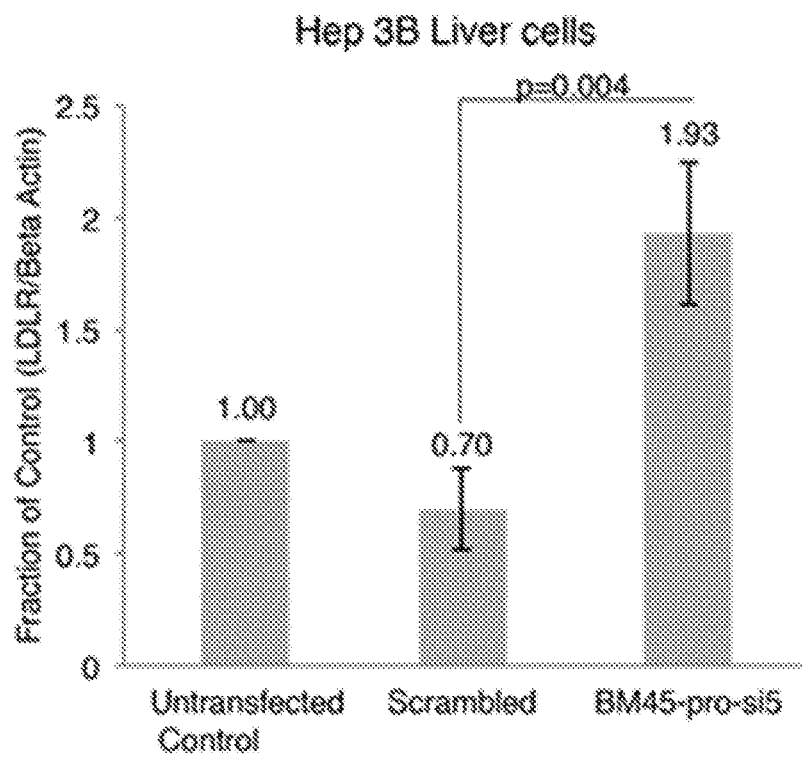
Figure 2:
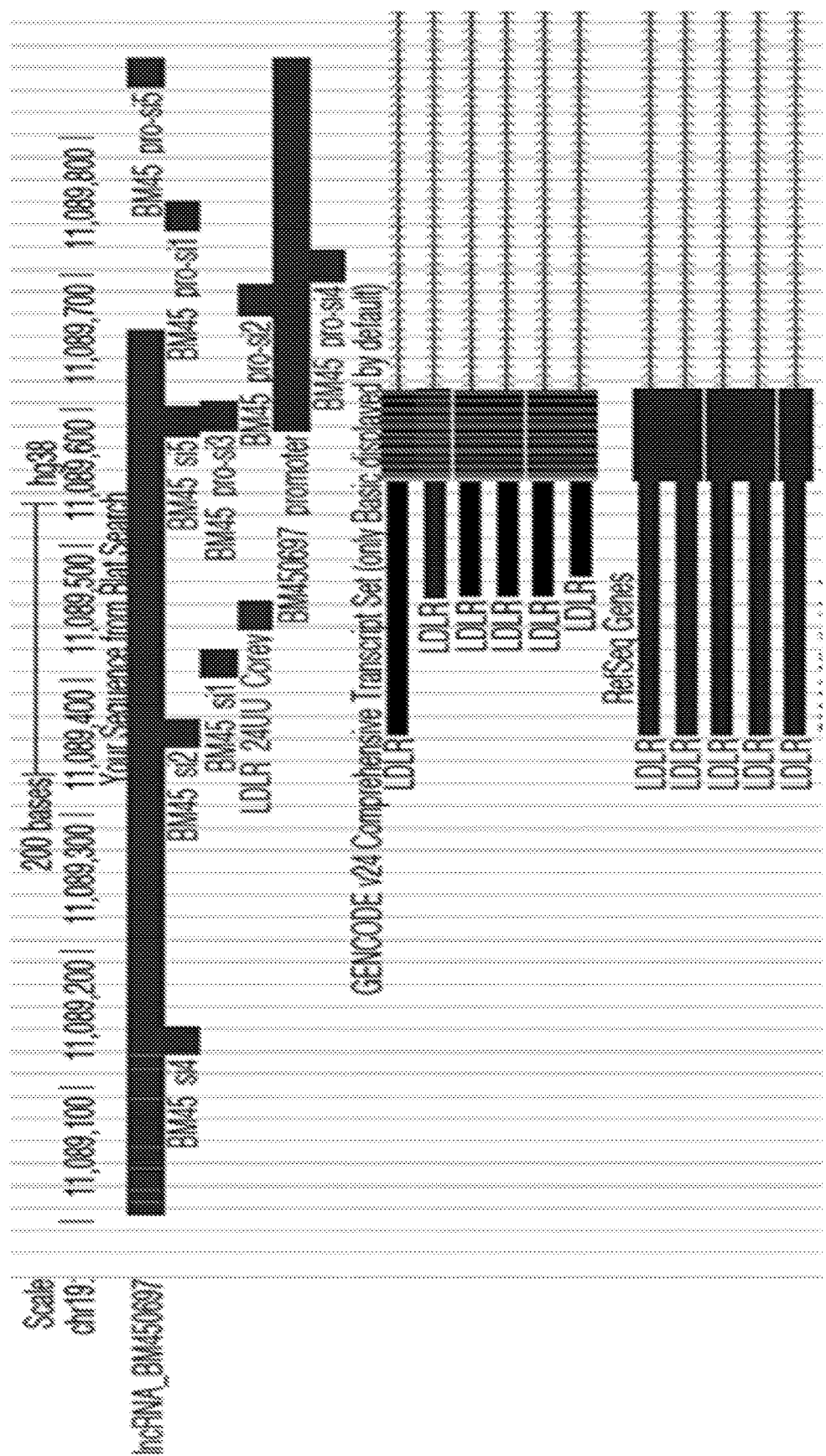
FIG. 2. A UCSC genome browser snapshot of the LDLR locus (5' to 3'), the BM450697 lncRNA (3' to 5'), and the BM450697 lncRNA promoter (3' to 5'; as defined by Kevin Morris) for determining small RNAs that can target the lncRNA transcript and promoter to induce activation of LDLR. The 24UU siRNA candidate from Dr. David Corey's lab (See Matsui et al., 2010) is shown in addition to n=4 siRNAs targeting the BM450697 lncRNA transcript and n=5 targeting the BM450697 lncRNA promoter. BM45 pro-si1, also referred to herein as BM45_pro-si1, prosi_1, pro_1, pro_1, sipro1, or p1, corresponds to SEQ ID NOs:3 and 4, which are sense and antisense strands, respectively, of the BM45 pro-si1 siRNA. BM45 pro-si2, also referred to herein as BM45_pro-si2, prosi_2, pro_2, pro_2, sipro2, or p2, corresponds to SEQ ID NOs:5 and 6, which are sense and antisense strands, respectively, of the BM45 pro-si2 siRNA. BM45 pro-si3, also referred to herein as BM45_pro-si3, prosi_3, pro_3, pro_3, sipro3, or p3, corresponds to SEQ ID NOs:7 and 8, which are sense and antisense strands, respectively, of the BM45 pro-si3 siRNA. BM45 pro-si4, also referred to herein as BM45_pro-si4, prosi_4, pro 4, pro_4, sipro4, or p4, corresponds to SEQ ID NOs:9 and 10, which are sense and antisense strands, respectively, of the BM45 pro-si4 siRNA. BM45 pro-si5, also referred to herein as BM45_pro-si5, prosi_5, pro_5, pro_5, sipro5, or p5, corresponds to SEQ ID NOs:11 and 12, which are sense and antisense strands, respectively, of the BM45 pro-si5 siRNA. BM45_si1, also referred to herein as BM45-si1, BM45_si1, si1, si_1, or 1, corresponds to SEQ ID NOs:13 and 14, which are sense and antisense strands, respectively, of the BM45_si1 siRNA. BM45_si2, also referred to herein as BM45-si2, BM45_si2, si2, si_2, or 2, corresponds to SEQ ID NOs:15 and 16, which are sense and antisense strands, respectively, of the BM45_si2 siRNA. BM45_si3, also referred to herein as BM45-si3, BM45_si3, si3, si_3, or 3, corresponds to SEQ ID NOs:17 and 18, which are sense and antisense strands, respectively, of the BM45_si3 siRNA. BM45_si4, also referred to herein as BM45-si4, BM45_si4, si4, si_4, or 4, corresponds to SEQ ID NOs:19 and 20, which are sense and antisense strands, respectively, of the BM45_si4 siRNA. BM45_si5, also referred to herein as BM45-si5, si5, si_5, or 5, corresponds to SEQ ID NOs:21 and 22, which are sense and antisense strands, respectively, of the BM45_si5 siRNA.
Figure 3A:
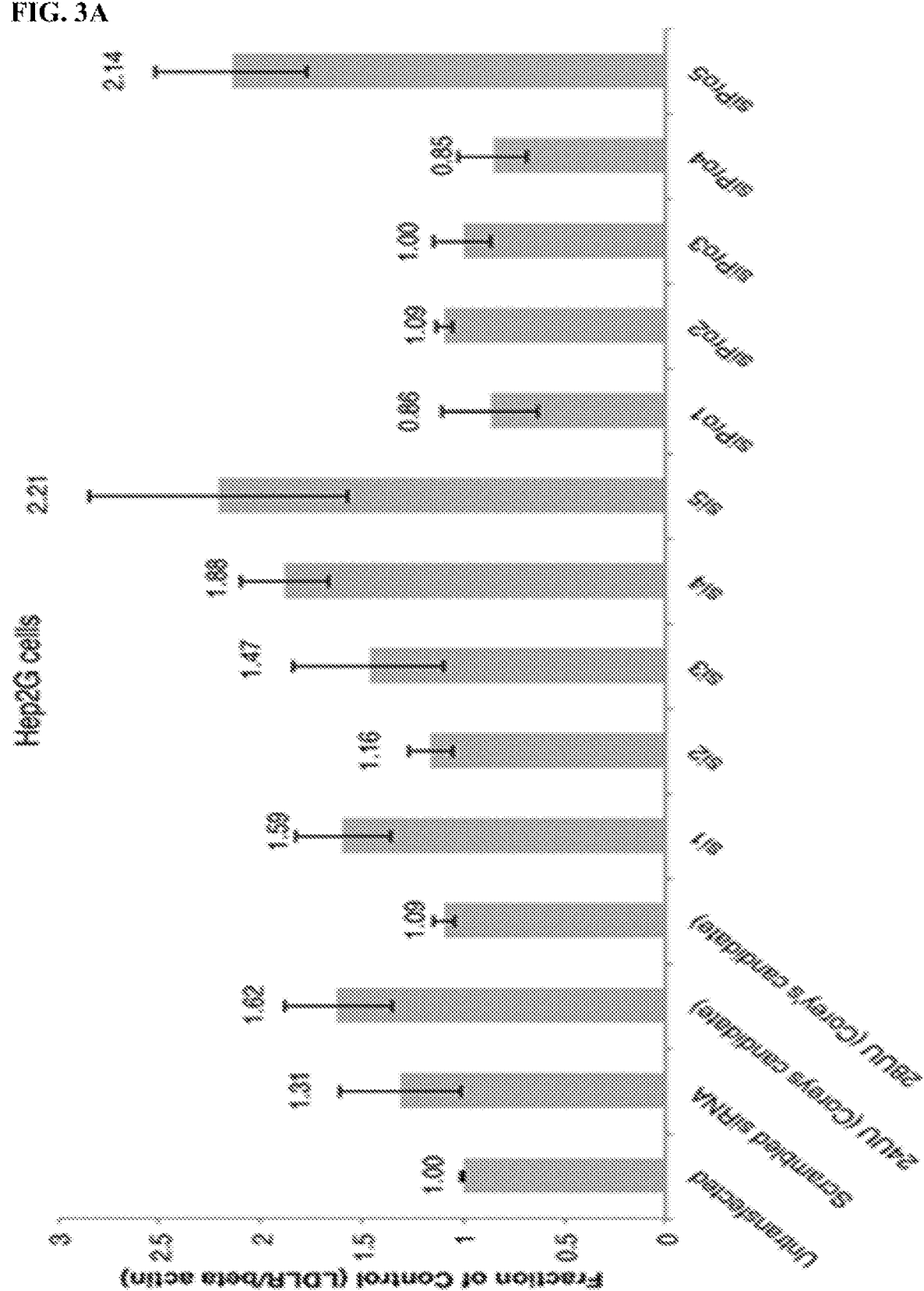
FIGS. 3A-3B. siRNA screen for activation of LDLR. siRNAs targeted to BM450697 lncRNA and BM450697 lncRNA promoter sequence in (FIG. 3A) Hep2G or (FIG. 3B) Hep3B liver cells. The average of triplicate treated cells are shown with the standard error of the means.
Figure 3B:
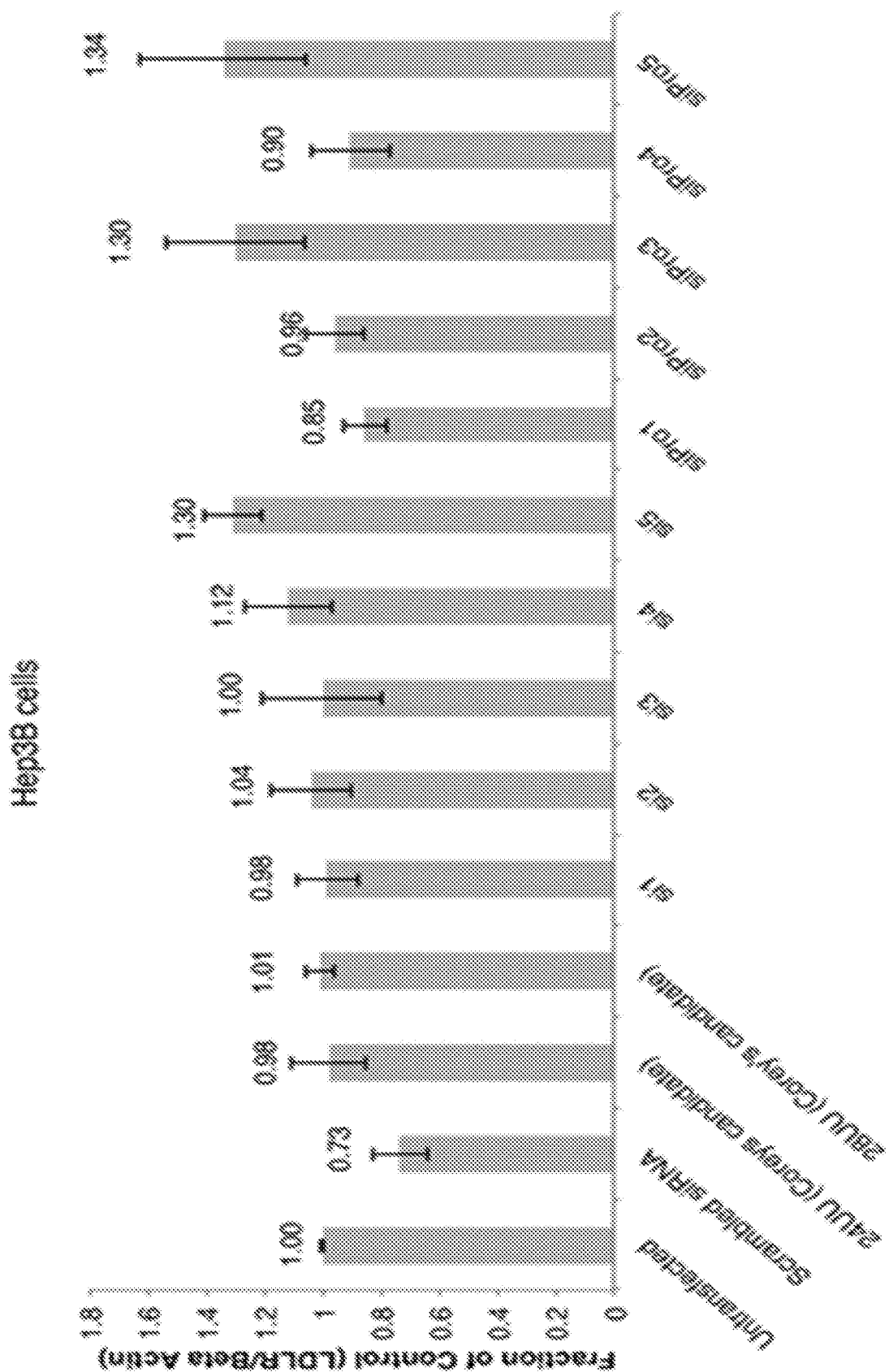

Cholesterol is removed from the blood by the Low-density lipoprotein receptor (LDLR) in the liver. Applicants and others have discovered that a long non-coding RNA (lncRNA), (EST BM450697; SEQ ID NO:2), functions as an endogenous epigenetic regulator of LDLR and that the repression of this lncRNA, by the action of small RNAs, results in the activation of LDLR. Applicants have found small RNAs that can target this lncRNA. Two small RNAs, BM45-si3 (SEQ ID NO:17 and SEQ ID NO:18), also referred to herein as si3, and BM45-si5 (SEQ ID NO:21 and SEQ ID NO:22), also referred to herein as si5 or 5, function in the RNAi pathway driving post-transcriptional gene silencing and is transient in its affect. Another small RNA, BM45-pro-si5 (SEQ ID NO:11 and SEQ ID NO:12), also referred to herein as prosi_5 or p5, functions in the transcriptional gene silencing (TGS) pathway and epigenetically silences the lncRNA's promoter (SEQ ID NO:1). Acting through the TGS pathway results in long-term, stable activation of LDLR, and subsequent stable reduction of cholesterol. Applicants find that both siRNAs target the repression of BM450697 which leads to the activation of LDLR expression (FIGS. 1A-1C).

The target gene is located in the liver. siRNAs are known to go to the liver and can be enhanced in liver targeting by the addition of GalNac conjugates. Therefore, delivery is relatively straightforward by injection of the regulatory RNAs into the blood.

Furthermore, because the small RNA BM45-pro-si5 functions through TGS and offers long term activation of LDLR, therapeutics effects can be achieved with minimal dosing.

Targeting the lncRNA with siRNAs allows for post-transcriptional gene silencing (PTGS) mediated via the RNAi pathway. Targeting of the lncRNA promotor functions in the transcriptional gene silencing (TGS) pathway and results in epigenetic silencing of the lncRNA promoter. Both PTGS and TGS mediated repression of lncRNA lead to decreases in the amount of intracellular lncRNA and concomitant increases in LDLR activation or expression. PTGS mediated lncRNA repression results in a transient decrease of lncRNA, while TGS mediated repression of lncRNA results in sustained lncRNA repression. Sustained lncRNA repression through the TGS pathway provides an opportunity for therapeutic effects to be achieved through minimal dosing.

Example 2

Applicants envision using the candidate siRNAs or small antisense RNAs with various stabilizing chemical backbone-modifications such as [2'4']-locked ribonucleotide, 2'-O-methyl-ribonucleotide, 5-methyl-cytosine, or phosphorothioate linkage. Applicants also envision conjugating these siRNAs or small RNAs with cholesterol or Trivalent (triantennary) N-acetylgalactosamine (GalNAc) to deliver the candidate RNAs directly to the liver in either transgenic mice or humans. Delivery of the candidate siRNAs directly to the liver will result in targeting only those cells where LDLR is preferentially expressed. Notably both cholesterol and GalNAc specifically deliver siRNAs or small antisense RNAs to the liver in humans and mice.

Example 3

Hepatocellular carcinoma cell lines, HepG2 and Hep3B (ATCC) were cultured in minimum essential media (MEM, Gibco) supplemented with 10% fetal bovine serum (Gibco) and 100 U/mL penicillin, 0.1 mg/mL streptomycin (Sigma), at 37° C. in a water-jacket incubator. Cells were transfected with duplex siRNAs using Lipofectamine RNAiMAX (Invitrogen) in Opti-MEM (Gibco). Briefly, the diluted siRNAs in Opti-MEM were added to RNAiMAX in opti-MEM and incubated at room temperature for 20 minutes. Hep3B cells were plated at a density of 75,000 cells/24 well plate and transfected the next day with the duplex siRNAs using 1.5 uL RNAiMAX per condition. HepG2 cells were reverse transfected at a density of 75,000 cells/24 well plate with 50 nM siRNA using 2.4 uL RNAiMAX per condition. Media was replaced the following day, and cells were harvested 72 hours post transfection. RNA was isolated using the SimplyRNA RNA isolation kit (Promega) according to the manufacturer's instructions. cDNA was synthesized by reverse transcribing 100 ng total RNA using an MM-LV reverse transcriptase (Invitrogen). Real time quantitative PCR was performed using 2× fast universal qPCR mix (Kapa Biosystems, Woburn, Mass.) according to the manufacturer's instructions and a Roche Lightcycler® 96 real time PCR system (Roche). Thermal cycling parameters started with 3 minutes at 95° C., followed by 40 cycles of 95° C. for 3 seconds and 60° C. for 30 seconds. Specificity of the PCR products was verified by melting curve analysis. The following primers were used for qPCR: LDLR F: 5'-ACCCCTCGAGACAGATGGTCA-3' (SEQ ID NO:24); primer LDLR R: 5'-GGCACTGTCCGAAGCCTGTT-3' (SEQ ID NO:25); (3-actin F: 5'-AGGTCATCACCAT-TGGCAATGAG-3' (SEQ ID NO:26); (3-actin R: 5'-TCTTTGCGGATGTCCACGTCA-3' (SEQ ID NO:27). Relative LDLR levels were determined using the delta-delta Cq method, calibrating LDLR levels to the reference gene, (3-actin, with the un-transfected control set to 1.

Example 4

The Low Density Lipoprotein receptor (LDLR) is a cell surface expressed protein that binds and internalizes low density lipoprotein (LDL), resulting in cholesterol being made available to the cell[1]. Loss of LDLR results in the autosomal dominant disorder familial hypercholesterolemia[1]. A method to specifically and stably over-express LDLR could theoretically result in increased removal of LDL from the blood and an overall lowering of cholesterol.

Previous studies have uncovered a ~1,450-nt antisense non-coding polyadenylated, unspliced transcript, EST BM450697 (SEQ ID NO:2), that overlaps the LDLR promoter[2]. This transcript is expressed at levels approximately 90-fold below LDLR mRNA and when repressed results in a concomitant increase in LDLR expression[2], suggesting that BM450697 and LDLR are discordantly linked.

Figure 4:
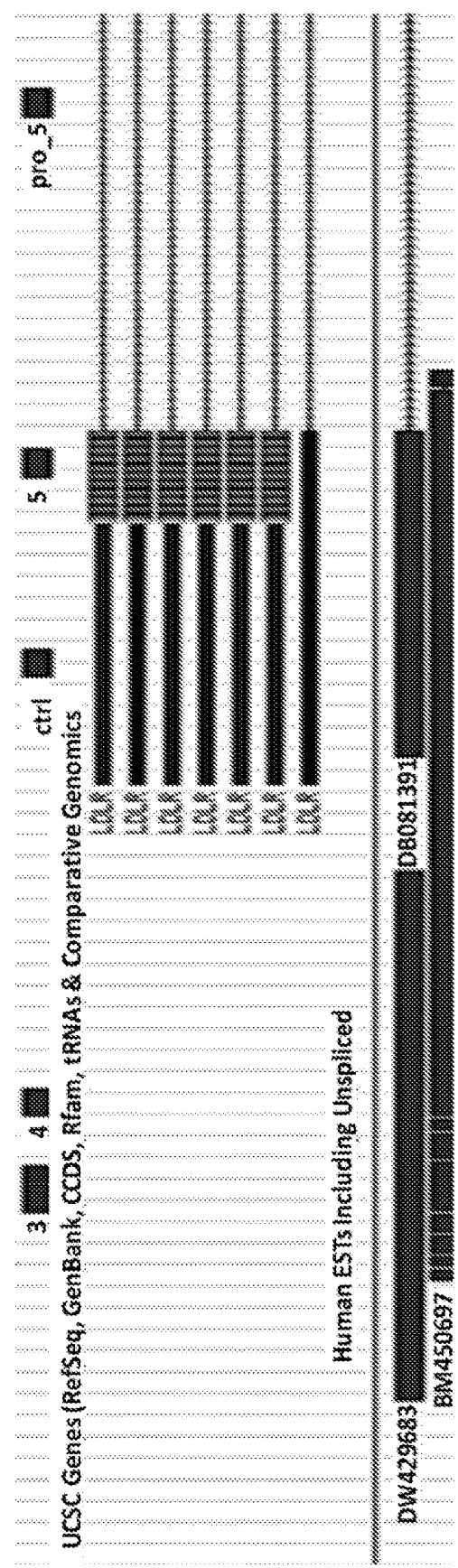
FIG. 4. A schematic diagram illustrating the loci of the target siRNAs towards the lncRNA EST BM450697. The LDLR gene, 5' UTR, is also shown.

Applicants investigated the role of BM450697 on LDLR gene expression and screened several siRNAs targeted towards either BM450697 or its promoter in two hepatocellular carcinoma cell lines, Hep3B and HepG2 (FIG. 4).

Figure 5A:
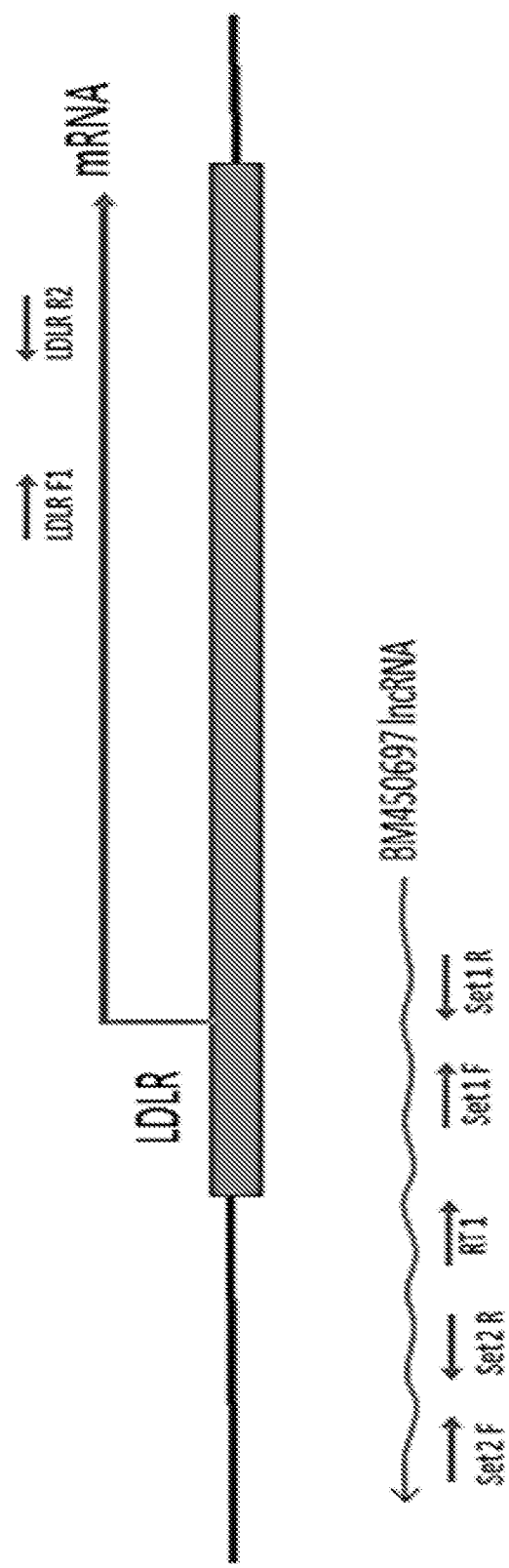
FIGS. 5A-5B.
Figure 5B:
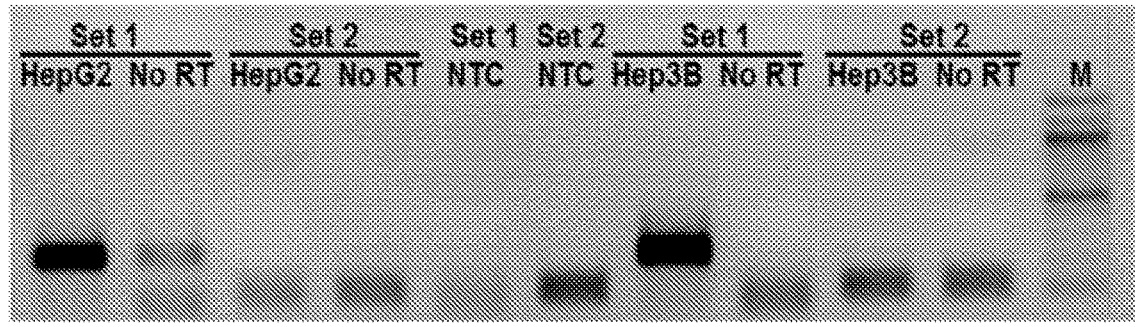

HepG2 and Hep3B cell lines expressed the lncRNA, BM450697, following transfection (FIGS. 5A and 5B).

Figure 6A:
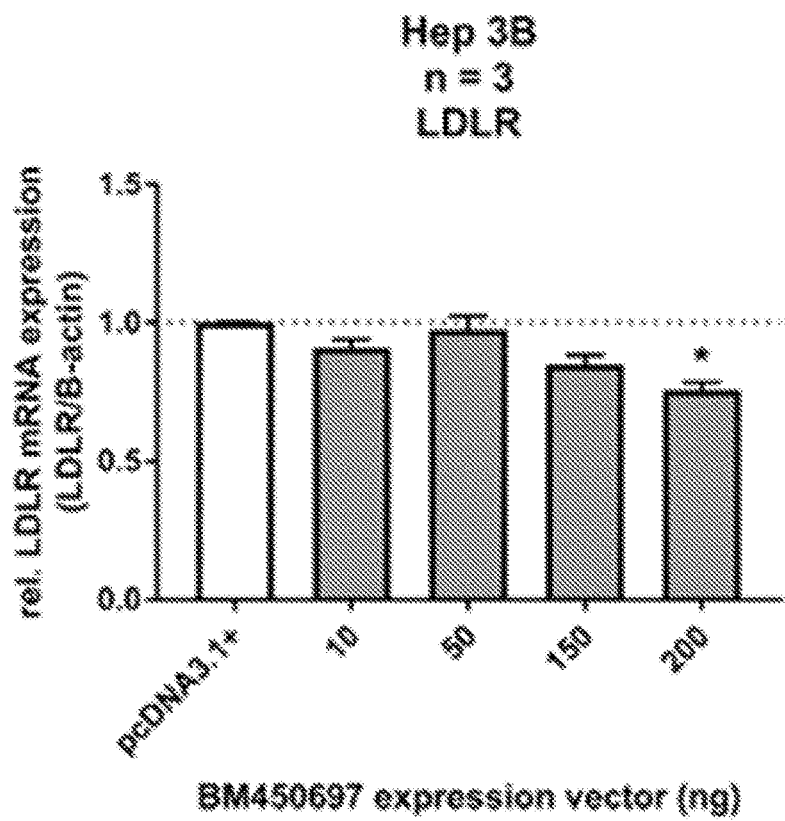
FIGS. 6A-6D. Hep3B and HepG2 cells were transfected with increasing concentrations of BM450697 using Lipofectamine 3000 (Invitrogen). Cells were harvested 48 hours later and RNA processed (SimplyRNA, Promega). 100 ng total RNA was reverse transcribed to cDNA using an MM-LV reverse transcriptase (Invitrogen), and qPCR was performed. Relative (FIG. 6A and FIG. 6C) LDLR and (FIG. 6B and FIG. 6D) BM450697 expression levels in Hep3B and HepG2 are shown, respectively.
Figure 6B:
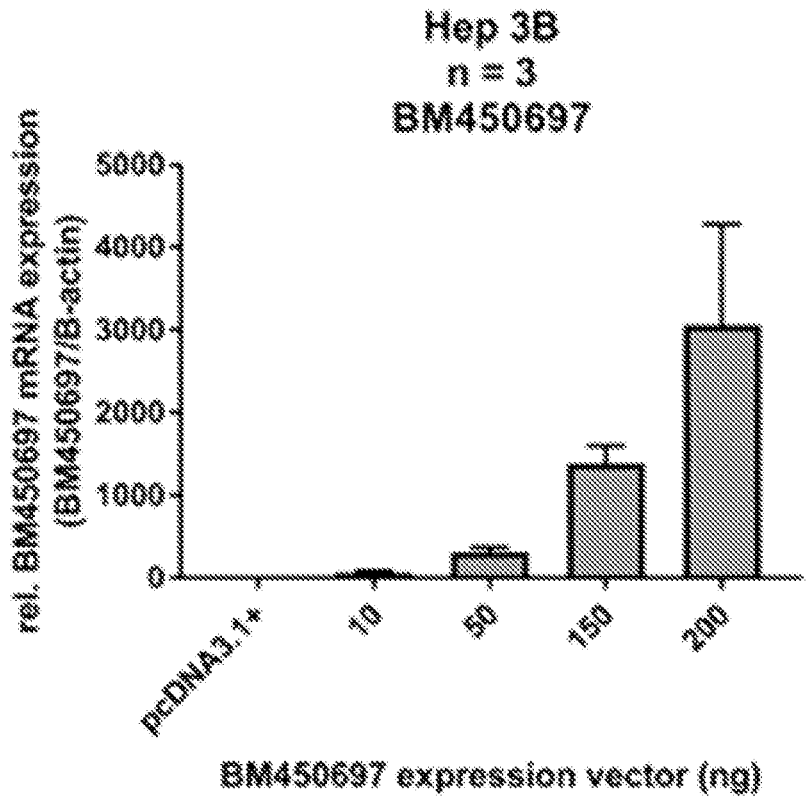
Figure 6C:
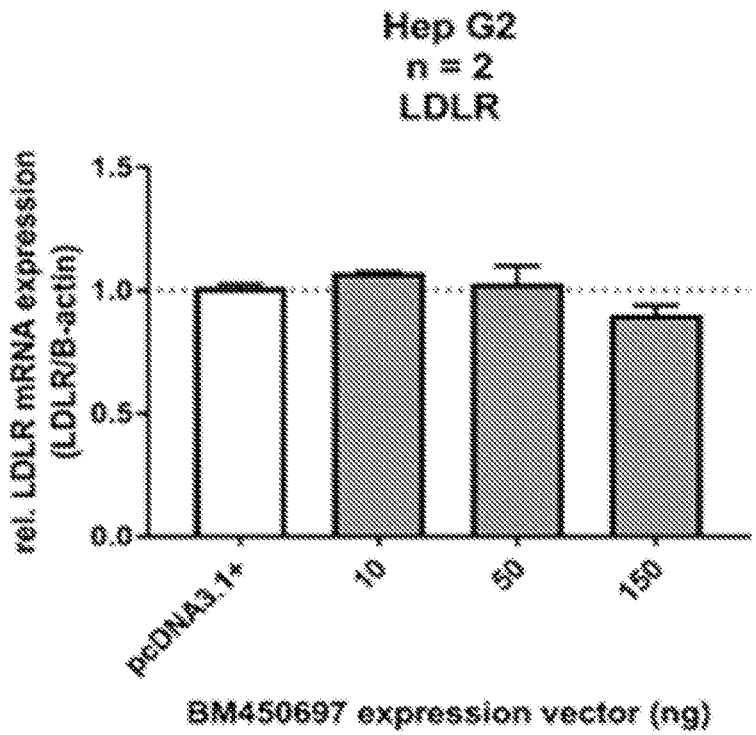
Figure 6D:
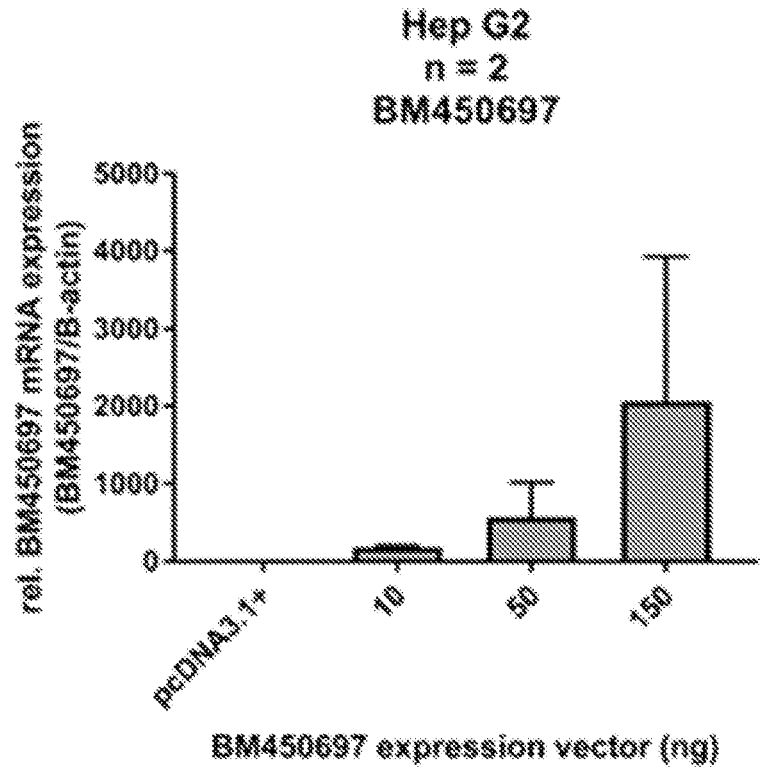
Figure 7A:
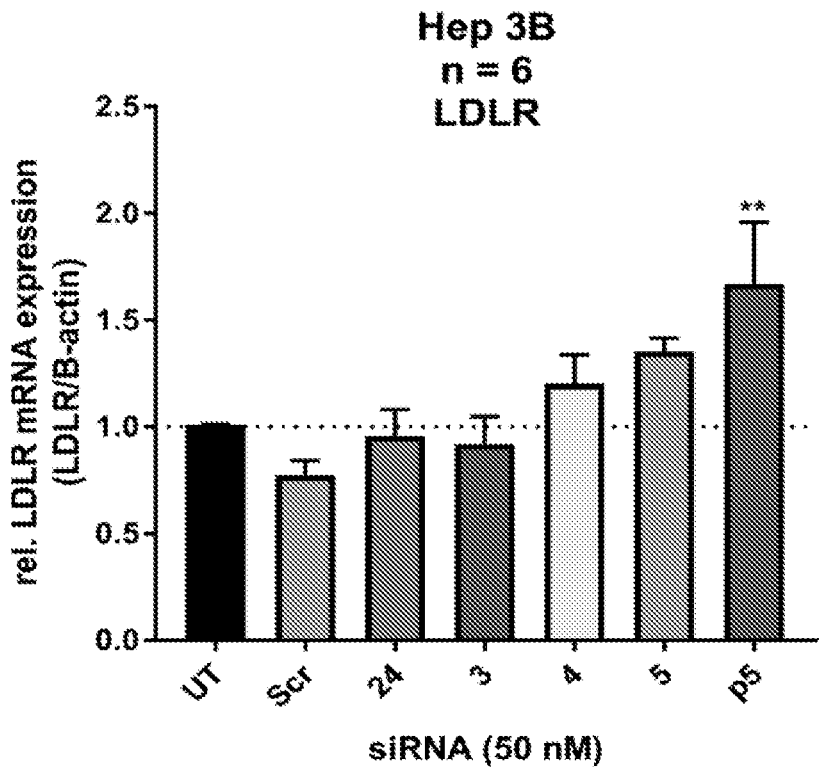
FIGS. 7A-7D. Hep3B and HepG2 cells were transfected with 50 nM duplex siRNAs using lipofectamine RNAiMAX (Invitrogen). Cells were harvested 72 hours later and processed for RNA (SimplyRNA, Promega). 100 ng total RNA was reverse transcribed to cDNA using an MM-LV reverse transcriptase (Invitrogen), and qPCR was performed. Relative (FIG. 7A and FIG. 7C) LDLR and (FIG. 7B and FIG. 7D) BM450697 mRNA expression levels in Hep3B and HepG2 cells respectively.
Figure 7B:
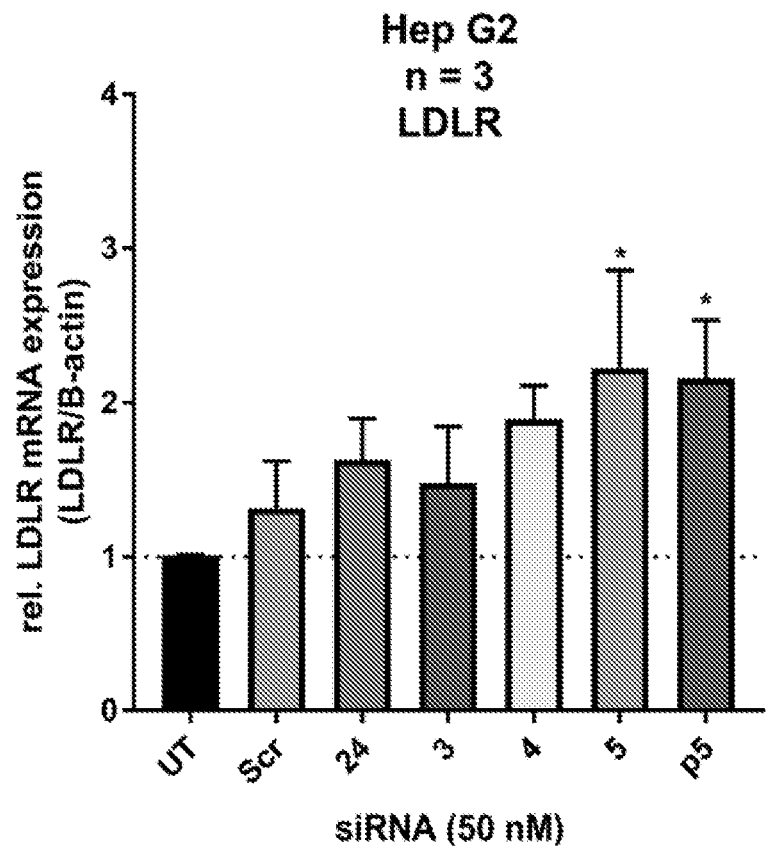
Figure 7C:
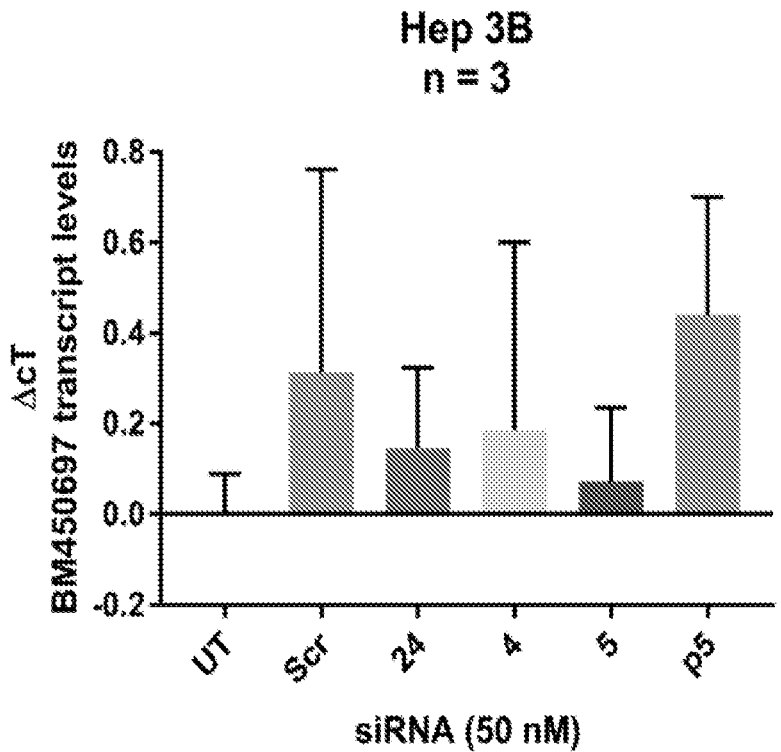
Figure 7D:
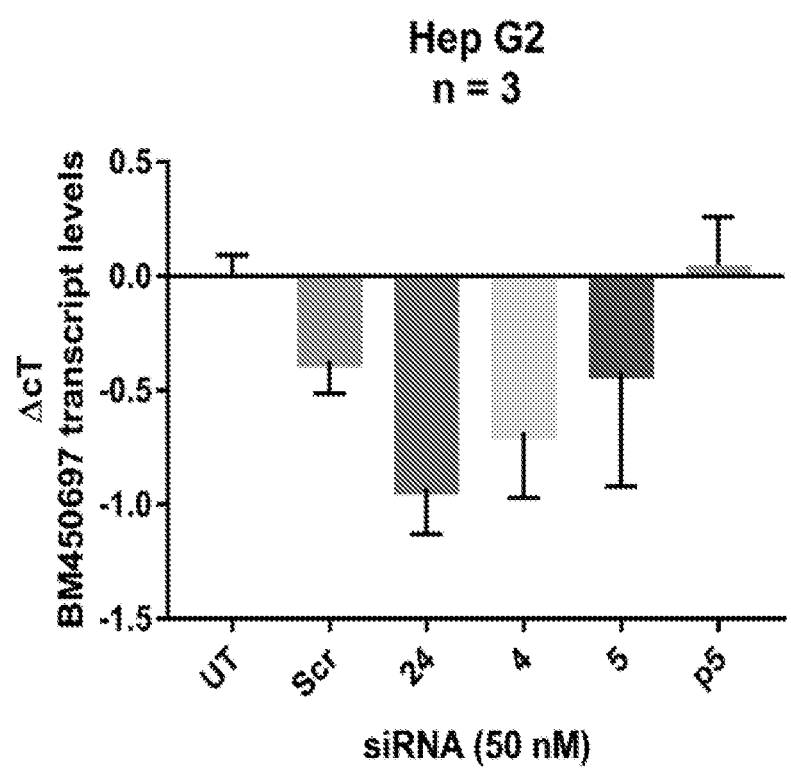

BM450697 overexpression resulted in a concomitant decrease in LDLR mRNA expression (FIGS. 6A and 6C).

siRNA duplexes, si5 (SEQ ID NO:21 and SEQ ID NO:22) and p5 (SEQ ID NO:11 and SEQ ID NO:12), repress BM450697 (FIGS. 7C and 7D) which results in increased LDLR mRNA expression (FIGS. 7A and 7B).

Figure 8A:
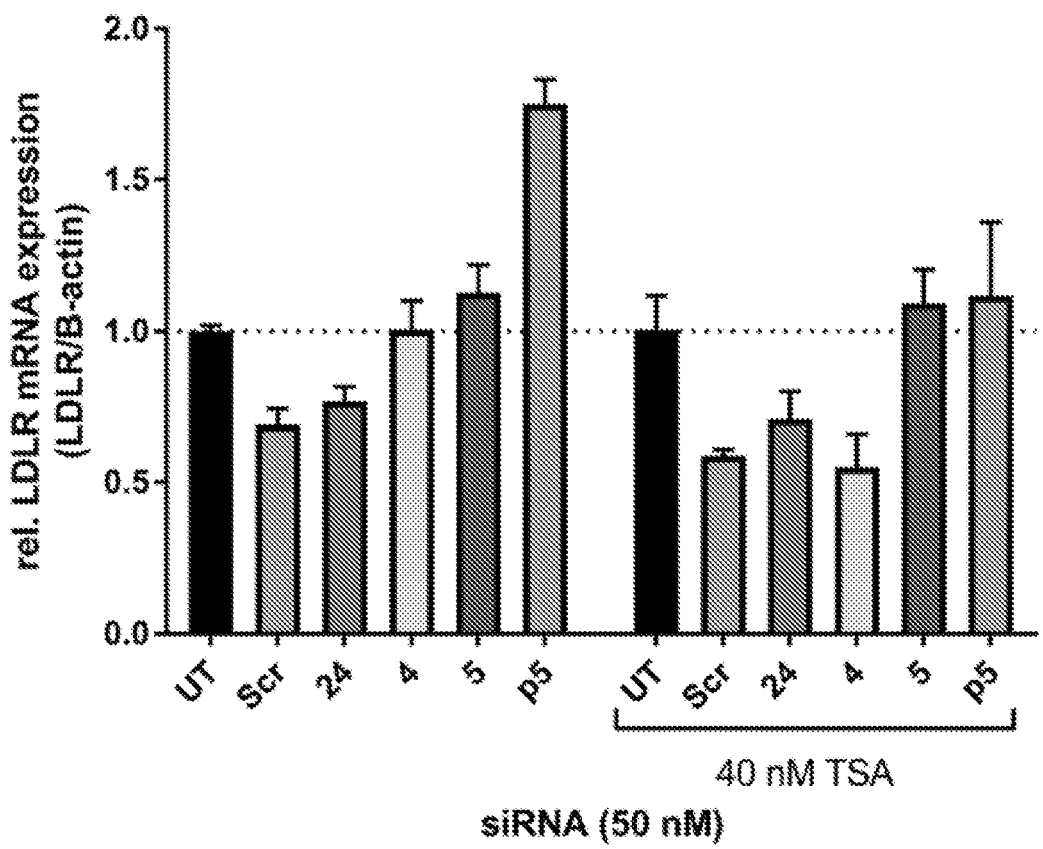
FIGS. 8A-8B. Hep3B and HepG2 cells were transfected with 50 nM duplex siRNAs using lipofectamine RNAiMAX (Invitrogen). 24 hours later, media was replaced with or without 40 nM trichostatin A (TSA, Simga). Cells were harvested a further 48 hours later and processed for RNA (SimplyRNA, Promega). 100 ng total RNA was reverse transcribed to cDNA using an MM-LV reverse transcriptase (Invitrogen), and qPCR was performed. Relative (FIG. 8A and FIG. 8B) LDLR mRNA expression levels were measured in Hep3B and HepG2 cells respectively.
Figure 8B:
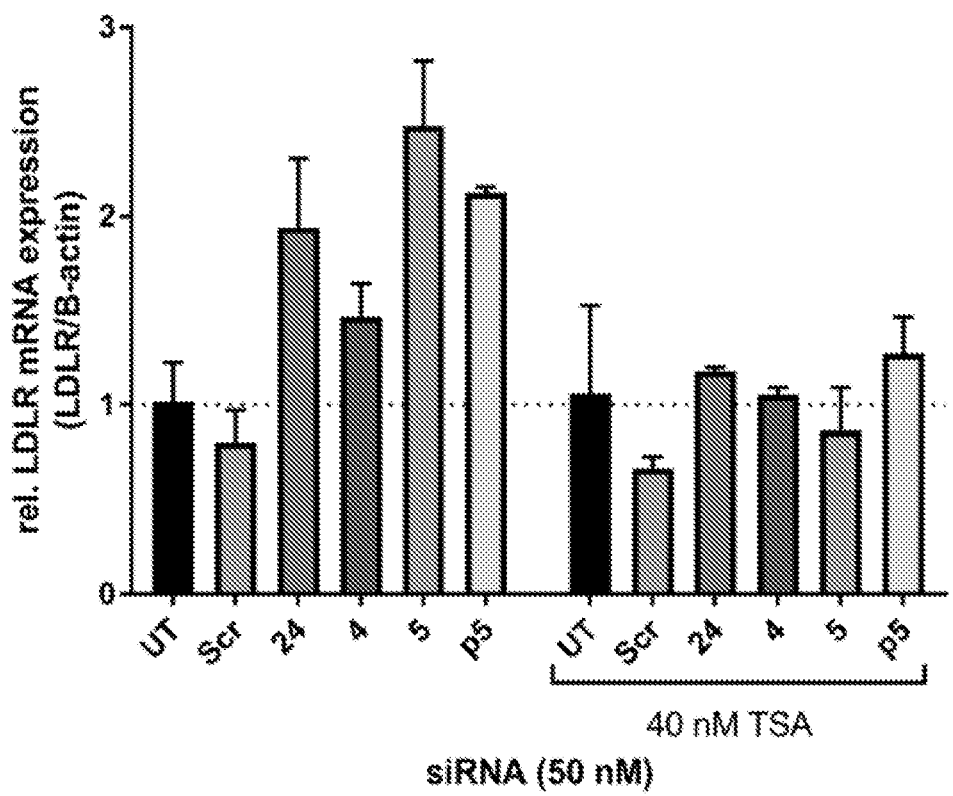
Figure 9A:
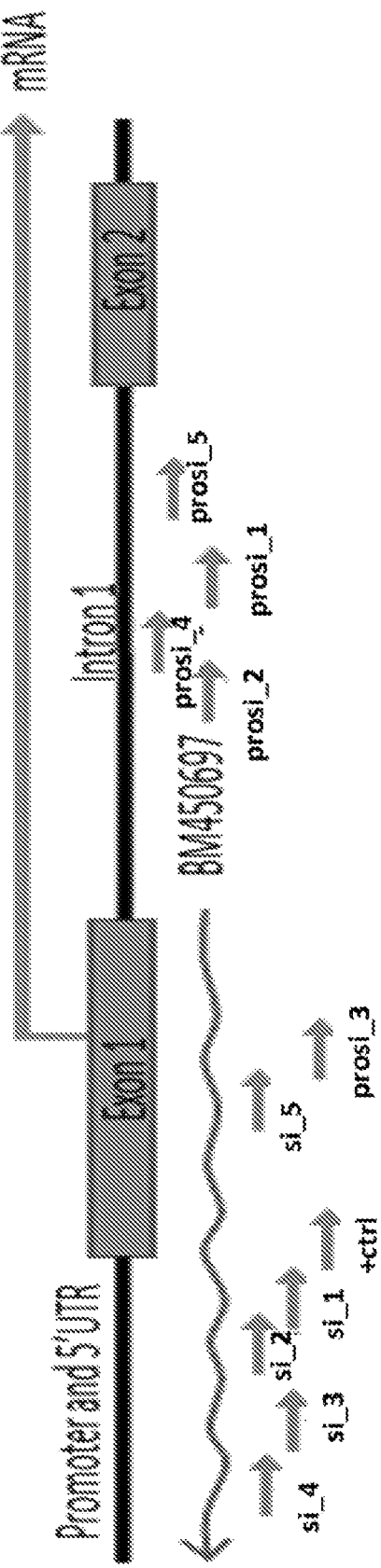
FIGS. 9A-9D. siRNA targeted towards the lncRNA and the promoter of the lncRNA, increase LDLR expression in Hep3B and HepG2 cells.
Figure 9B:
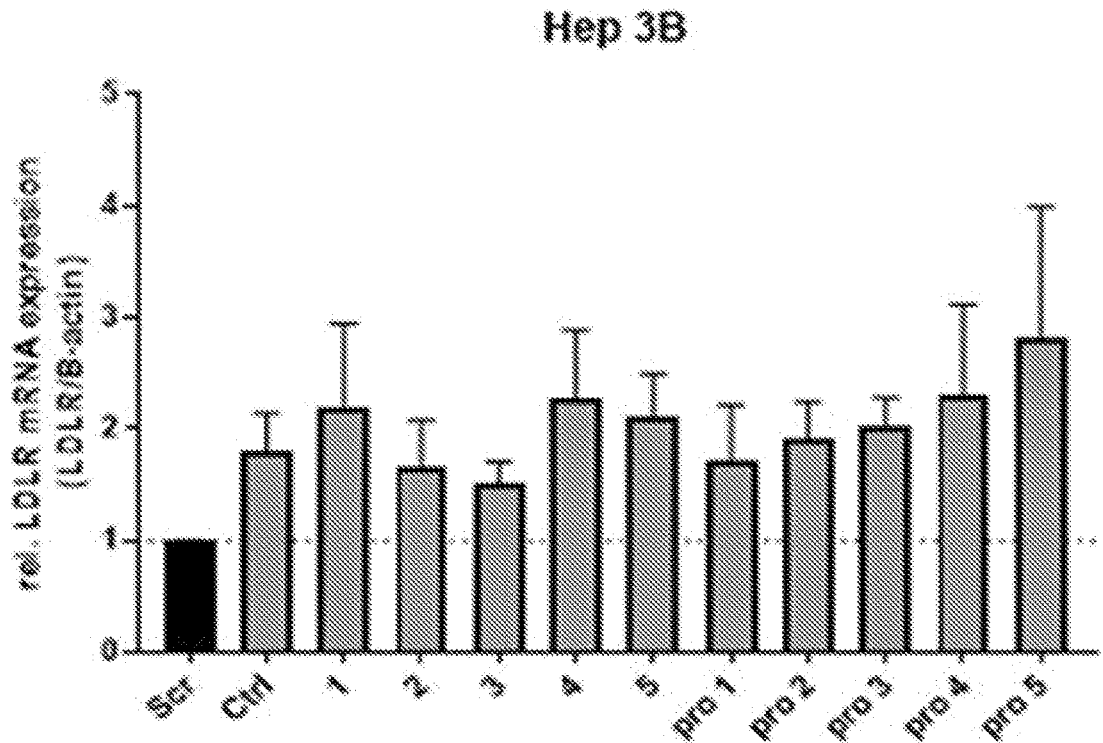
Figure 9B:
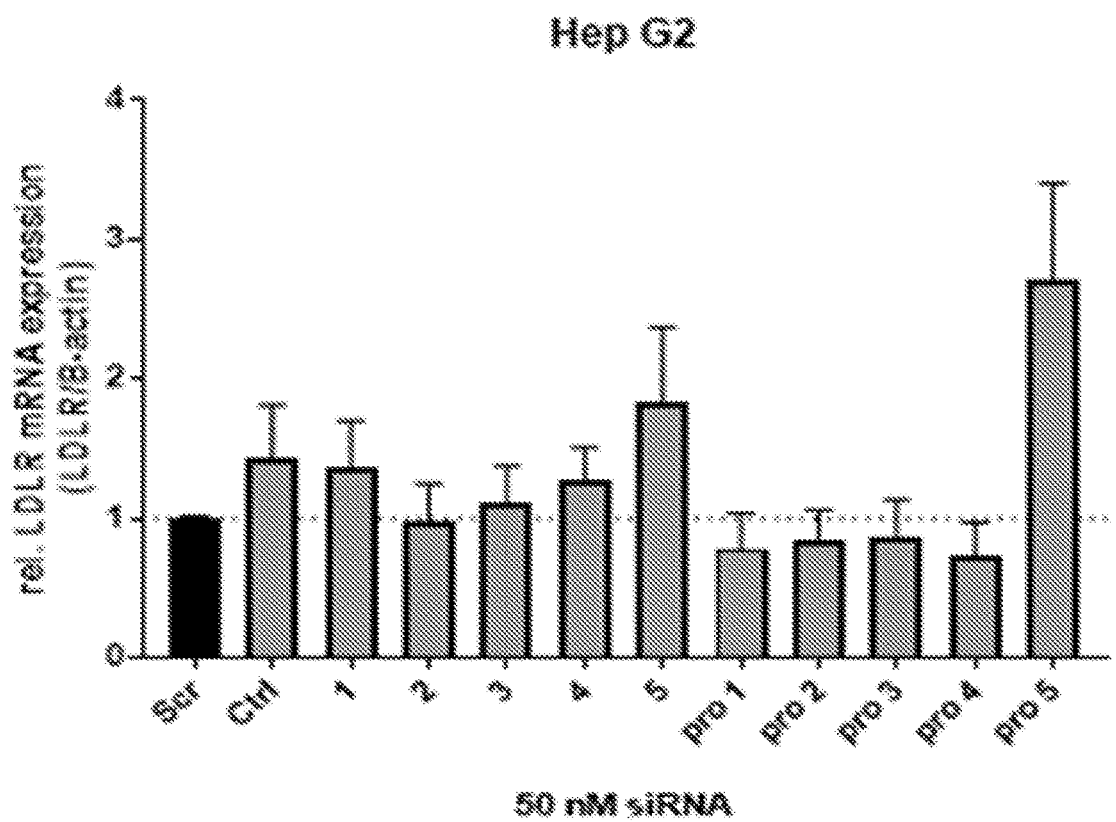
Figure 9C:
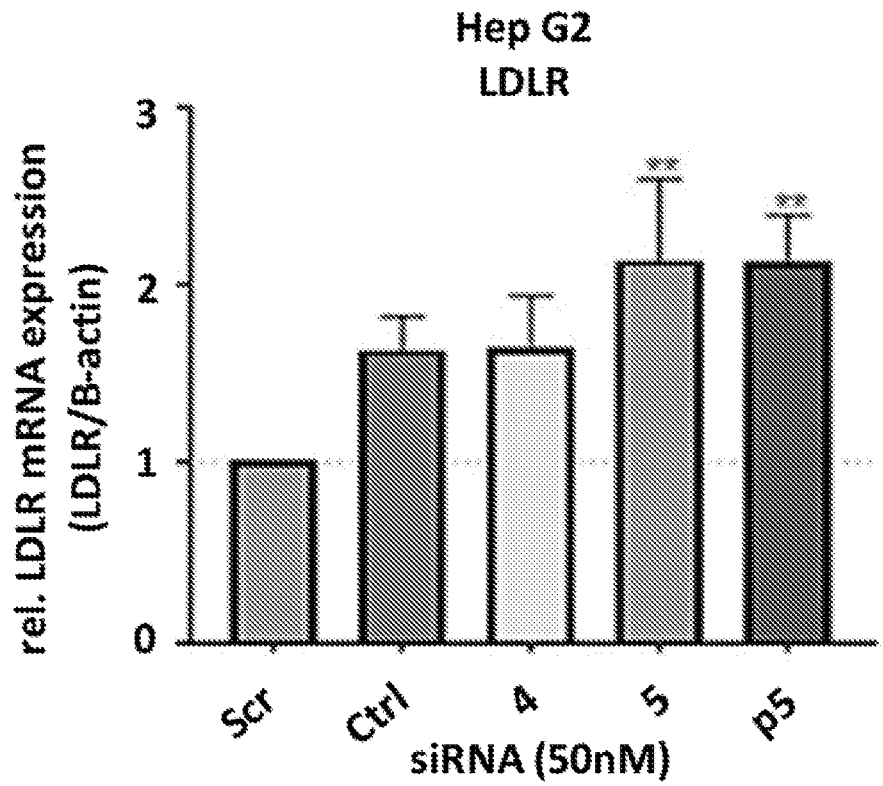
Figure 9C:
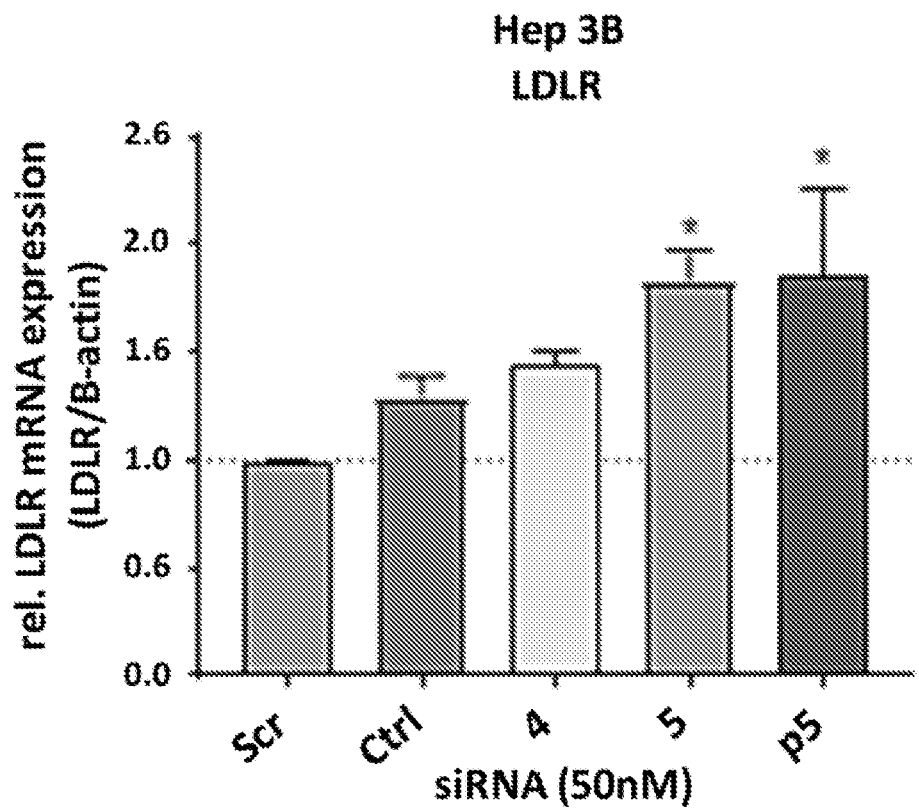
Figure 9D:
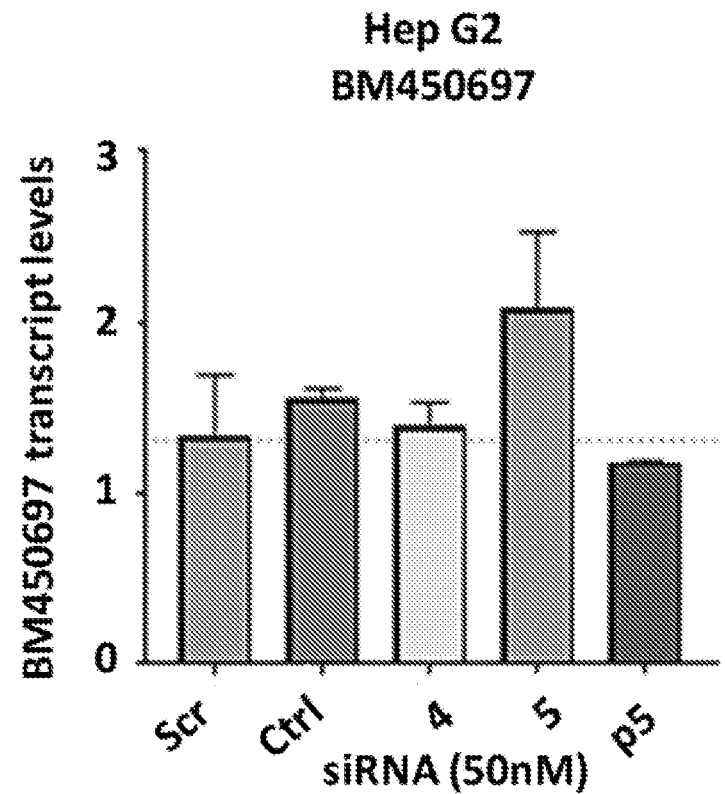
Figure 9D:
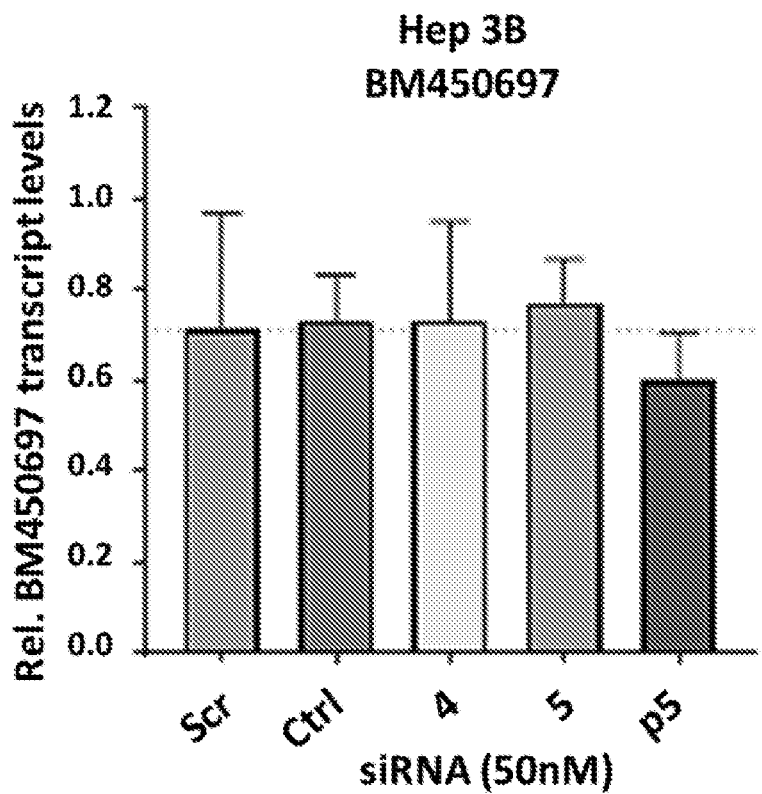

The si5 and p5 mediated increase in LDLR mRNA expression levels are reduced when treated with the HDAC inhibitor, Trichostatin A (TSA) (FIGS. 8A and 8B).

The lncRNA BM450697 is a regulator of LDLR receptor expression as established by the overexpression studies.

siRNA, p5, targeted to the promoter of BM450697 (SEQ ID NO:1), exhibited the most consistent effect on repression of BM450697 and activation of LDLR expression in both Hep3B and HepG2 cells.

The effects of p5 on BM450697 expression appear in both Hep3B and HepG2 cell lines to be epigenetic based as TSA inhibits the observed repression of BM450697 induced by siRNA p5.

Future studies will determine if the lncRNA BM450697 binds directly to the promoter of the LDLR gene and what co-factors may be recruited to this region to mediate the observed transcriptional effects.

Example 5 siRNA targeted towards the lncRNA and the promoter of the lncRNA, increase LDLR expression in Hep3B and HepG2 cells. Hep3B and HepG2 cells were transfected with 50 nM duplex siRNAs using lipofectamine RNAiMAX (Invitrogen). Cells were harvested 72 hours later and processed for RNA (SimplyRNA, Promega). 100 ng total RNA was reverse transcribed to cDNA using an MM-LV reverse transcriptase (Invitrogen), and qPCR was performed. FIGS. 9A-9D show the relative LDLR and BM450697 mRNA expression levels in Hep3B and HepG2 cells.

Figure 10A:
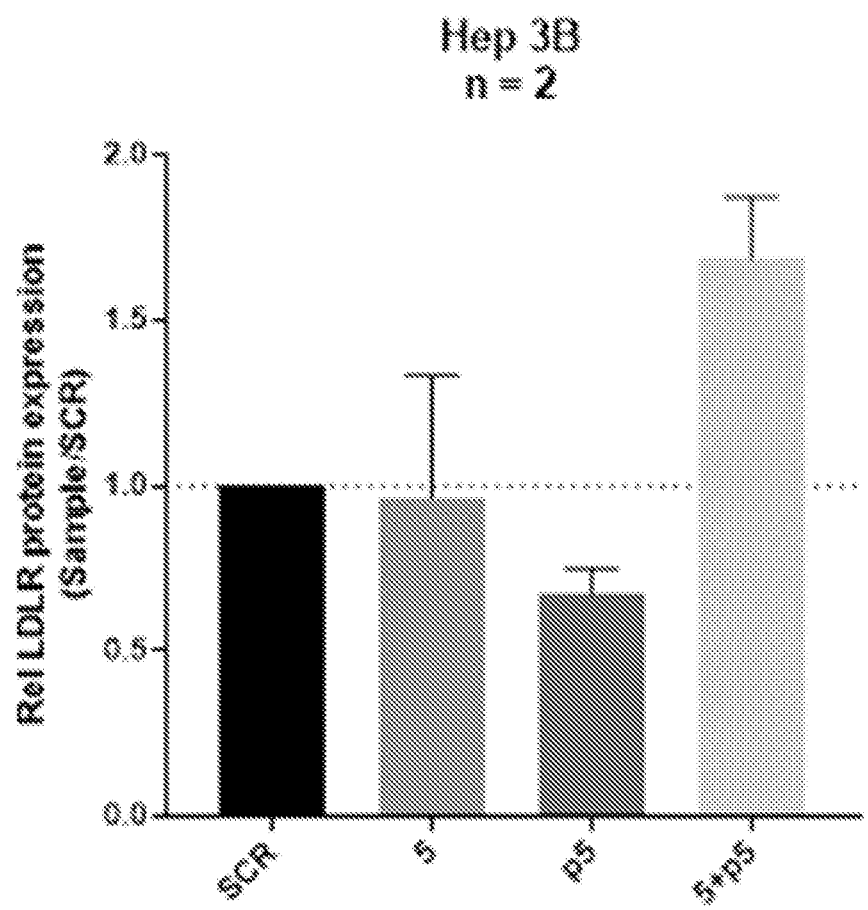
FIGS. 10A-10B. siRNAs targeted towards BM450697 increase LDLR protein expression in Hep3B cells.
Figure 10B:
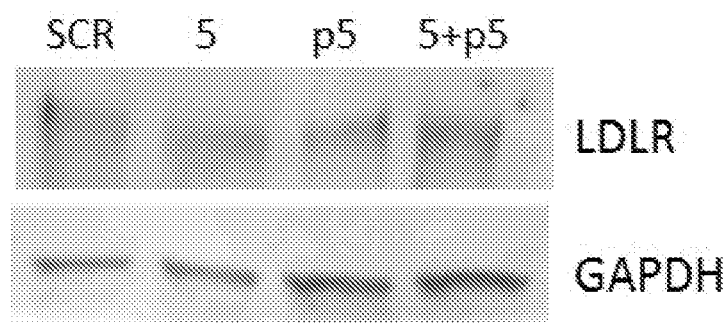
Figure 11A:
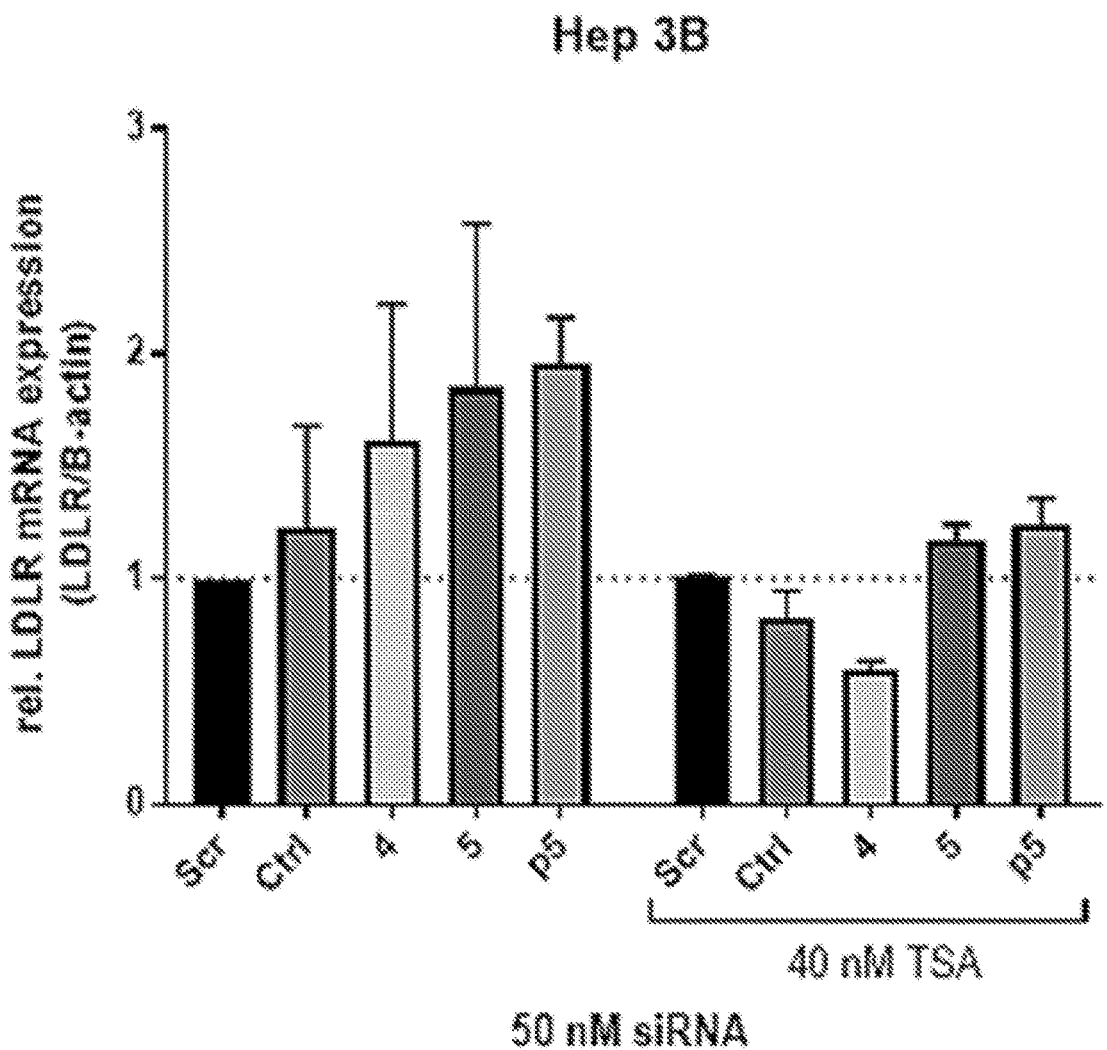
FIGS. 11A-11C. siRNA mediated silencing of BM450697 occurs in an epigenetic manner that results in an increase in LDLR mRNA expression.
Figure 11B:
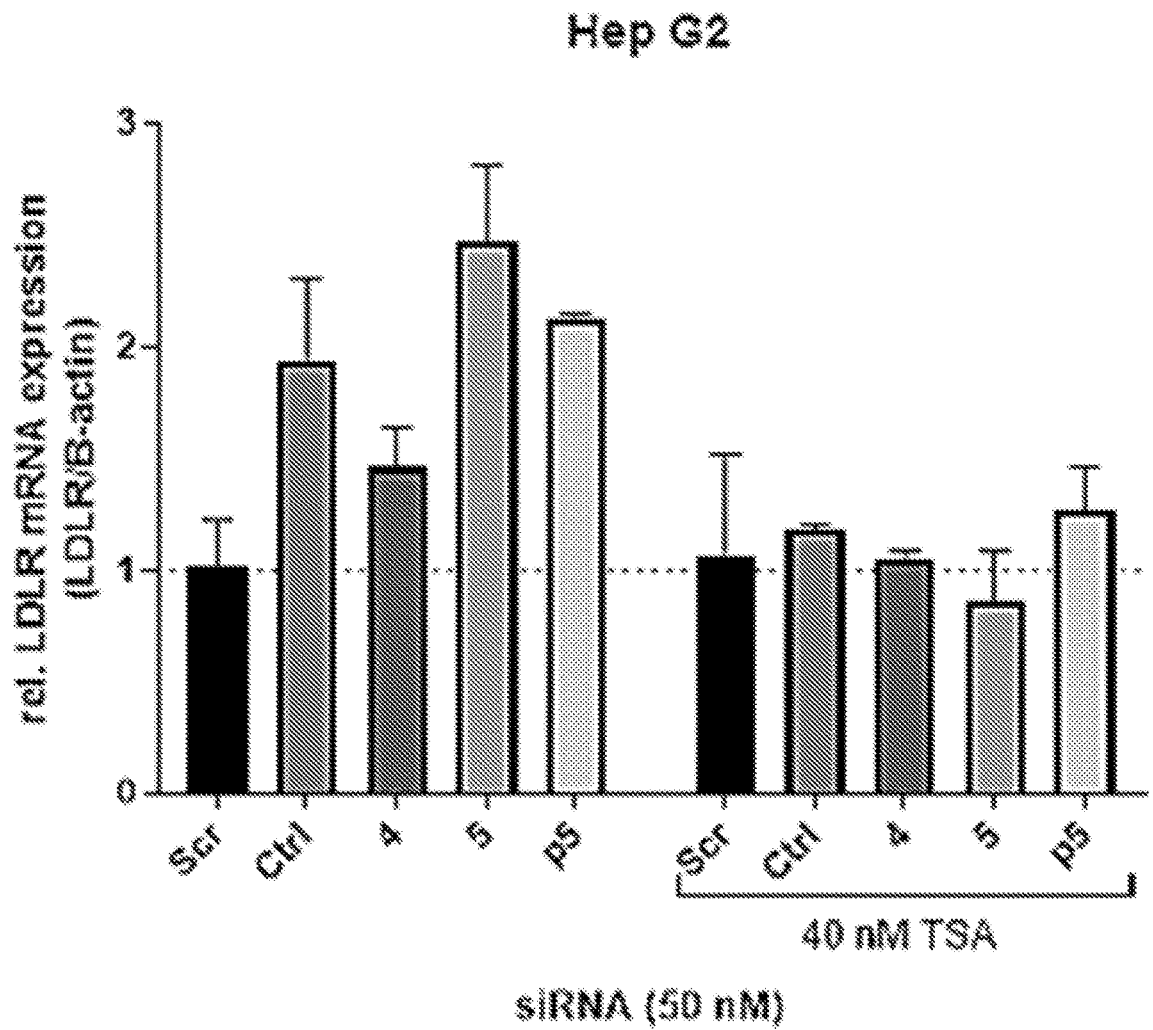
Figure 11C:
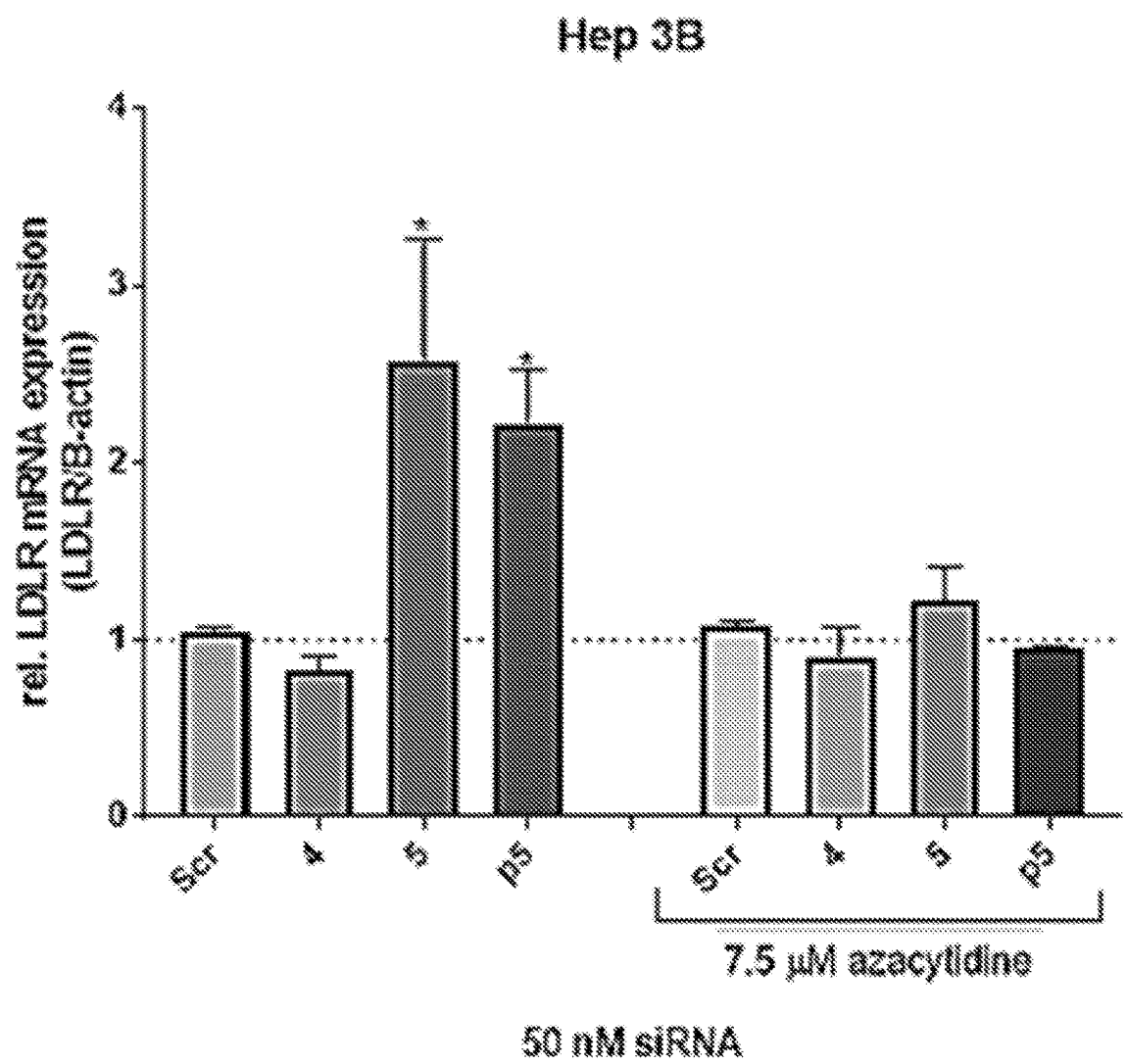

FIGS. 10A-10B demonstrate the ability of siRNAs targeted towards BM450697 increase LDLR protein expression in Hep3B cells. Hep3B cells were transfected with 50 nM duplex siRNAs alone or in combination, using lipofectamine RNAiMAX (Invitrogen). Cells were harvested 72 hours later and processed for protein. 1 mg protein was incubated with 5 primary LDLR antibody (Santa Cruz, USA). Thereafter, antibody-bound LDLR was isolated using protein G beads. Resultant IPs and 50 µg of total input protein were separated using SDS-PAGE and subsequently transferred onto nitrocellulose membranes and probed for LDLR and GAPDH. Blots were visualized using enhanced ECL (Thermo Scientific, USA) on a Bio-Rad Imager. FIG. 10A shows relative LDLR protein expression levels in Hep3B while FIG. 10B is a representative blot from one IP.

siRNA mediated silencing of BM450697 occurs in an epigenetic manner that results in an increase in LDLR mRNA expression. Hep3B and HepG2 cells were transfected with 50 nM duplex siRNAs using lipofectamine RNAiMAX (Invitrogen) and co-incubated with either 40 nM Trichostatin A (TSA) or 7.5 uM 5' Azacytidine. Cells were harvested 72 hours later and processed for RNA (SimplyRNA, Promega). 100 ng total RNA was reverse transcribed to cDNA using an MM-LV reverse transcriptase (Invitrogen), and qPCR was performed. FIGS. 11A-11C show the relative LDLR mRNA expression levels as a function of treatment.

Figure 12A:
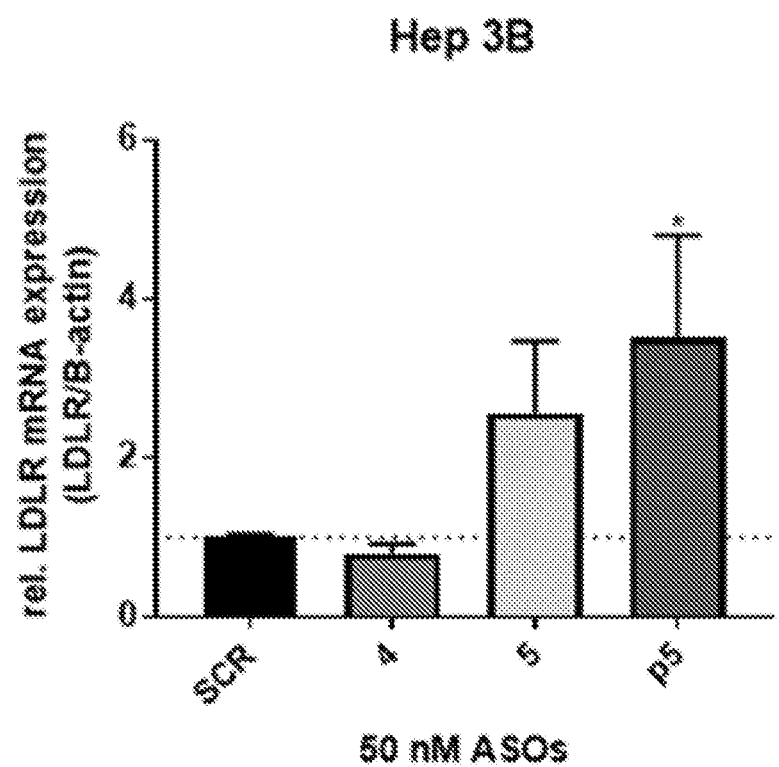
FIGS. 12A-12C. Antisense oligonucleotides increase LDLR mRNA expression and protein expression. Relative (FIG. 12A and FIG. 12C) LDLR mRNA expression levels, and relative LDLR protein expression, with gating strategy (FIG. 12B).
Figure 12B:
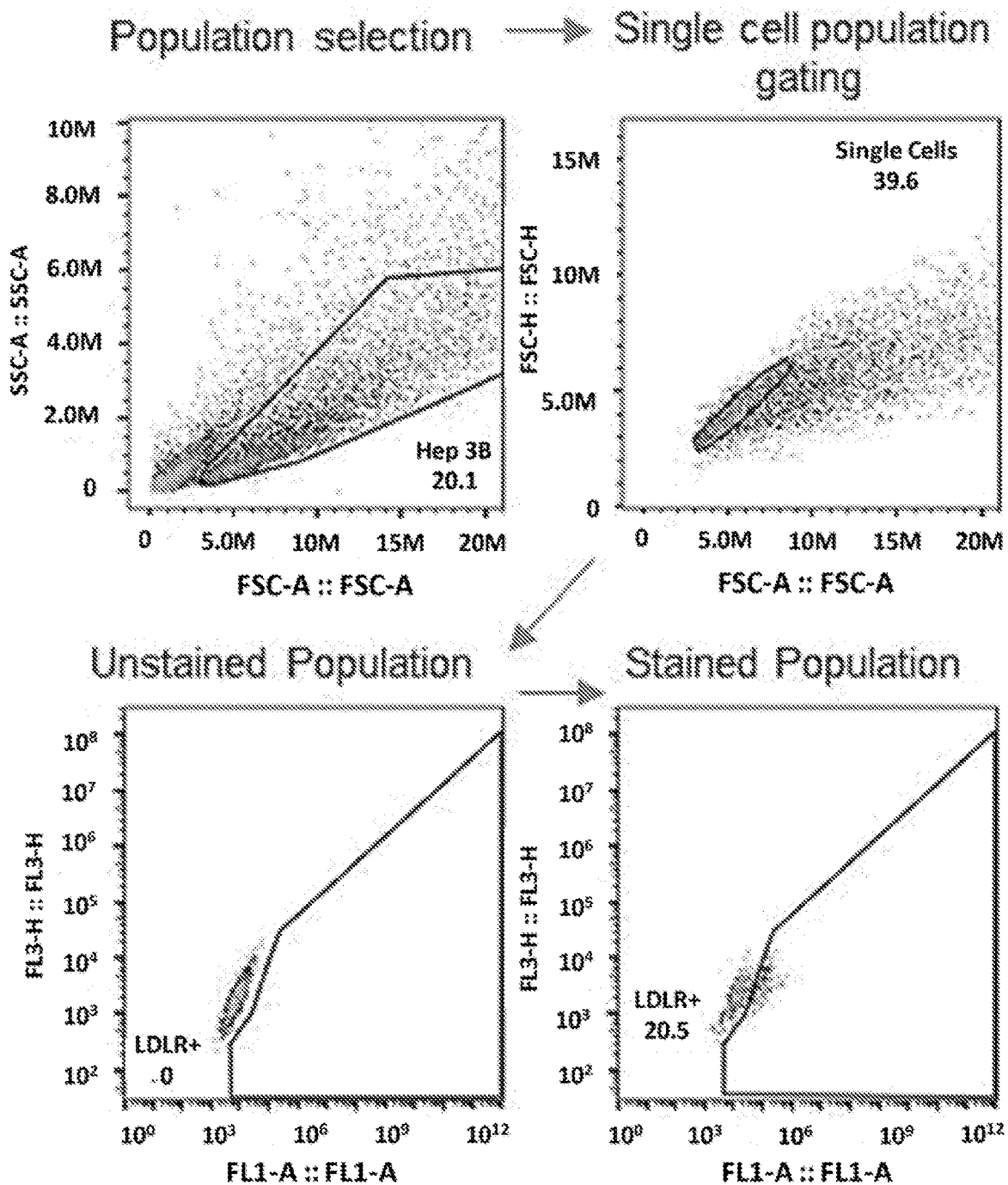
Figure 12C:
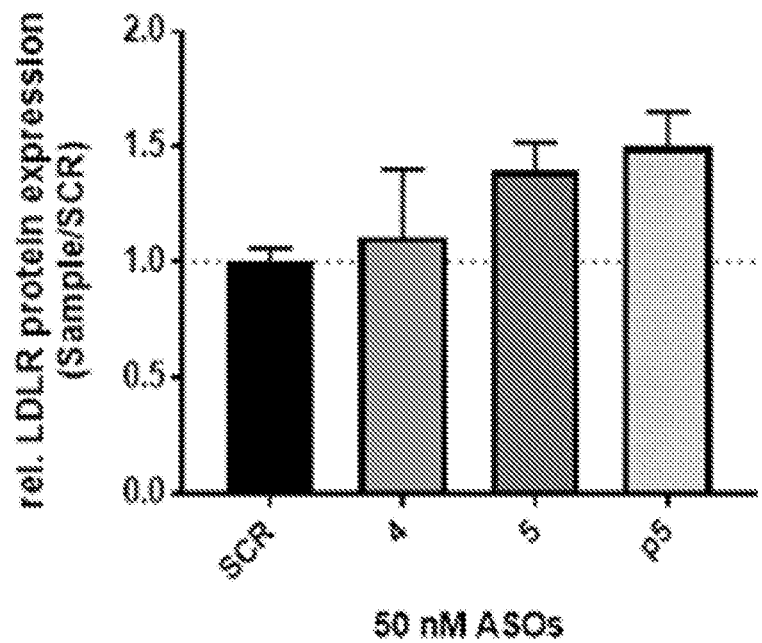
Figure 12C:
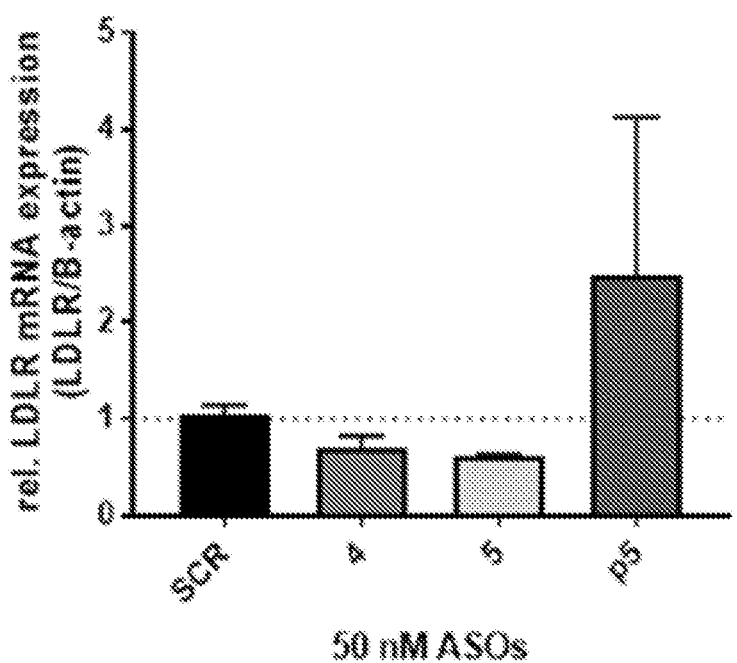

It was further demonstrated that antisense oligonucleotides increase LDLR mRNA and protein expression. Hep3B and HepG2 cells were transfected with 50 nM duplex ASOs using lipofectamine RNAiMAX (Invitrogen). Cells were harvested 72 hours later and processed for RNA (SimplyRNA, Promega) or for flow cytometry. 100 ng total RNA was reverse transcribed to cDNA using an MM-LV reverse transcriptase (Invitrogen), and qPCR was performed. FIGS. 12A and 12C show the relative LDLR mRNA expression levels and relative LDLR protein expression. FIG. 12B demonstrates the gating strategy.

Figure 13A:
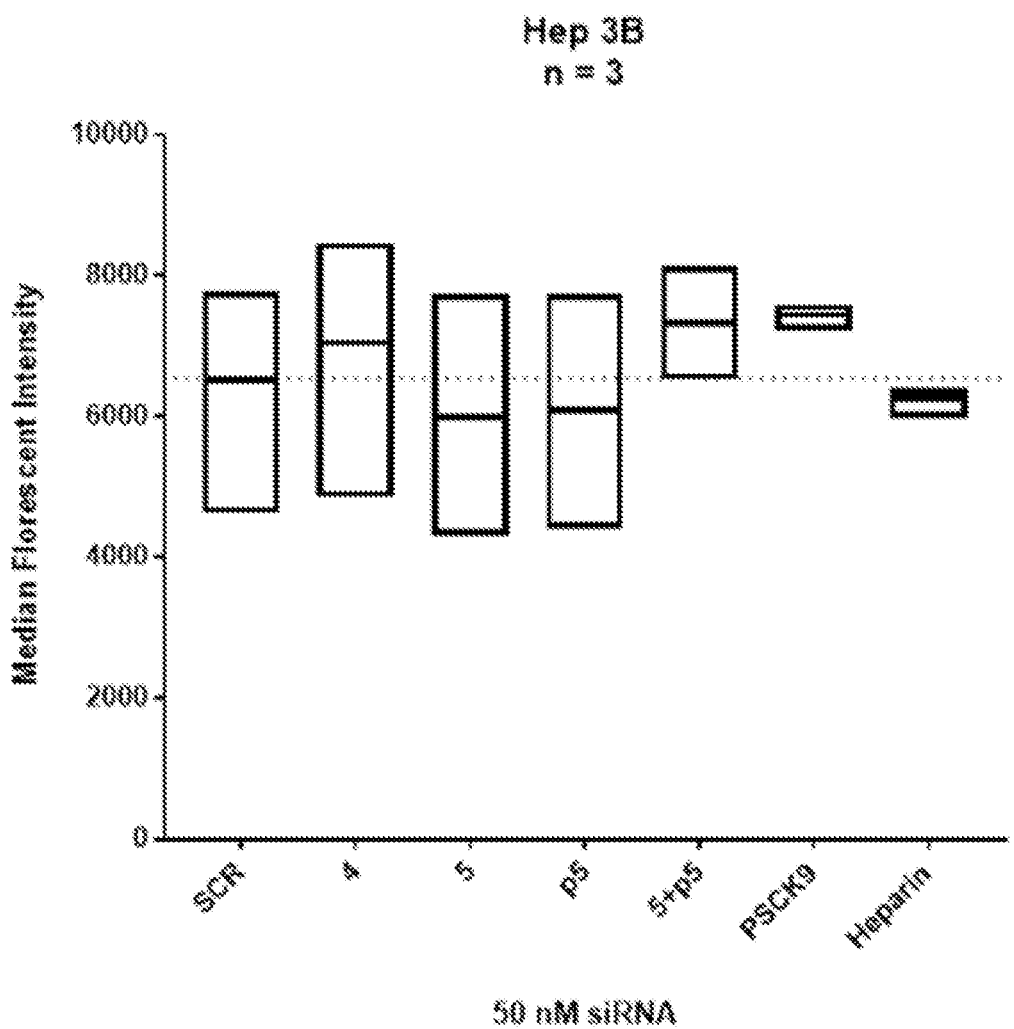
FIGS. 13A-13B. Effect on LDL uptake in Hep 3B cells of siRNAs. Hep3B cells were transfected with 50 nM duplex siRNAs using lipofectamine RNAiMAX (Invitrogen). Cells were harvested 72 hours later and processed for LDL uptake using the LDL uptake assay kit (Molecular Probes, Invitrogen).
Figure 13B:
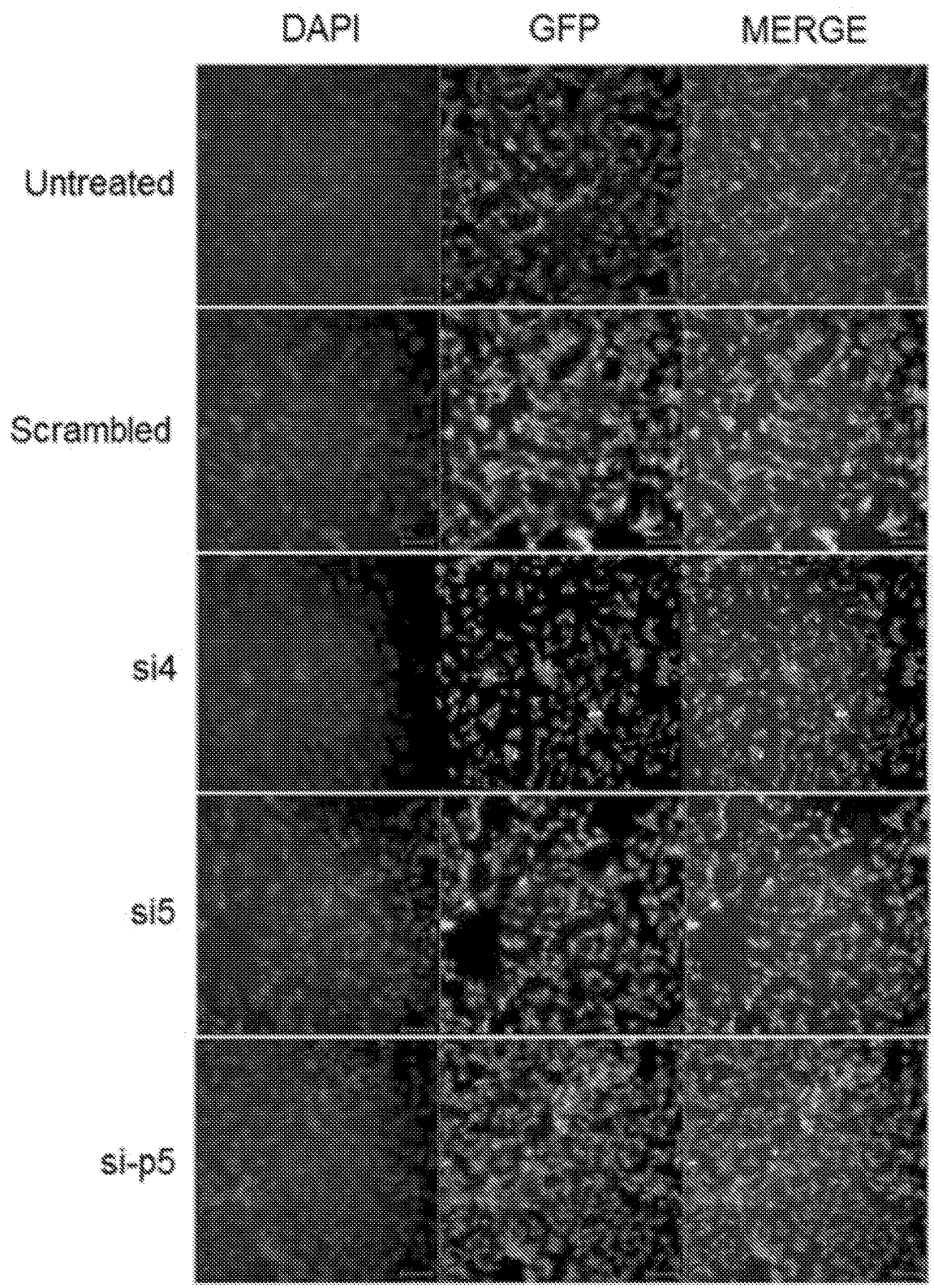

FIGS. 13A-13B show the effects of siRNAs and ASOs on LDL uptake in Hep3B cells. Hep3B cells were transfected with 50 nM duplex siRNAs or ASOs using lipofectamine RNAiMAX (Invitrogen). Cells were harvested 72 hours later and processed for LDL uptake using the LDL uptake assay kit (Molecular Probes, Invitrogen). Images were captured using the Zen Imaging Software (version 2.3, Carl Zeiss Microscopy GmbH), and arithmetic mean fluorescence intensity of the LDL-BIODIPY-FL were measured (FIG. 13A). FIG. 13B shows representative images of the LDL-uptake assay.

Figure 14:
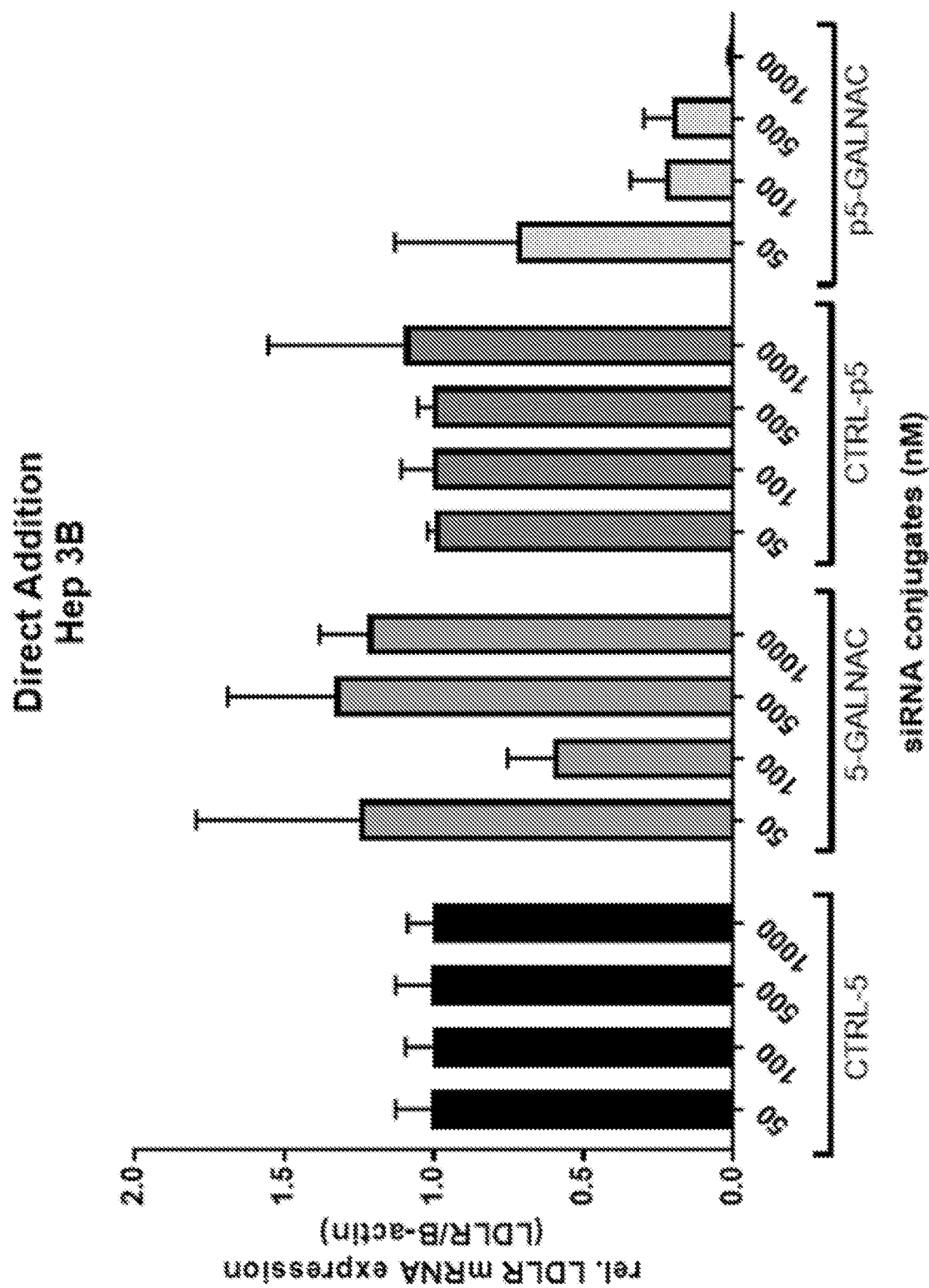
FIG. 14. Effect of siRNA 5 and p5 conjugated to a GalNAc on LDLR mRNA levels.

FIG. 14. Shows the dose-dependent effect of siRNA 5 and p5 conjugated to a GALNAC on LDLR mRNA levels. Increasing amounts (50, 100, 500 and 1000 nM) of scrambled or siRNA-conjugated GALNACs were directly added to Hep3B cells. Cells were harvested 72 hours later and processed for RNA (SimplyRNA, Promega). 100 ng total RNA was reverse transcribed to cDNA using an MM-LV reverse transcriptase (Invitrogen), and qPCR was performed. FIG. 14 shoes the relative LDLR mRNA expression levels in Hep3B cells, normalized to each control.

Figure 15A:
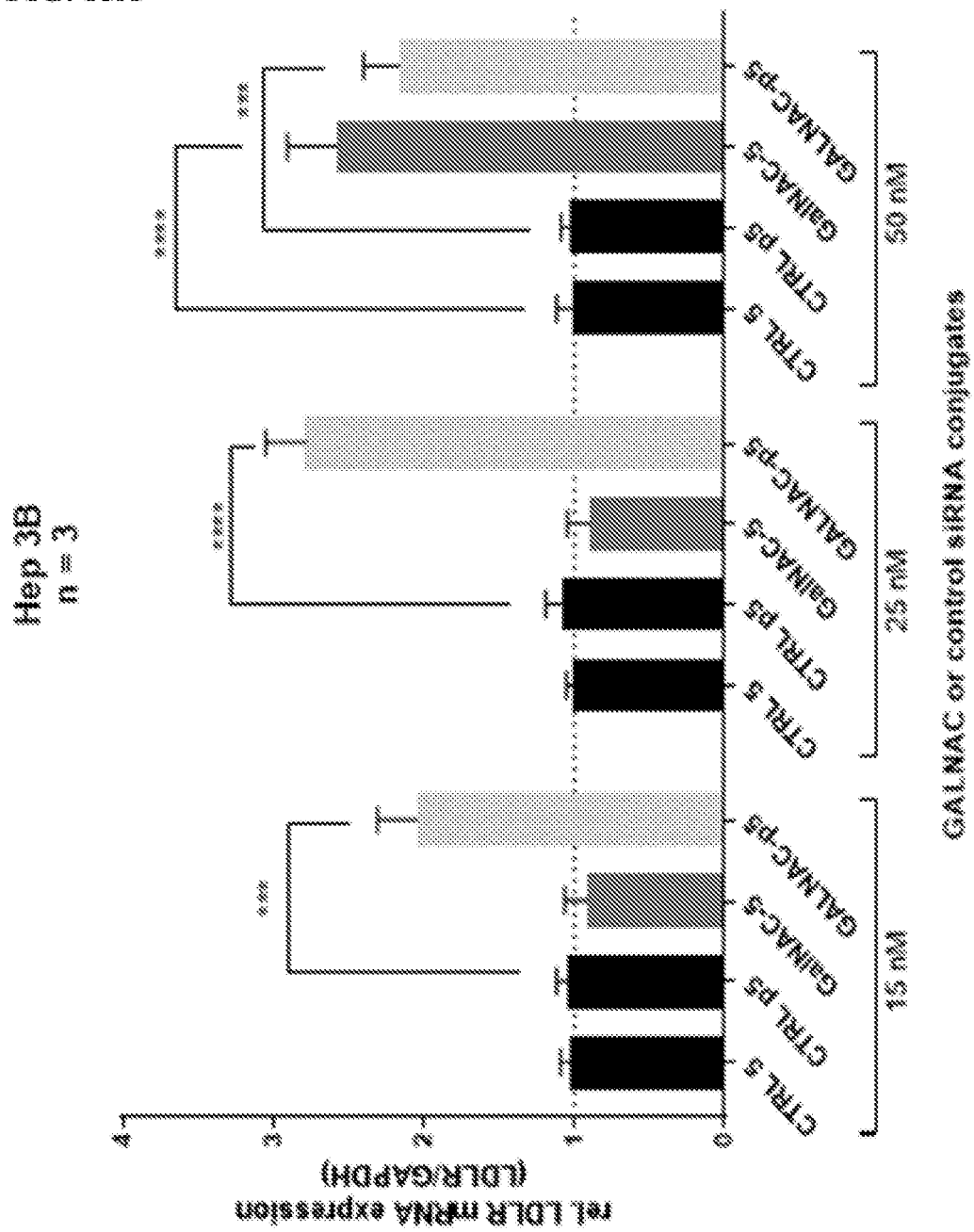
FIGS. 15A-15B. GalNAC siRNA conjugates significantly increase LDLR mRNA expression and decrease the lncRNA, BM450697 in a dose dependent manner.
Figure 15B:
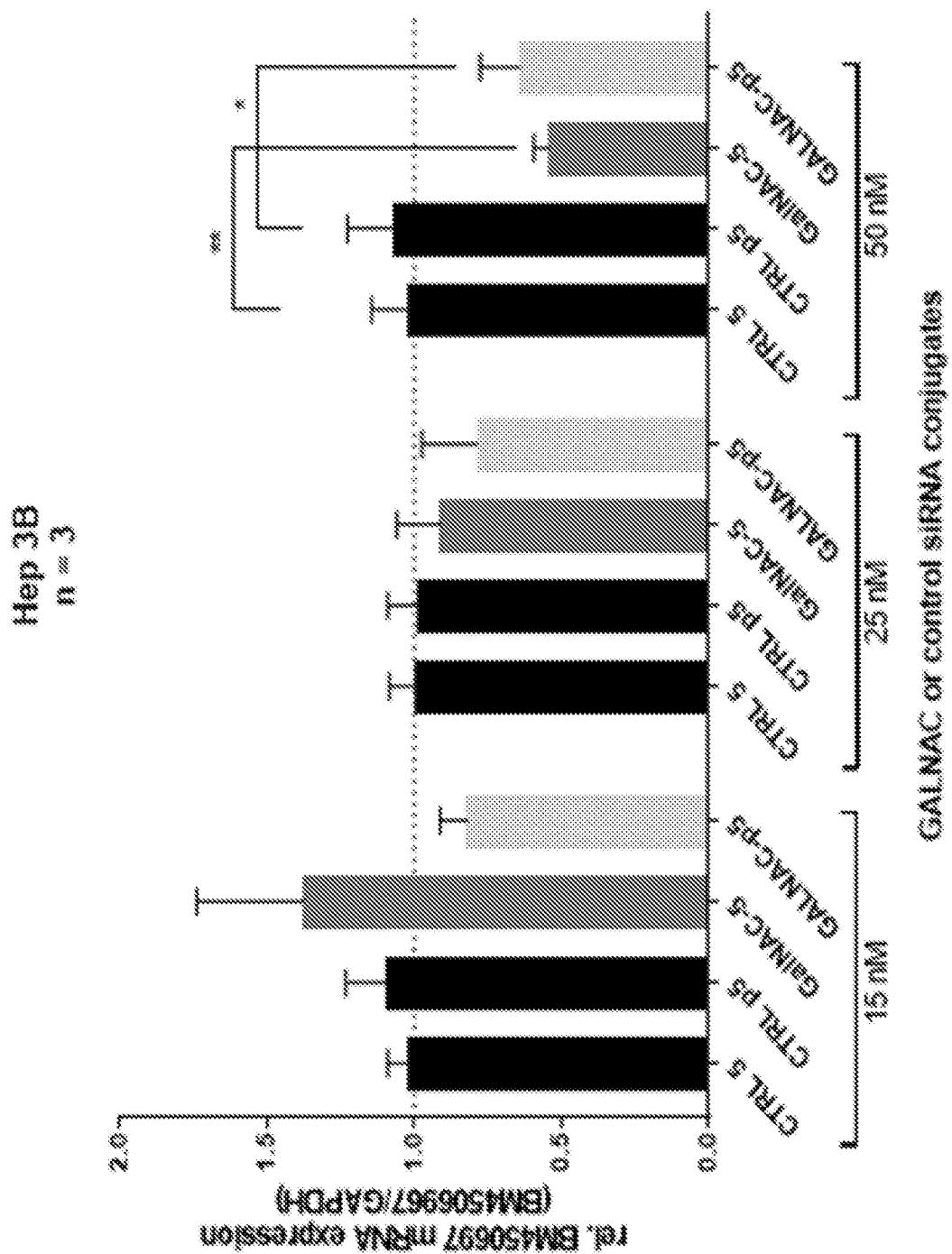

It was further shown that GalNAC siRNA conjugates significantly increase LDLR mRNA expression and decrease the lncRNA, BM45069, in a dose dependent manner. Hep 3B cells were seeded at a concentration of 100 000 cells/well. siRNA conjugates targeted towards the lncRNA or their corresponding scrambled conjugated controls were added to the cells at increasing concentrations (15, 25 and 50 nM). After 48 hours, cells were harvested for RNA using the SimplyRNA kit (Promega, USA), and reverse transcribed using the Quantitect cDNA kit with either random hexamers (FIG. 15A) or a strand specific primer (FIG. 15B) (Qiagen, USA). FIG. 15A shows relative LDLR mRNA expression levels and FIG. 15B shows relative BM450697 mRNA expression levels. Each siRNA conjugate was normalized to their respective scrambled control at each concentration set to 1.

Figure 16A:
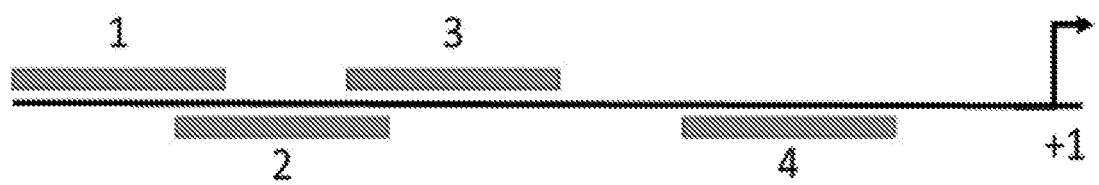
FIGS. 16A-16B. BM450697 is enriched at the promoter site of LDLR in Hep3B cells.
Figure 16B:
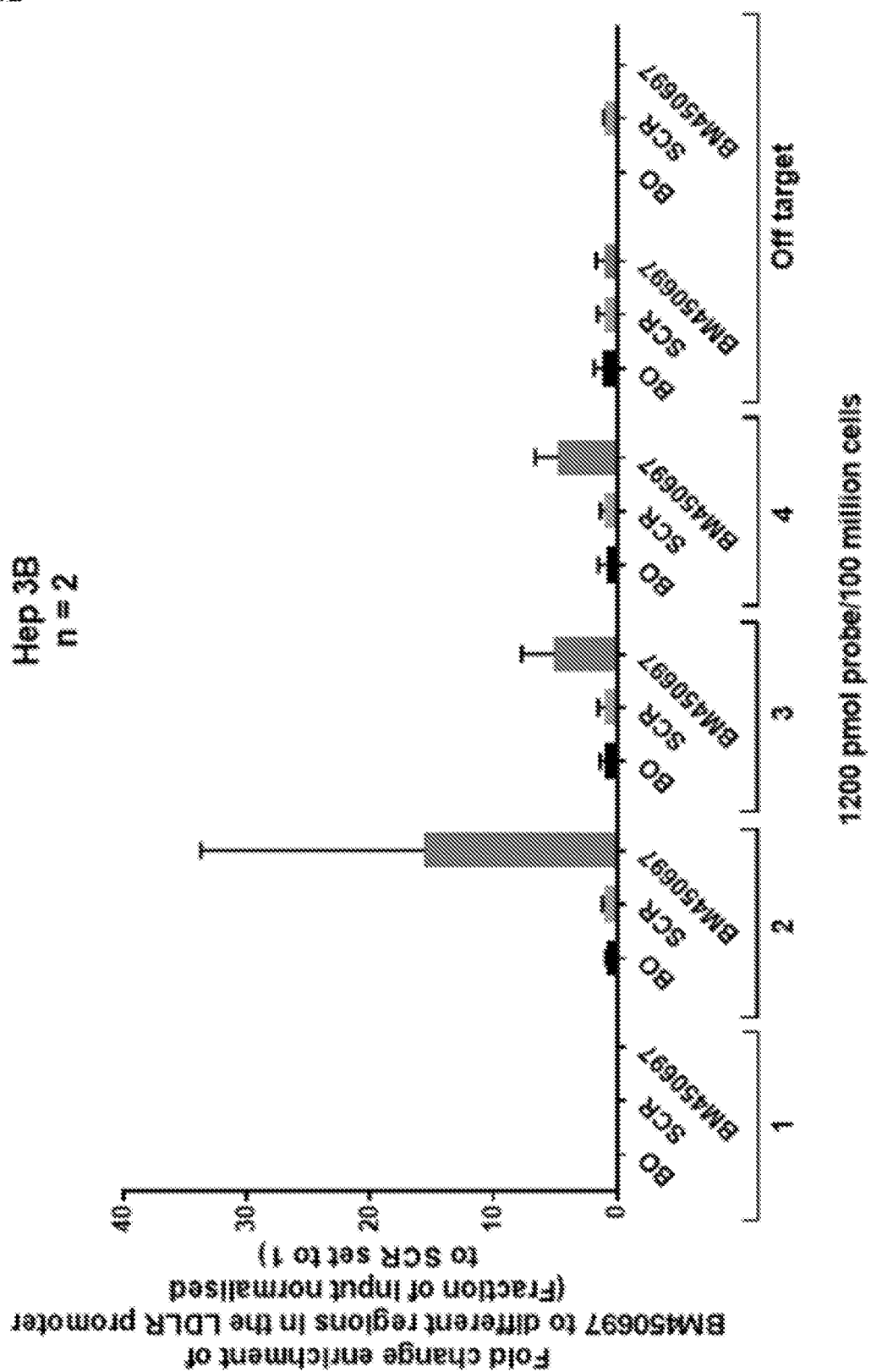

BM450697 was found to be enriched at the promoter site of LDLR in Hep3B cells. One hundred million Hep3B cells were harvested and incubated with either 5' biotinylated ASOs towards BM450697 or scrambled controls overnight at 37° C. Thereafter a CHIRP assay was performed and resultant genomic DNA was isolated after Rnase A and proteinase K treatment. Primer sets were designed towards different overlapping regions in the LDLR promoter (FIG. 16A) and subsequent qPCR was performed to determine the fold enrichment of BM450697 at the different promoter sites. Samples were calibrated to a fraction of input (1%) and normalized to the scrambled control set to 1. FIG. 16B shows the resultant qPCR using the LDLR primer sets 1-4 as well as off target genes (a downstream 8 kb LDLR gene primer set and GAPDH respectively).

REFERENCES

1. Jeon and Blacklow, Structure and physiologic function of the low-density lipoprotein receptor, Annu. Rev. Biochem. 2005. 74:535-62
2. Matsui et al., Activation of LDL Receptor Expression by Small RNAs Complementary to a Noncoding Transcript that Overlaps the LDLR Promoter, Chemistry & Biology 17, 1344-1355

```
INFORMAL SEQUENCE LISTING
SEQ ID NO: 1 (EST BM450697 Promoter)
CGUCUCAAAGAAGAUGCGGUCCCUCACCCUGUGGAGACUUGGGGGACAGC

GGUGCCCCGUUUCCCUUAAAUCCCUCAGACUCCUCCCGACCCUCGCGCUC

CCCUCAGCGCCCCCCUCCAGCGCCCCCUCCAGCCGUUUGGGAAGGACCCC

GUGCCAUUACCCCACAAGUCUCCCAGGGAUGGAGUGAUUAUUUGUACCCA

AAAAAAUAAAUUCCCAAGGGCCCCCCGGGGGCUCCCUCUCAACCUAUUCU

GGCGCCUGGAGCAAGCCUUACCUGCAGUCCCCGCCGCGGCGAGGAGCAAG

G

SEQ ID NO: 2 (EST BM450697)
GGGGCUCCCUCUCACCUAUUCUGGCGCCUGGAGCAAGCCUUACCUGCAGU

CCCCGCCGCGGCGAGGAGCAAGGCGACGGUCCAGCGCAAUUUCCAGCCCC

AGGGCCCCAUGCUCGCAGCCUCUGCCAGGCAGUGUCCCGACCCGGAUCAC

GACCUGCUGUGUCCUAGCUGGAAACCCUGGCUUCCCGCGAUUGCACUCGG

GGCCCACGUCAUUUACAGCAUUUCAAUGUGAGGUUUCUAGCAGGGGGAGG

AGUUUGCAGUGGGGUGAUUUUCAAAUGUCUUCACCUCACUGCAAGAGGAG

GAGUUUCGAACGGCCGAUGUGACAUCGGCUUUUUAACCCGUGAAGCUCUG
```

-continued
```
AUUCCCACUCCAGUCCUUCGAAAGUGUCGCCAGGGCAGGCGACUUGAUUU

GUUGUAUUUGGGUCUCCGGUGAAGAGCUGACGCCCCCUCAAAAUUGGAAA

CGCAUCUUCUGAAAGAUCCUCCUGAAAUUUCUCGAUGUUUAACUGUUAAC

AUUUUGCUGUUGUUGUCCACAGAAGGAUAACAACAGCCCUUUCAAGAUCC

CUCCAAUAGCCUAAUGCCAUUUGUCCUCUCUGCCUCCAAAGGAAAACACU

AAAAAUGGUGGGGAACUCCCGCCACCUUUCUAUAUUUGCCCUUUUCCUUU

UCCAGGAAUU
```

SEQ ID NO: 3 (BM45_pro-si1_S)
CCGUUUGGGAAGGACCCCGUGTT

SEQ ID NO: 4 (BM45_pro-si1_AS)
CACGGGGUCCUUCCCAAACGGTT

SEQ ID NO: 5 (BM45_pro-si2_S)
GUACCCAAAAAAAUAAAUUCCCAATT

SEQ ID NO: 6 (BM45_pro-si2_AS)
TTGGGAAUUUAUUUUUUUGGGUACTT

SEQ ID NO: 7 (BM45_pro-si3_S)
CCGCCGCGGCGAGGAGCAAGGTT

SEQ ID NO: 8 (BM45_pro-si3_AS)
CCUUGCUCCUCGCCGCGGCGGTT

SEQ ID NO: 9 (BM45_pro-si4_S)
UCUCCCAGGGAUGGAGUGAUUTT

SEQ ID NO: 10 (BM45_pro-si4_AS)
AAUCACUCCAUCCCUGGGAGATT

SEQ ID NO: 11 (BM45_pro-si5_S)
CCCUGUGGAGACUUGGGGGACTT

SEQ ID NO: 12 (BM45_pro-si5_AS)
GUCCCCCAAGUCUCCACAGGGTT

SEQ ID NO: 13 (BM45_si1_S)
UCUAGCAGGGGGAGGAGUUUGTT

SEQ ID NO: 14 (BM45_si1_AS)
CAAACUCCUCCCCCUGCUAGATT

SEQ ID NO: 15 (BM45_si2_S)
CACUGCAAGAGGAGGAGUUUCTT

SEQ ID NO: 16 (BM45_si2_AS)
GAAACUCCUCCUCUUGCAGUGTT

SEQ ID NO: 17 (BM45_si3_S)
GCCUCCAAAGGAAAACACUAATT

SEQ ID NO: 18 (BM45_si3_AS)
UUAGUGUUUUCCUUUGGAGGCTT

SEQ ID NO: 19 (BM45_si4_S)
GUCCACAGAAGGAUAACAACATT

SEQ ID NO: 20 (BM45_si4_AS)
UGUUGUUAUCCUUCUGUGGACTT

SEQ ID NO: 21 (BM45_si5_S)
CGCGGCGAGGAGCAAGGCGAC

SEQ ID NO: 22 (BM45_si5_AS)
GTCGCCUUGCUCCUCGCCGCG

SEQ ID NO: 23 (BM450697.1 AGENCOURT_6394526
NIH_MGC_67 Homo sapiens cDNA clone IMAGE:
5494402 5', mRNA sequence)
```
GGGGCTCCCTCTCACCTATTCTGGCGCCTGGAGCAAGCCTTACCTGCAGT

CCCCGCCGCGGCGAGGAGCAAGGCGACGGTCCAGCGCAATTTCCAGCCCC

AGGGCCCCATGCTCGCAGCCTCTGCCAGGCAGTGTCCCGACCCGGATCAC

GACCTGCTGTGTCCTAGCTGGAAACCCTGGCTTCCCGCGATTGCACTCGG

GGCCCACGTCATTTACAGCATTTCAATGTGAGGTTTCTAGCAGGGGGAGG

AGTTTGCAGTGGGGTGATTTTCAAATGTCTTCACCTCACTGCAAGAGGAG

GAGTTTCGAACGGCCGATGTGACATCGGCTTTTTAACCCGTGAAGCTCTG

ATTCCCACTCCAGTCCTTCGAAAGTGTCGCCAGGGCAGGCGACTTGATTT

GTTGTATTTGGGTCTCCGGTGAAGAGCTGACGCCCCCTCAAAATTGGAAA

CGCATCTTCTGAAAGATCCTCCTGAAATTTCTCGATGTTTAACTGTTAAC

ATTTTGCTGTTGTTGTCCACAGAAGGATAACAACAGCCCTTTCAAGATCC

CTCCAATAGCCTAATGCCATTTGTCCTCTCTGCCTCCAAAGGAAAACACT

AAAAATGGTGGGGAACTCCCGCCACCTTTCTATATTTGCCCTTTTCCTTT

TCCAGGAATTTGCGGAATACAATTTTTTAACCCCCCCTTTCCCTGGTAAT

AATCGCGTTTTTACCACTGGGTACTCCCAAACTGACCCCTAATCAAAAA

AACTGGATGTCCACCCCCGGAAAATTCTTAGAATAACAAATTCTTCTTCC

CCTACACCGCCCCGCGGCCTCTACTTGTATTACCCCCGTCGCCGTCACTC

ATGTCTCCCACCTTACGCCGCGCCGGCCTGAGCCCTACTTTAAGACAACC

CCGTTCGAGAGGGGACGCCAAGATTATTCCANCCGGTAACCCAACCTTTA

TCTCGGTGACCTAAACCGCTCGCTCACTACCAACTTGCCGGTACGCGTAT

CTAGAGACACATAATGCACTTCTGTCCGCCGACCTCATTACACCCTCCTC

GCTCCGCGGGGTACATCACTTGCCGGCCGTCCGTCTACACTCCCCTCGTT

TCTCTCGCCNTCTCACTACTTAGCCTCGGGATCTACCCAACTCGTTCACA

CACACACGCGCACCGCCATTACACAGTATGTACACCCGCCGCCGCAAAAT

AACNTGCCCTCACTGCCACCCCCACAT
```

SEQ ID NO: 24 (LDLR Forward primer)
ACCCCTCGAGACAGATGGTCA

SEQ ID NO: 25: (LDLR Reverse primer)
GGCACTGTCCGAAGCCTGTT

SEQ ID NO: 26 (β-actin Forward primer)
AGGTCATCACCATTGGCAATGAG

SEQ ID NO: 27 (β-actin Reverse primer)
TCTTTGCGGATGTCCACGTCA

SEQ ID NO: 28 (NF51)
(Stearyl-AGYLLG)δOINLKALAALAKKIL-NH$_2$

SEQ ID NO: 29 (NF57)
(Stearyl-AGYLLG)δOINLKALKALAKAIL-NH$_2$

SEQ ID NO: 30 (PF3)
Stearyl-AGYLLGKINLKALAALAKKIK-NH$_2$

SEQ ID NO: 31 (TP10)
AGYLLGKINLKALAALAKKIK-NH$_2$

SEQ ID NO: 32 (PF6)
Stearyl-AGYLLGKINLKALAALAKKIK-NH$_2$

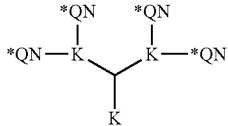

Wherein K is [structure] and *QN is [structure]

-continued

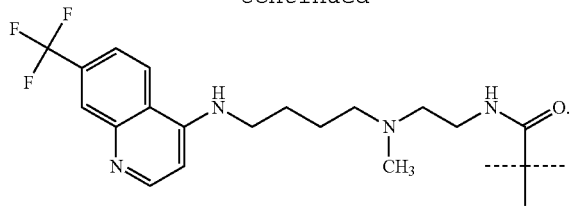

SEQ ID NO: 33 (PF14)
Stearyl-AGYLLGKLLOOLAAAALOOLL-NH2

SEQ ID NO: 34 (LMWP)
VSRRRRGGRRRRRR

SEQ ID NO: 35 (GAG KW-22)
KKGFYKKKQCRPSKGRKRGFCW

SEQ ID NO: 36 (NLS)
CGGGGPKKKRKVGGGGPKKKRKVGGGGPKKKRKV

SEQ ID NO: 37 (Tat peptide)
GRKKRRQRRR

SEQ ID NO: 38 (RT 1)
GACCTGCTGTGTCCTAGCTG

SEQ ID NO: 39 (F set 1)
CACTCCAGTCCTTCGAAAGTGTCG

SEQ ID NO: 40 (R set 1)
TTCCTTTGGAGGCAGAGAGGACA

SEQ ID NO: 41 (F set 2)
GGGGCTCCCTCTCACCTATTCT

SEQ ID NO: 42 (R set 2)
GAGGCTGCGAGCATGGG

EMBODIMENTS

Embodiment 1

A ribonucleic acid compound comprising an RNA sequence, said RNA sequence having at least 80% sequence identity to the complement of at least 15 consecutive nucleotides of nucleotides 1-147 of SEQ ID NO:1.

Embodiment 2

The ribonucleic acid compound of Embodiment 1, wherein said RNA sequence is capable of hybridizing to at least 15 consecutive nucleotides of nucleotides 1-147 of SEQ ID NO:1.

Embodiment 3

The ribonucleic acid compound of Embodiment 1 or 2, wherein said RNA sequence is capable of hybridizing to about 15, 16, 17, 18, 19, 20, 21, 22, 23, 24 or 25 consecutive nucleotides of nucleotides 1-147 of SEQ ID NO:1.

Embodiment 4

The ribonucleic acid compound of one of Embodiments 1-3, wherein said RNA sequence is capable of hybridizing to 21 consecutive nucleotides of nucleotides 1-147 of SEQ ID NO:1.

Embodiment 5

The ribonucleic acid compound of one of Embodiments 1-4, wherein said RNA sequence has at least 85% sequence identity to the complement of said consecutive nucleotides.

Embodiment 6

The ribonucleic acid compound of one of Embodiments 1-5, wherein said RNA sequence has at least 90% sequence identity to the complement of said consecutive nucleotides.

Embodiment 7

The ribonucleic acid compound of one of Embodiments 1-6, wherein said RNA sequence has at least 95% sequence identity to the complement of said consecutive nucleotides.

Embodiment 8

The ribonucleic acid compound of one of Embodiments 1-7, wherein said RNA sequence has at least 97% sequence identity to the complement of said consecutive nucleotides.

Embodiment 9

The ribonucleic acid compound of one of Embodiments 1-8, wherein said RNA sequence has at least 98% sequence identity to the complement of said consecutive nucleotides.

Embodiment 10

The ribonucleic acid compound of one of Embodiments 1-9, wherein said RNA sequence is capable of hybridizing to nucleotides 27-47 of SEQ ID NO:1.

Embodiment 11

The ribonucleic acid compound of Embodiment 10, wherein said RNA sequence has at least 80% sequence identity to the complement of SEQ ID NO:1.

Embodiment 12

The ribonucleic acid compound of Embodiment 10 or 11, wherein said RNA sequence has at least 85% sequence identity to the complement of SEQ ID NO:1.

Embodiment 13

The ribonucleic acid compound of one of Embodiments 10-12, wherein said RNA sequence has at least 90% sequence identity to the complement of SEQ ID NO:1.

Embodiment 14

The ribonucleic acid compound of one of Embodiments 10-13, wherein said RNA sequence has at least 95% sequence identity to the complement of SEQ ID NO:1.

Embodiment 15

The ribonucleic acid compound of one of Embodiments 10-14, wherein said RNA sequence has at least 97% sequence identity to the complement of SEQ ID NO:1.

Embodiment 16

The ribonucleic acid compound of one of Embodiments 10-15, wherein said RNA sequence has at least 98% sequence identity to the complement of SEQ ID NO:1.

Embodiment 17

The ribonucleic acid compound of one of Embodiments 1-16, wherein said RNA sequence is SEQ ID NO:12.

Embodiment 18

The ribonucleic acid compound of one of Embodiments 1-17, wherein said RNA sequence is a single-stranded RNA sequence.

Embodiment 19

The ribonucleic acid compound of one of Embodiments 1-17, wherein said RNA sequence is a double-stranded RNA sequence.

Embodiment 20

The ribonucleic acid compound of one of Embodiments 1-19, wherein said RNA sequence is an LDLR-activating sequence.

Embodiment 21

The ribonucleic acid compound of one of Embodiments 1-20, wherein said RNA sequence is a small RNA.

Embodiment 22

The ribonucleic acid compound of one of Embodiments 1-21, wherein said RNA sequence is a transcriptional gene silencing (TGS) RNA.

Embodiment 23

A ribonucleic acid compound comprising an RNA sequence, said RNA sequence having at least 80% sequence identity to the complement of at least 15 consecutive nucleotides of nucleotides 541-631 of SEQ ID NO:2.

Embodiment 24

The ribonucleic acid compound of Embodiment 23, wherein said RNA sequence is capable of hybridizing to at least 15 consecutive nucleotides of nucleotides 541-631 of SEQ ID NO:2.

Embodiment 25

The ribonucleic acid compound of Embodiment 23, wherein said RNA sequence is capable of hybridizing to about 15, 16, 17, 18, 19, 20, 21, 22, 23, 24 or 25 consecutive nucleotides of nucleotides 541-631 of SEQ ID NO:2.

Embodiment 26

The ribonucleic acid compound of Embodiment 23 or 25, wherein said RNA sequence is capable of hybridizing to 21 consecutive nucleotides of nucleotides 541-631 of SEQ ID NO:2.

Embodiment 27

The ribonucleic acid compound of one of Embodiments 23-26, wherein said RNA sequence has at least 85% sequence identity to the complement of said consecutive nucleotides.

Embodiment 28

The ribonucleic acid compound of one of Embodiments 23-27, wherein said RNA sequence has at least 90% sequence identity to the complement of said consecutive nucleotides.

Embodiment 29

The ribonucleic acid compound of one of Embodiments 23-28, wherein said RNA sequence has at least 95% sequence identity to the complement of said consecutive nucleotides.

Embodiment 30

The ribonucleic acid compound of one of Embodiments 23-29, wherein said RNA sequence has at least 97% sequence identity to the complement of said consecutive nucleotides.

Embodiment 31

The ribonucleic acid compound of one of Embodiments 23-30, wherein said RNA sequence has at least 98% sequence identity to the complement of said consecutive nucleotides.

Embodiment 32

The ribonucleic acid compound of one of Embodiments 23-31, wherein said RNA sequence is capable of hybridizing to nucleotides 582-602 of SEQ ID NO:2.

Embodiment 33

The ribonucleic acid compound of Embodiment 32, wherein said RNA sequence has at least 80% sequence identity to the complement of SEQ ID NO:2.

Embodiment 34

The ribonucleic acid compound of Embodiment 32 or 33, wherein said RNA sequence has at least 85% sequence identity to the complement of SEQ ID NO:2.

Embodiment 35

The ribonucleic acid compound of one of Embodiments 32-34, wherein said RNA sequence has at least 90% sequence identity to the complement of SEQ ID NO:2.

Embodiment 36

The ribonucleic acid compound of one of Embodiments 32-35, wherein said RNA sequence has at least 95% sequence identity to the complement of SEQ ID NO:2.

Embodiment 37

The ribonucleic acid compound of one of Embodiments 32-36, wherein said RNA sequence has at least 97% sequence identity to the complement of SEQ ID NO:2.

Embodiment 38

The ribonucleic acid compound of one of Embodiments 32-37, wherein said RNA sequence has at least 98% sequence identity to the complement of SEQ ID NO:2.

Embodiment 39

The ribonucleic acid compound of one of Embodiments 23-38, wherein said RNA sequence is SEQ ID NO:18.

Embodiment 40

The ribonucleic acid compound of one of Embodiments 23-39, wherein said RNA sequence is a single-stranded RNA sequence.

Embodiment 41

The ribonucleic acid compound of one of Embodiments 23-40, wherein said RNA sequence is a double-stranded RNA sequence.

Embodiment 42

The ribonucleic acid compound of one of Embodiments 23-41, wherein said RNA sequence is an LDLR-activating sequence.

Embodiment 43

The ribonucleic acid compound of one of Embodiments 23-42, wherein said RNA sequence is an siRNA.

Embodiment 44

The ribonucleic acid compound of one of Embodiments 23-43, wherein said RNA sequence is a post-transcriptional gene silencing (PTGS) RNA.

Embodiment 45

The ribonucleic acid compound of one of Embodiments 1 to 22 or 23-44, comprising a compound moiety covalently attached to said RNA sequence.

Embodiment 46

The ribonucleic acid compound of Embodiment 45, wherein said compound moiety is a trivalent (triantennary) N-acetylgalactosamine moiety.

Embodiment 47

The ribonucleic acid compound of Embodiment 45, wherein said compound moiety is a cholesterol moiety.

Embodiment 48

A pharmaceutical formulation comprising the ribonucleic acid compound of one of Embodiments 1 to 22 or 23-47 and a pharmaceutically acceptable excipient.

Embodiment 49

A method of treating hypercholesterolemia, said method comprising administering to a subject in need thereof an effective amount of the ribonucleic acid compound of one of Embodiments 1 to 22 or 23-47.

Embodiment 50

A method of activating LDLR in a cell, said method comprising contacting a cell with an effective amount of the ribonucleic acid compound of one of Embodiments 1 to 22 or 23-47, thereby activating LDLR in a cell.

Embodiment 51

The method of Embodiment 50, wherein said method further comprises allowing binding of said ribonucleic acid compound to an LDLR-lncRNA.

Embodiment 52

The method of Embodiment 51, wherein said ribonucleic acid compound is capable of hybridizing to the promoter of said LDLR-lncRNA.

Embodiment 53

A method of inhibiting expression of an LDLR-lncRNA in a cell, said method comprising contacting a cell with an effective amount of the ribonucleic acid compound of one of Embodiments 1 to 22 or 23-47, thereby inhibiting expression of an LDLR-lncRNA in a cell.

---

What is claimed is:

1. A method of treating hypercholesterolemia, said method comprising administering to a subject in need thereof an effective amount of a ribonucleic acid compound, said ribonucleic acid compound comprising an RNA sequence having at least 95% sequence identity to the complement of at least 15 consecutive nucleotides of nucleotides 1-147 of SEQ ID NO:1, wherein said RNA sequence is capable of hybridizing to nucleotides 27-47 of SEQ ID NO:1; or said ribonucleic acid compound comprising an RNA sequence having at least 95% sequence identity to the complement of at least 15 consecutive nucleotides of nucleotides 541-631 of SEQ ID NO:2, wherein said RNA sequence is capable of hybridizing to nucleotides 582-602 of SEQ ID NO:2.

2. The method of claim 1, wherein said RNA sequence is SEQ ID NO:12.

3. The method of claim 1, wherein said RNA sequence is SEQ ID NO:18.

* * * * *

UNITED STATES PATENT AND TRADEMARK OFFICE
CERTIFICATE OF CORRECTION

PATENT NO. : 11,242,531 B2  
APPLICATION NO. : 16/483392  
DATED : February 8, 2022  
INVENTOR(S) : Kevin V. Morris and Roslyn Ray Page 1 of 1

It is certified that error appears in the above-identified patent and that said Letters Patent is hereby corrected as shown below:

In the Specification

At Column 1, Line 15, before the "REFERENCE TO A "SEQUENCE LISTING," A TABLE, OR A COMPUTER PROGRAM LISTING APPENDIX SUBMITTED ON A COMPACT DISC", please insert the following paragraph:
--STATEMENT AS TO RIGHTS TO INVENTIONS MADE UNDER FEDERALLY SPONSORED RESEARCH AND DEVELOPMENT
This invention was made with government support under AI099783, AI111139, and DK104681 awarded by the National Institutes of Health. The government has certain rights in the invention.--

Signed and Sealed this
Tenth Day of October, 2023

Katherine Kelly Vidal
*Director of the United States Patent and Trademark Office*

SEQUENCE LISTING

<160> NUMBER OF SEQ ID NOS: 42

<210> SEQ ID NO 1
<211> LENGTH: 301
<212> TYPE: RNA
<213> ORGANISM: Artificial sequence
<220> FEATURE:
<223> OTHER INFORMATION: Synthetic Polynucleotide

<400> SEQUENCE: 1

```
cgucucaaag aagaugcggu cccucacccu guggagacuu gggggacagc ggugccccgu      60
uucccuuaaa ucccucagac uccucccgac ccucgcgcuc cccucagcgc cccccuccag     120
```

```
cgccccucc  agccguuugg  gaaggacccc  gugccauuac  cccacaaguc  ucccagggau    180
ggagugauua  uuuguaccca  aaaaauaaa   ucccaaggg   cccccgggg   gcucccucuc    240 aaccuauucu  ggcgccugga  gcaagccuua  ccugcaguc   ccgccgcggc  gaggagcaag    300
g                                                                        301

<210> SEQ ID NO 2
<211> LENGTH: 660
<212> TYPE: RNA
<213> ORGANISM: Artificial sequence
<220> FEATURE:
<223> OTHER INFORMATION: Synthetic Polynucleotide

<400> SEQUENCE: 2
ggggcucccu  cucaccuauu  cuggcgccug  gagcaagccu  uaccugcagu  ccccgccgcg    60
gcgaggagca  aggcgacggu  ccagcgcaau  uccagcccc   agggcccau   gcucgcagcc    120 ucugccaggc  aguucccga   cccggaucac  gaccugcugu  guccuagcug  gaaacccugg    180
cuucccgcga  uugcacucgg  ggcccacguc  auuuacagca  uuucaaugug  agguuucuag    240 caggggagg   aguuugcagu  ggggugauuu  ucaaaugucu  ucaccucacu  gcaagaggag    300
gaguuucgaa  cggccgaugu  gacaucggcu  uuuuaacccg  ugaagcucug  auucccacuc    360
caguccuucg  aaagugucgc  cagggcaggc  gacuugauuu  guuguauuug  ggucuccggu    420
gaagagcuga  cgcccccuca  aaauuggaaa  cgcaucuucu  gaaagauccu  ccugaaauuu    480
cucgauguuu  aacuguuaac  auuuugcugu  uguugccac   agaaggauaa  caacagcccu    540
uucaagaucc  cuccaauagc  cuaaugccau  uuguccucuc  ugccuccaaa  ggaaaacacu    600 aaaaaugggug  gggaaucccc  gccaccuuuc  uauauuugcc  cuuuccuuu   uccaggaauu    660

<210> SEQ ID NO 3
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 3
ccguuuggga  aggaccccgu  gtt                                              23

<210> SEQ ID NO 4
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 4
cacggggucc  uucccaaacg  gtt                                              23

<210> SEQ ID NO 5
<211> LENGTH: 26
<212> TYPE: DNA
<213> ORGANISM: Artificial sequence
<220> FEATURE:
<223> OTHER INFORMATION: Synthetic Polynucleotide

<400> SEQUENCE: 5
guacccaaaa  aaauaaauuc  ccaatt                                           26
```

```
<210> SEQ ID NO 6
<211> LENGTH: 26
<212> TYPE: DNA
<213> ORGANISM: Artificial sequence
<220> FEATURE:
<223> OTHER INFORMATION: Synthetic Polynucleotide

<400> SEQUENCE: 6
ttgggaauuu auuuuuugg guactt                                      26

<210> SEQ ID NO 7
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 7
ccgccgcggc gaggagcaag gtt                                        23

<210> SEQ ID NO 8
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 8
ccuugcuccu cgccgcggcg gtt                                        23

<210> SEQ ID NO 9
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 9
ucucccaggg auggagugau utt                                        23

<210> SEQ ID NO 10
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 10
aaucacucca ucccugggag att                                        23

<210> SEQ ID NO 11
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 11
cccuguggag acuuggggga ctt                                        23

<210> SEQ ID NO 12
<211> LENGTH: 23
<212> TYPE: DNA
<213> ORGANISM: Artificial sequence
<220> FEATURE:
<223> OTHER INFORMATION: Synthetic Polynucleotide
```

```
<400> SEQUENCE: 12
gucccccaag ucuccacagg gtt                                              23

<210> SEQ ID NO 13
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 13
ucuagcaggg ggaggaguuu gtt                                              23

<210> SEQ ID NO 14
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 14
caaacuccuc ccccugcuag att                                              23

<210> SEQ ID NO 15
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 15
cacugcaaga ggaggaguuu ctt                                              23

<210> SEQ ID NO 16
<211> LENGTH: 21
<212> TYPE: RNA
<213> ORGANISM: Artificial sequence
<220> FEATURE:
<223> OTHER INFORMATION: Synthetic Polynucleotide

<400> SEQUENCE: 16
gaaacuccuc cucuugcagu g                                                21

<210> SEQ ID NO 17
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 17
gccuccaaag gaaaacacua att                                              23

<210> SEQ ID NO 18
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 18
uuaguguuuu ccuuuggagg ctt                                              23
```

```
<210> SEQ ID NO 19
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 19
guccacagaa ggauaacaac att                                            23

<210> SEQ ID NO 20
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 20
uguuguuauc cuucugugga ctt                                            23

<210> SEQ ID NO 21
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 21
cgcggcgagg agcaaggcga c                                              21

<210> SEQ ID NO 22
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 22
gtcgccttgc tcctcgccgc g                                              21

<210> SEQ ID NO 23
<211> LENGTH: 1227
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1204)..(1204)
<223> OTHER INFORMATION: n is a, c, g, or t

<400> SEQUENCE: 23
ggggctccct ctcacctatt ctggcgcctg gagcaagcct tacctgcagt ccccgccgcg     60
gcgaggagca aggcgacggt ccagcgcaat tccagcccc agggcccat gctcgcagcc     120 tctgccaggc agtgtcccga cccggatcac gacctgctgt gtcctagctg gaaaccctgg   180
cttcccgcga ttgcactcgg ggcccacgtc atttacagca tttcaatgtg aggtttctag   240 caggggagg agtttgcagt ggggtgattt tcaaatgtct tcacctcact gcaagaggag    300
```

```
gagtttcgaa cggccgatgt gacatcggct ttttaacccg tgaagctctg attcccactc    360
cagtccttcg aaagtgtcgc cagggcaggc gacttgattt gttgtatttg ggtctccggt    420
gaagagctga cgcccctca aaattggaaa cgcatcttct gaaagatcct cctgaaattt     480
ctcgatgttt aactgttaac attttgctgt tgttgtccac agaaggataa caacagccct    540
ttcaagatcc ctccaatagc ctaatgccat ttgtcctctc tgcctccaaa ggaaaacact    600
aaaaatggtg gggaactccc gccacctttc tatatttgcc cttttccttt tccaggaatt    660
tgcggaatac aatttttaa ccccccttt ccctggtaat aatcgcgttt ttaccactgg      720
gtactcccca aactgacccc taatcaaaaa aactggatgt ccaccccgg aaaattctta    780 gaataacaaa ttcttcttcc cctacaccgc cccgcggcct ctacttgtat taccccgtc     840 gccgtcactc atgtctccca ccttacgccg cgccggcctg agccctactt taagacaacc    900
ccgttcgaga ggggacgcca agattattcc anccggtaac ccaaccttta tctcggtgac    960
ctaaaccgct cgctcactac caacttgccg gtacgcgtat ctagagacac ataatgcact   1020
tctgtccgcc gacctcatta caccctcctc gctccgcggg gtacatcact tgccggccgt   1080
ccgtctacac tccctcgtt tctctcgccn tctcactact tagcctcggg atctacccaa    1140
ctcgttcaca cacacgcg caccgccatt acacagtatg tacacccgcc gccgcaaaat    1200
aacntgccct cactgccacc cccacat                                       1227

<210> SEQ ID NO 24
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 24
acccctcgag acagatggtc a                                               21

<210> SEQ ID NO 25
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 25
ggcactgtcc gaagcctgtt                                                 20

<210> SEQ ID NO 26
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 26
aggtcatcac cattggcaat gag                                             23

<210> SEQ ID NO 27
<211> LENGTH: 21
<212> TYPE: DNA
<213> ORGANISM: Artificial sequence
<220> FEATURE:
<223> OTHER INFORMATION: Synthetic Polynucleotide

<400> SEQUENCE: 27
tctttgcgga tgtccacgtc a                                               21
```

```
<210> SEQ ID NO 28
<211> LENGTH: 21
<212> TYPE: PRT
<213> ORGANISM: Artificial sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Stearyl
<220> FEATURE:
<221> NAME/KEY: MOD_RES
<222> LOCATION: (7)..(7)
<223> OTHER INFORMATION: Orn
<220> FEATURE:
<221> NAME/KEY: MISC_FEATURE
<222> LOCATION: (21)..(21)
<223> OTHER INFORMATION: amine

<400> SEQUENCE: 28

Ala Gly Tyr Leu Leu Gly Xaa Ile Asn Leu Lys Ala Leu Ala Ala Leu
1               5                   10                  15

Ala Lys Lys Ile Leu
            20

<210> SEQ ID NO 29
<211> LENGTH: 21
<212> TYPE: PRT
<213> ORGANISM: Artificial sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Stearyl
<220> FEATURE:
<221> NAME/KEY: MOD_RES
<222> LOCATION: (7)..(7)
<223> OTHER INFORMATION: Orn
<220> FEATURE:
<221> NAME/KEY: misc_feature
<222> LOCATION: (21)..(21)
<223> OTHER INFORMATION: amine

<400> SEQUENCE: 29

Ala Gly Tyr Leu Leu Gly Xaa Ile Asn Leu Lys Ala Leu Lys Ala Leu
1               5                   10                  15

Ala Lys Ala Ile Leu
            20

<210> SEQ ID NO 30
<211> LENGTH: 21
<212> TYPE: PRT
<213> ORGANISM: Artificial sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Stearyl
<220> FEATURE:
<221> NAME/KEY: misc_feature
<222> LOCATION: (21)..(21)
<223> OTHER INFORMATION: amine

<400> SEQUENCE: 30

Ala Gly Tyr Leu Leu Gly Lys Ile Asn Leu Lys Ala Leu Ala Ala Leu
1               5                   10                  15

Ala Lys Lys Ile Lys
            20
```

```
<210> SEQ ID NO 31
<211> LENGTH: 21
<212> TYPE: PRT
<213> ORGANISM: Artificial sequence
<220> FEATURE:
<223> OTHER INFORMATION: Synthetic Polypeptide
<220> FEATURE:
<221> NAME/KEY: misc_feature
<222> LOCATION: (21)..(21)
<223> OTHER INFORMATION: amine

<400> SEQUENCE: 31

Ala Gly Tyr Leu Leu Gly Lys Ile Asn Leu Lys Ala Leu Ala Ala Leu
1               5                   10                  15

Ala Lys Lys Ile Lys
            20

<210> SEQ ID NO 32
<211> LENGTH: 21
<212> TYPE: PRT
<213> ORGANISM: Artificial sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Stearyl
<220> FEATURE:
<221> NAME/KEY: misc_feature
<222> LOCATION: (21)..(21)
<223> OTHER INFORMATION: amine

<400> SEQUENCE: 32

Ala Gly Tyr Leu Leu Gly Lys Ile Asn Leu Lys Ala Leu Ala Ala Leu
1               5                   10                  15

Ala Lys Lys Ile Lys
            20

<210> SEQ ID NO 33
<211> LENGTH: 21
<212> TYPE: PRT
<213> ORGANISM: Artificial sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: stearyl
<220> FEATURE:
<221> NAME/KEY: MOD_RES
<222> LOCATION: (10)..(11)
<223> OTHER INFORMATION: Orn
<220> FEATURE:
<221> NAME/KEY: MOD_RES
<222> LOCATION: (18)..(19)
<223> OTHER INFORMATION: Orn
<220> FEATURE:
<221> NAME/KEY: misc_feature
<222> LOCATION: (21)..(21)
<223> OTHER INFORMATION: amine

<400> SEQUENCE: 33

Ala Gly Tyr Leu Leu Gly Lys Leu Leu Xaa Xaa Leu Ala Ala Ala Ala
1               5                   10                  15

Leu Xaa Xaa Leu Leu
            20
```

```
<210> SEQ ID NO 34
<211> LENGTH: 14
<212> TYPE: PRT
<213> ORGANISM: Artificial sequence
<220> FEATURE:
<223> OTHER INFORMATION: Synthetic Polypeptide

<400> SEQUENCE: 34

Val Ser Arg Arg Arg Arg Gly Gly Arg Arg Arg Arg Arg Arg
1               5                   10

<210> SEQ ID NO 35
<211> LENGTH: 22
<212> TYPE: PRT
<213> ORGANISM: Artificial sequence
<220> FEATURE:
<223> OTHER INFORMATION: Synthetic Polypeptide

<400> SEQUENCE: 35

Lys Lys Gly Phe Tyr Lys Lys Lys Gln Cys Arg Pro Ser Lys Gly Arg
1               5                   10                  15

Lys Arg Gly Phe Cys Trp
            20

<210> SEQ ID NO 36
<211> LENGTH: 34
<212> TYPE: PRT
<213> ORGANISM: Artificial sequence
<220> FEATURE:
<223> OTHER INFORMATION: Synthetic Polypeptide

<400> SEQUENCE: 36

Cys Gly Gly Gly Gly Pro Lys Lys Lys Arg Lys Val Gly Gly Gly Gly
1               5                   10                  15

Pro Lys Lys Lys Arg Lys Val Gly Gly Gly Gly Pro Lys Lys Lys Arg
            20                  25                  30

Lys Val

<210> SEQ ID NO 37
<211> LENGTH: 10
<212> TYPE: PRT
<213> ORGANISM: Artificial sequence
<220> FEATURE:
<223> OTHER INFORMATION: Synthetic Polypeptide

<400> SEQUENCE: 37

Gly Arg Lys Lys Arg Arg Gln Arg Arg Arg
1               5                   10

<210> SEQ ID NO 38
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 38
gacctgctgt gtcctagctg                                                 20

<210> SEQ ID NO 39
<211> LENGTH: 24
<212> TYPE: DNA
<213> ORGANISM: Artificial sequence
<220> FEATURE:
<223> OTHER INFORMATION: Synthetic polynucleotide
```

```
<400> SEQUENCE: 39
cactccagtc cttcgaaagt gtcg                                          24

<210> SEQ ID NO 40
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 40
ttcctttgga ggcagagagg aca                                           23

<210> SEQ ID NO 41
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 41
ggggctccct ctcacctatt ct                                            22

<210> SEQ ID NO 42
<211> LENGTH: 17
<212> TYPE: DNA
<213> ORGANISM: Artificial sequence
<220> FEATURE:
<223> OTHER INFORMATION: Synthetic polynucleotide

<400> SEQUENCE: 42
gaggctgcga gcatggg                                                  17
```